(12) United States Patent
Dai

(10) Patent No.: US 8,454,160 B2
(45) Date of Patent: *Jun. 4, 2013

(54) ZONE EXTENSION SYSTEMS AND METHODS

(75) Inventor: Guang-ming Dai, Fremont, CA (US)

(73) Assignee: AMO Development, LLC, Santa Ana, CA (US)

( * ) Notice: Subject to any disclaimer, the term of this patent is extended or adjusted under 35 U.S.C. 154(b) by 179 days.

This patent is subject to a terminal disclaimer.

(21) Appl. No.: 13/008,488

(22) Filed: Jan. 18, 2011

(65) Prior Publication Data

US 2011/0149241 A1 Jun. 23, 2011

Related U.S. Application Data

(63) Continuation-in-part of application No. 12/793,095, filed on Jun. 3, 2010, which is a continuation-in-part of application No. 12/725,575, filed on Mar. 17, 2010, now Pat. No. 7,967,436, which is a continuation of application No. 11/832,408, filed on Aug. 1, 2007, now Pat. No. 7,695,136, application No. 13/008,488, which is a continuation-in-part of application No. 12/722,881, filed on Mar. 12, 2010, now Pat. No. 7,887,187, which is a continuation of application No. 11/676,094, filed on Feb. 16, 2007, now Pat. No. 7,717,562.

(60) Provisional application No. 61/419,629, filed on Dec. 3, 2010, provisional application No. 61/412,118, filed on Nov. 10, 2010, provisional application No. 60/776,289, filed on Feb. 24, 2006.

(51) Int. Cl.
*G02C 7/02* (2006.01)

(52) U.S. Cl.
USPC .................................. 351/159.78; 351/159.74

(58) Field of Classification Search
USPC .............. 351/159.01, 159.52, 159.74, 159.78
See application file for complete search history.

(56) References Cited

U.S. PATENT DOCUMENTS

| 4,665,913 A | 5/1987 | L'Esperance, Jr. |
| 4,669,466 A | 6/1987 | L'Esperance |

(Continued)

FOREIGN PATENT DOCUMENTS

| WO | WO 02/098290 A | 12/2002 |
| WO | WO 2004/113958 A | 12/2004 |

OTHER PUBLICATIONS

Bara, Salvador et al. "Direct Transformation of Zernike Eye Aberration Coefficients Between Scaled, Rotaed, and/or Displaced pupils", Journal of the Optical Society of America, 2006, vol. 23, No. 9, Sep. 2006, pp. 2061-2066.

(Continued)

*Primary Examiner* — Jordan Schwartz
(74) *Attorney, Agent, or Firm* — Kilpatrick Townsend & Stockton LLP

(57) ABSTRACT

Wavefront measurements of eyes are often taken when the pupil is in a first configuration in an evaluation context. The results can be represented by a set of basis function coefficients. Prescriptive treatments are often applied in a treatment context, which is different from the evaluation context. Hence, the patient pupil can be in a different, second configuration, during treatment. Systems and methods are provided for determining a transformed set of basis function coefficients, based on a difference between the first and second configurations, which can be used to establish the vision treatment.

18 Claims, 31 Drawing Sheets

U.S. PATENT DOCUMENTS

| | | | |
|---|---|---|---|
| 4,732,148 | A | 3/1988 | L'Esperance, Jr. |
| 4,770,172 | A | 9/1988 | L'Esperance, Jr. |
| 4,773,414 | A | 9/1988 | L'Esperance, Jr. |
| 5,108,388 | A | 4/1992 | Trokel |
| 5,163,934 | A | 11/1992 | Munnerlyn |
| 5,207,668 | A | 5/1993 | L'Esperance, Jr. |
| 5,219,343 | A | 6/1993 | L'Esperance, Jr. |
| 5,646,791 | A | 7/1997 | Glockler |
| 5,683,379 | A | 11/1997 | Hohla |
| 5,713,892 | A | 2/1998 | Shimmick |
| 5,807,379 | A | 9/1998 | L'Esperance, Jr. |
| 6,004,313 | A | 12/1999 | Shimmick et al. |
| 6,095,651 | A | 8/2000 | Williams et al. |
| 6,203,539 | B1 | 3/2001 | Shimmick et al. |
| 6,271,915 | B1 | 8/2001 | Frey et al. |
| 6,315,413 | B1 | 11/2001 | Shimmick et al. |
| 6,331,177 | B1 | 12/2001 | Munnerlyn et al. |
| 6,682,196 | B2 * | 1/2004 | Sheets et al. .......... 351/246 |
| 6,698,889 | B2 * | 3/2004 | Pettit et al. ............ 351/246 |
| 6,827,444 | B2 | 12/2004 | Williams et al. |
| 7,293,873 | B2 | 11/2007 | Dai et al. |
| 7,434,936 | B2 | 10/2008 | Dai et al. |
| 7,537,341 | B2 * | 5/2009 | Saito et al. ............ 351/205 |
| 7,695,136 | B2 | 4/2010 | Dai |
| 7,717,562 | B2 | 5/2010 | Dai |
| 7,887,187 | B2 | 2/2011 | Dai |
| 7,967,436 | B2 | 6/2011 | Dai |
| 2003/0225399 | A1 | 12/2003 | Chernyak et al. |
| 2004/0169820 | A1 | 9/2004 | Dai et al. |
| 2005/0134799 | A1 | 6/2005 | Thompson et al. |
| 2005/0270491 | A1 | 12/2005 | Dai et al. |
| 2007/0058132 | A1 | 3/2007 | Dai |
| 2007/0222948 | A1 | 9/2007 | Dai |
| 2008/0117231 | A1 | 5/2008 | Kimpe |
| 2008/0198331 | A1 | 8/2008 | Azar et al. |
| 2009/0036980 | A1 | 2/2009 | Norrby et al. |
| 2009/0039980 | A1 | 2/2009 | Shafer |
| 2009/0086163 | A1 | 4/2009 | Dai et al. |
| 2010/0179520 | A1 | 7/2010 | Dai |
| 2010/0198567 | A1 | 8/2010 | Dai |
| 2010/0231855 | A1 | 9/2010 | Thompson et al. |
| 2010/0253909 | A1 | 10/2010 | Dai |

OTHER PUBLICATIONS

Campbell, Charles E., "Matrix Method to Find a New Set of Zernike Coefficients From an Original Set When the Aperture Radius is Changed", Journal of the Optical Society of America, 2003, vol. 20, No. 2, Feb. 2003, pp. 209-217.

Dai, Guang-Ming, "Scaling Zernike Expansion Coefficients to Smaller Pupil Sizes: A Simpler Formula", Journal of the Optical Society of America, 2006, vol. 23, No. 3, Mar. 2006, pp. 539-543.

Goldberg, Kenneth et al., "Wave-Front Measurement Errors From Restricted Concentric Subdomains", Journal of the Optical Society of America, 2001, vol. 18, No. 9, Sep. 2001, pp. 2146-2152.

Guirao, Antonio et al., "Effect of Rotation and Translation on the Expected Benefit of an Ideal Method to Correct the Eye's Higher-Order Aberrations", Journal of the Optical Society of America, 2001, vol. 18, No. 5, May 2001, pp. 1003-1015.

Janssen, Augustus et al., "Concise Formula for the Zernike Coefficients of Scaled Pupils", Journal of Microlithography, Microfabrication, and Microsystems, Jul.-Sep. 2006/vol. 5(3), pp. 30501-1 to 30501-3.

Lundstrom, Linda et al., "Transformation of Zernike Coefficients: Scaled, Translated, and Rotated Wavefronts With Circular and Elliptical Pupils", Journal of the Optical Society of America, vol. 24, No. 3, Mar. 2007, pp. 569-577.

Schweigerling, Jim, "Scaling Zernike expansion coefficients to different pupil sizes", Journal of the Optical Society of America, 2002, vol. 19, No. 10, Oct. 2002, pp. 1937-1945.

Shu, Huazhong et al., "General Method to Derive the Relationship Between Two Sets of Zernike Coefficients Corresponding to Different Aperture Sizes", Journal of the Optical Society of America, 2006, vol. 23, No. 8, Aug. 2006, pp. 1960-1966.

Wilson, M. A. et al., "The Julius F. Neumueller Award in Optics, 1989: Change of Pupil Centration with Change of Illumination and Pupil Size", Optom. and Vis. Sci., 69, No. 2 : 129-136 (1992).

Yang, Yabo et al., "Pupil Location Under Mesopic, Photopic, and Pharmacologically Dilated Conditions", Investigative Opthalmalogy & Visual Science, Jul. 2002, vol. 43, No. 7, pp. 2508-2512.

* cited by examiner

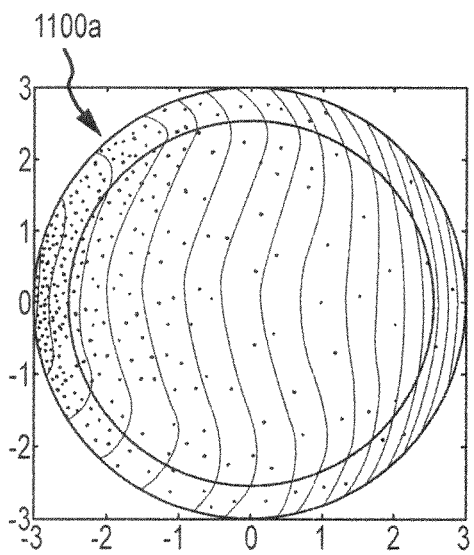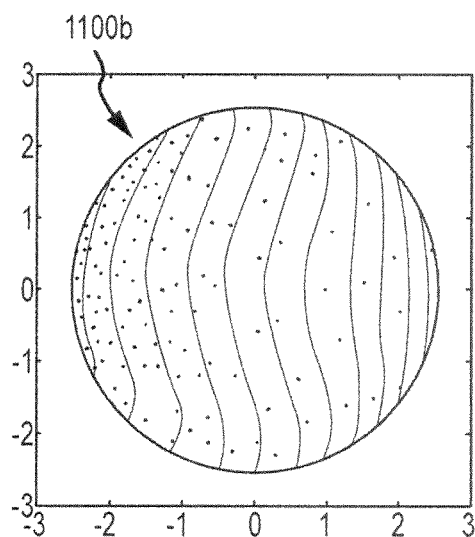
FIG.11A  FIG.11B
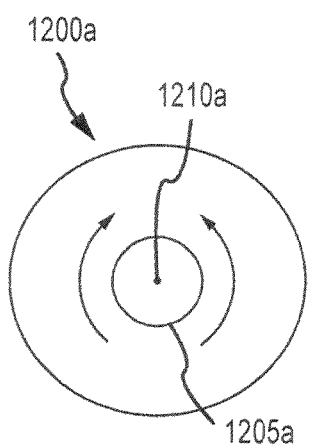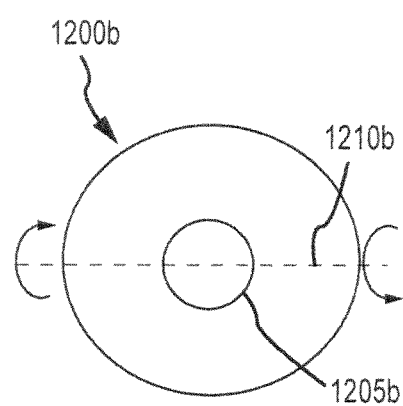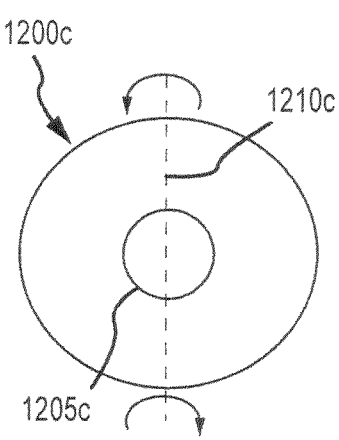
FIG.12A  FIG.12B  FIG.12C

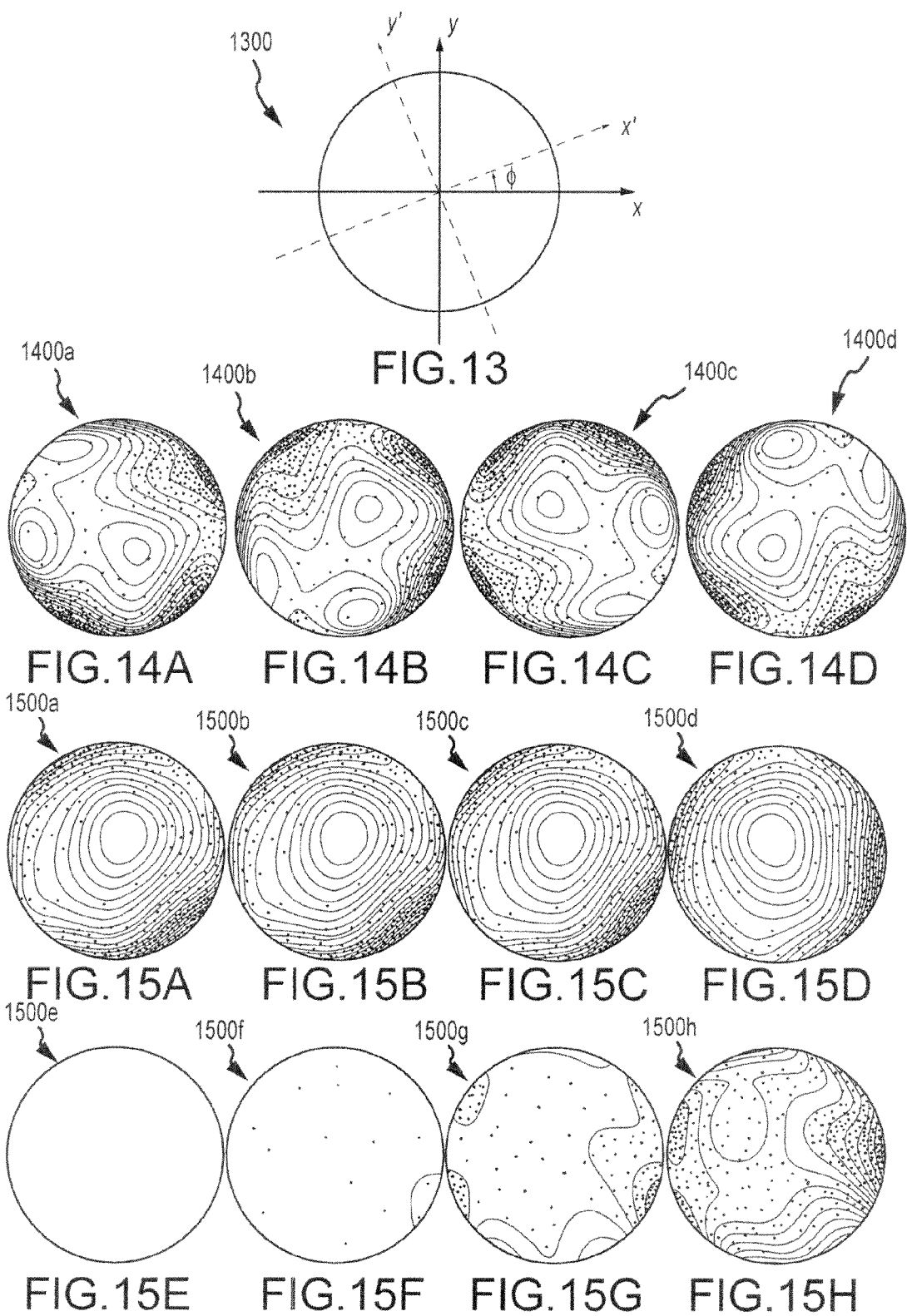

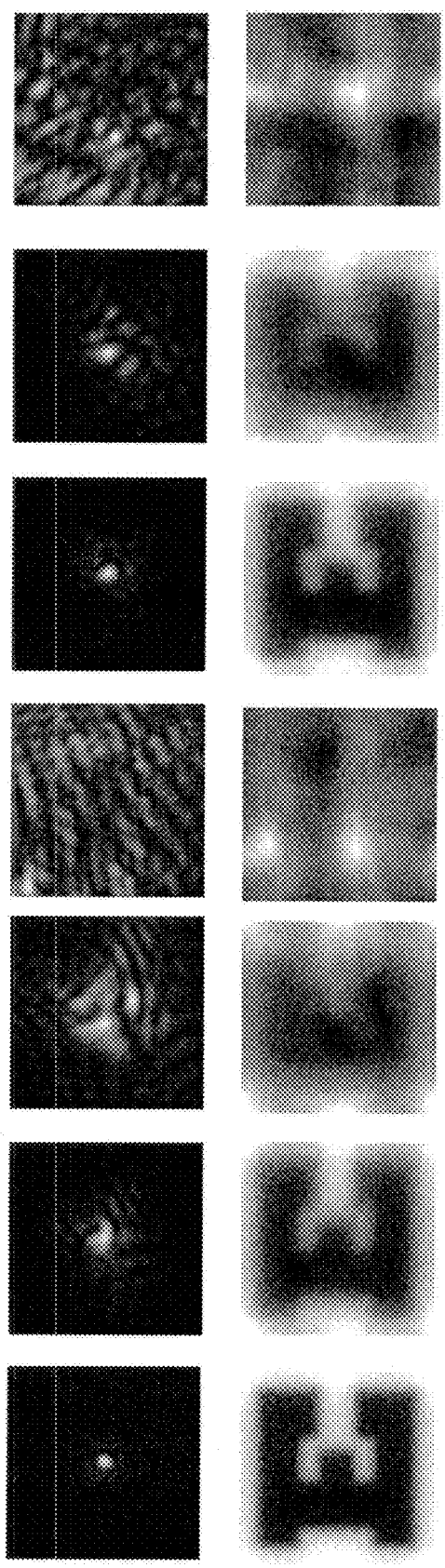

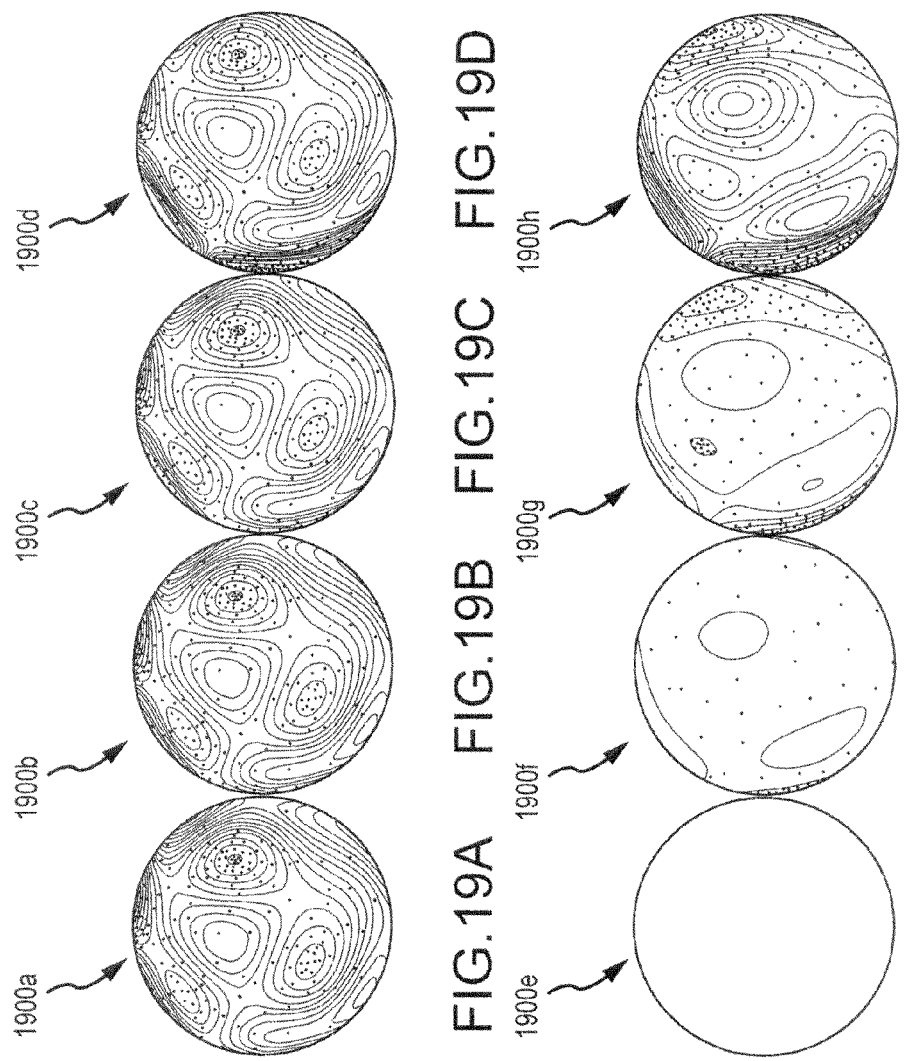

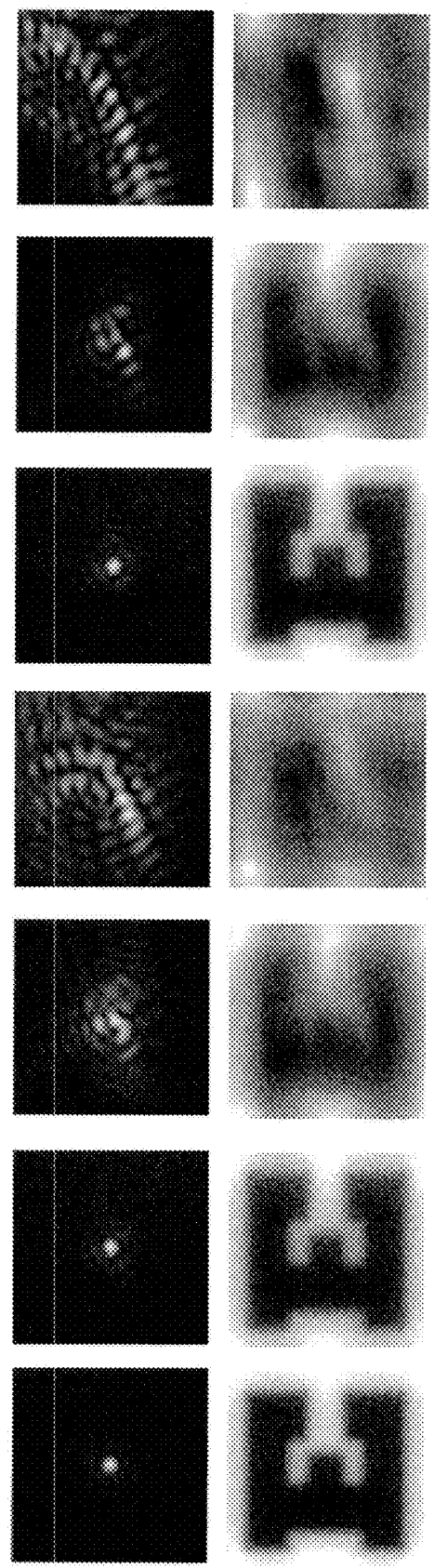

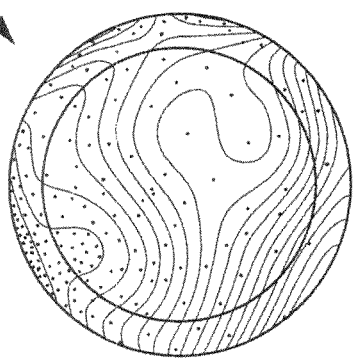 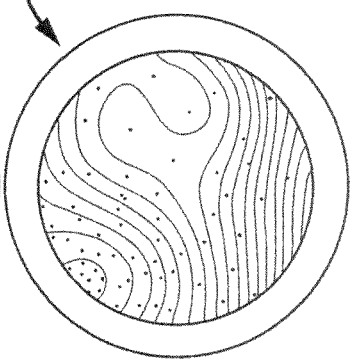
FIG.21A  FIG.21B
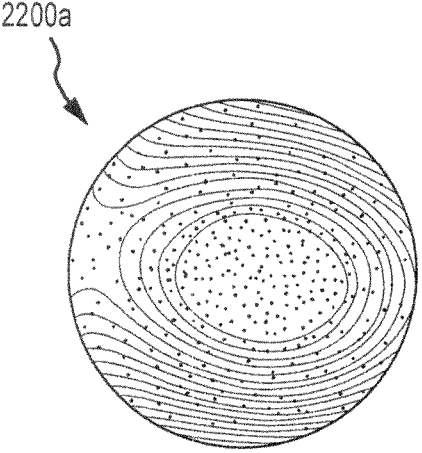 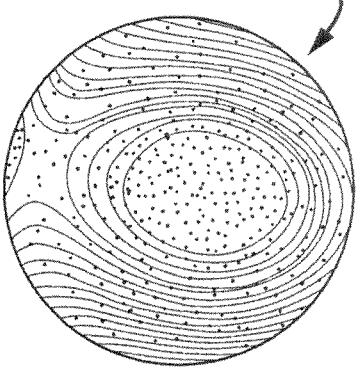
FIG.22A  FIG.22B
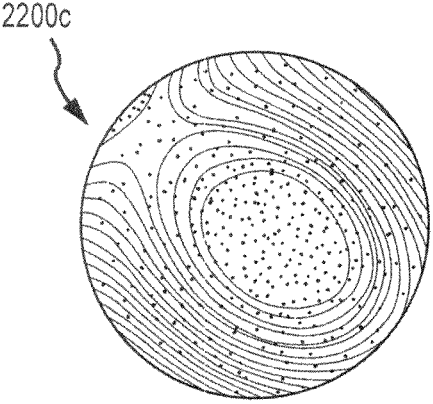 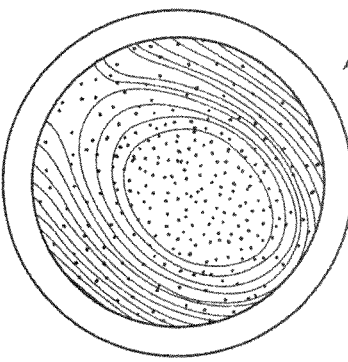
FIG.22C  FIG.22D

ZONE EXTENSION SYSTEMS AND METHODS

CROSS-REFERENCES TO RELATED APPLICATIONS

This application is a nonprovisional of, and claims the benefit of priority to, U.S. Provisional Patent Application Nos. 61/412,118 and 61/419,629, filed Nov. 10 and Dec. 3, 2010, respectively. This application is also a continuation-in-part of U.S. patent application Ser. No. 12/793,095, filed Jun. 3, 2010, which is a continuation-in-part of U.S. patent application Ser. No. 12/725,575, filed Mar. 17, 2010, which is a continuation of U.S. patent application Ser. No. 11/832,408, filed Aug. 1, 2007, now U.S. Pat. No. 7,695,136. This application is also a continuation-in-part of U.S. patent application Ser. No. 12/722,881, filed Mar. 12, 2010, which is a continuation of U.S. patent application Ser. No. 11/676,094, filed Feb. 16, 2007, which claims the benefit of U.S. Provisional Patent Application No. 60/776,289, filed Feb. 24, 2006. The content of each of the above listed applications is incorporated herein by reference.

BACKGROUND OF THE INVENTION

Embodiments of the present invention relate to systems and methods for treating vision in a patient. Particular embodiments encompass treatment techniques that account for geometrical transformations or zone extensions, such as those associated with pupil dilation.

Ocular aberrations of human eyes can be measured objectively with wavefront technology. In the various fields of optics, wavefront aberrations have traditionally been represented by Zernike polynomials. Wavefront measurements of eyes are normally taken when the pupil is relatively large, and the results are often represented by a set of Zernike coefficients. Different sets of Zernike coefficients can be calculated to represent aberrations at smaller pupil sizes. Pupil sizes may change according to the lighting environment or context where a patient is situated, for example. Nonrecursive analytical formulae have been derived to calculate a set of new Zernike polynomial expansion coefficients from an original set when the size of the aperture is reduced or enlarged. Optionally, such formulae may be used to calculate the instantaneous refractive power. In some cases, techniques allow scaling of the expansion coefficients with Zernike polynomials. Related scaling approaches can used with other basis functions, such as Taylor monomials. Similar techniques may account for other geometrical transformations, such as pupil center shift and cyclorotation.

Although these and other proposed treatment devices and methods may provide real benefits to patients in need thereof, still further advances would be desirable. For example, there continues to be a need for improved ablation systems and methods that consider the contribution of induced high order aberrations due to geometrical transformations which may include pupil constriction, pupil dilation, pupil center shift, or cyclorotation. Relatedly, there remains a need for improved general analytical errorless approaches for determining a new set of coefficients of any basis functions from an original set when an ocular wavefront map evokes a geometrical transformation that includes pupil constriction, a pupil dilation, a cyclorotation, or a pupil center shift, or any combination thereof. There also remains a need for improved general geometrical transformation techniques that do not have the restriction of a sub-area definition after such a geometrical transformation. Relatedly, there remains a need for improved optimal analytical errorless approaches for calculating wavefront refractions when a geometrical transformation occurs. There also remains a need for improved tissue ablation profiles that include the adjustment of such geometrical transformations for the correction of high order aberrations. Further, there is often an error or discrepancy between the manifest refraction and wavefront refraction. There remains a need for improved systems and methods for combining a CustomVue treatment with a shifted presbyopic treatment. Embodiments of the present invention provide solutions for vision treatment that address at least some of these needs.

BRIEF SUMMARY OF THE INVENTION

The ocular aberrations of human eyes can be measured objectively by ophthalmological techniques based on wavefront technology. In the various fields of optics, wavefront aberrations have traditionally been represented by Zernike polynomials.

Wavefront measurements of eyes may be taken when the pupil is relatively large, and the results are often represented by a set of Zernike coefficients. Different sets of Zernike coefficients can be calculated to represent aberrations at smaller pupil sizes. Relatedly, wavefront measurements of eyes may betaken when the pupil is relatively small, and the results are often represented by a set of Zernike coefficients. Different sets of Zernike coefficients can be calculated to represent aberrations at larger pupil sizes. Exemplary techniques allow scaling of the expansion coefficients with Zernike polynomials. Related approaches may employ non-recursive formulae between the new and the original sets of Zernike polynomial expansion coefficients of a wavefront when the aperture size is scaled.

Ocular wavefront maps typically change when the pupil parameters change. These map changes can reflect geometrical transformations such as pupil constrictions, dilations, cyclorotations, and pupil center shifts. Any one of these geometrical transformations, or any combination thereof, can result in a different set of Zernike or other basis function coefficients, thus affecting the calculation of wavefront refractions and the design of vision correction profiles such as for the correction or treatment of presbyopia. Embodiments of the present invention provide systems and methods for calculating wavefront refractions and for designing optimal or optimized ablation shapes for vision correction when a geometrical transformation occurs in an ocular wavefront map. Often these techniques involve improvements in accuracy for wavefront determinations. Embodiments disclosed herein are well suited for use in many vision correction and treatment modalities, including without limitation corneal ablation, contact lenses, intraocular lenses, and spectacle lenses.

Hence, an exemplary treatment method may include obtaining a wavefront of the patient's eye when the patient is in an evaluation environment or context and the eye is in a certain geometrical configuration. The wavefront can be characterized by a set of coefficients for a basis function. The method can also include exposing the patient to a treatment environment or context, such that the eye is in a new geometrical configuration. A new wavefront can be determined based on the earlier geometrical configuration of the eye, the original set of coefficients, and the new geometrical configuration. The new wavefront map can be characterized by a new set of coefficients for the basis function. Based on the new wavefront, it is possible to establish a prescription for the patient. The method can also include treating the patient with the prescription.

Embodiments of the present invention provide systems and methods for calculating a new set of coefficients of any basis functions from an original set when an ocular wavefront map evokes a geometrical transformation that includes pupil constrictions, dilations, cyclorotation, or pupil center shift, based on a general analytical or errorless approach. For example, in the case of a basis function representation of one or more particular ocular aberrations, embodiments disclosed herein provide techniques for determining a new set of basis function coefficients that reflect changes in pupil parameters or geometrical transformations. These techniques can be used to determine or characterize how geometrical transformations affect visual performance and the refraction determinations. It has been discovered that any basis function which can be separated into radial polynomials and a triangular function can be characterized by a generic pupil rescaling formula (GPRF).

Embodiments also provide a general geometrical transformation approach that does not have the restriction of a sub-area definition after such a geometrical transformation. Embodiments encompass cases where the set of basis functions is the set of Taylor monomials, or Zernike polynomials. Embodiments also encompass cases where the geometrical transformation includes only a pupil constriction, only a pupil dilation, only a cyclorotation, only a pupil center shift, or a combination of any two of these geometrical transformations, or a combination of all three. Embodiments of the present invention also provide systems and methods for calculating wavefront refractions when a geometrical transformation occurs, based on an optimal analytical or errorless approach for calculating. Embodiments also provide techniques for establishing tissue ablation profiles and other vision treatment profiles that include adjustments for, or otherwise consider, such geometrical transformations for the correction of high order aberrations. In some embodiments, systems and methods provide for the presbyopic treatments where the presbyopic shape is decentered, rotated, or otherwise shifted, and the profile is combined with the customized treatment, such as a CustomVue treatment. Embodiments also provide treatments that correct for or address errors or discrepancies between the manifest refraction and wavefront refraction.

As noted above, embodiments of the present invention provide techniques for scaling several types of basis functions. Moreover, embodiments provide techniques for obtaining new coefficients due to pupil parameter changes such as pupil constriction, dilation, decentration, and cyclorotation. Techniques can include any desired combination, in any desired order. Pupil decentration embodiments may involve x- and y-shifts. Cyclorotation embodiments may involve the angle of rotation. In some cases, it is assumed that the ocular aberrations are invariant of the coordinate change, and the aberrations are manifested from the optics of the eye, such as the cornea, the crystalline lens, and the media therebetween. The relative position and the property of optical components often does not change because of the pupil constriction, dilation, decentration, and cyclo-rotation. Hence, it is possible to establish an original domain that defines the original ocular aberrations, or in a broad sense, an original function. When the domain changes, it is possible to establish a new domain within the original domain. When the new domain is determined, various approaches can be used to fit the ocular aberration, or in a broad sense, a function, with a complete set of basis functions, such as Zernike polynomials, Fourier series, Taylor monomials, and the like. This approach can be applied to pupil parameter changes or geometrical transformations such as pupil constriction, dilation, decentration, and cyclo-rotation.

When a wavefront map is captured, it may be desirable to design an ablation treatment based on adjustments to the size or orientation of the map. Wavefront exams can be processed to adjust for changes in pupil size or alignment. For example, a treatment area may not be exactly the same as the area under which a wavefront is captured. Hence, it can be useful, after determining an original set of basis function coefficients, to determine a new set of basis function coefficients corresponding to a different ocular configuration.

In a first aspect, embodiments of the present invention encompass systems and methods for calculating a modified normalized Zernike expansion coefficient for an optical system. Exemplary methods may include inputting an original normalized Zernike expansion coefficient for the optical system, where the original normalized Zernike expansion coefficient is associated with a first aperture dimension, and calculating a modified normalized Zernike expansion coefficient for the optical system, where the modified normalized Zernike expansion coefficient is associated with a second aperture dimension, and the second aperture dimension is greater than the first aperture dimension. The modified normalized Zernike expansion coefficient can be calculated based on the original normalized Zernike expansion coefficient scaled by a scaling factor. The scaling factor can include a ratio of the second aperture dimension to the first aperture dimension, where the ratio is raised to the power of a factor including a radial degree of the coefficient. The aperture dimension can include an aperture radius. The optical system can include an optical tissue of a patient, and the aperture dimension can include a pupil dimension. The pupil dimension can include a pupil radius.

In another aspect, embodiments of the present invention encompass methods of determining an optical surface model for an optical tissue system of an eye. Methods may include inputting a first optical data corresponding to the optical tissue system of the eye, where the first optical data includes a first set of normalized Zernike expansion coefficients corresponding to a first pupil radius of the eye, and calculating a second optical data corresponding to the optical tissue of the eye, where the second optical data includes a second set of normalized Zernike expansion coefficients corresponding to a second pupil radius of the eye, and the second pupil radius of the eye is greater than the first pupil radius of the eye. The second set of normalized Zernike expansion coefficient can be calculated based on the first set of normalized Zernike expansion coefficients scaled by a scaling factor. The scaling factor can include a ratio of the second aperture dimension to the first aperture dimension, and the ratio can be raised to the power of a factor including a radial degree of the coefficient. Methods may also include determining the optical surface model based on the second optical data. Relatedly, methods may involve administering a treatment to the eye based on the optical surface model.

In another aspect, embodiments of the present invention encompass systems for calculating a modified normalized Zernike expansion coefficient for an optical system. Exemplary systems may include means for inputting an original normalized Zernike expansion coefficient for the optical system, where the original normalized Zernike expansion coefficient is associated with a first aperture dimension, and means for calculating a modified normalized Zernike expansion coefficient for the optical system, where the modified normalized Zernike expansion coefficient is associated with a second aperture dimension, and the second aperture dimension greater than the first aperture dimension. The modified normalized Zernike expansion coefficient can be calculated based on the original normalized Zernike expansion coefficient scaled by a scaling factor. The scaling factor can include a ratio of the second aperture dimension to the first aperture dimension, and the ratio can be raised to the power of a factor including a radial degree of the coefficient. In some cases, the aperture dimension includes an aperture radius. In some cases, the optical system includes an optical tissue of a patient, and the aperture dimension includes a pupil dimension. In some cases, the pupil dimension includes a pupil radius.

In another aspect, embodiments of the present invention encompass methods of calculating effective powers of an optical system. Methods may include calculating a first effective power using a first Zernike expansion coefficient for the optical system, where the first Zernike expansion coefficient is associated with a first aperture dimension, and calculating a second effective power using a second Zernike expansion coefficient for the optical system, where the second Zernike expansion coefficient is associated with a second aperture dimension, and the second aperture dimension is greater than the first aperture dimension. The second Zernike expansion coefficient can be scaled relative to the first Zernike expansion coefficient using a scaling factor that includes a ratio of the second aperture dimension to the first aperture dimension raised to a power of a factor including a radial degree of the coefficient. The optical system can include an optical tissue of a patient, and the aperture dimension can include a pupil dimension. In some cases, the pupil dimension includes a pupil radius.

In still another aspect, embodiments of the present invention encompass systems for calculating effective power for an optical system. Exemplary systems may include means for inputting a first Zernike expansion coefficient for the optical system, where the first Zernike expansion coefficient is associated with a first aperture dimension, and means for calculating a second effective power using a second Zernike expansion coefficient for the optical system, where the second Zernike expansion coefficient is associated with a second aperture dimension, and the second aperture dimension is greater than the first aperture dimension. The second Zernike expansion coefficient can be scaled relative to the first Zernike expansion coefficient using a scaling factor that includes a ratio of the second aperture dimension to the first aperture dimension raised to a power of a factor that includes a radial degree of the coefficient. In some cases, the optical system includes an optical tissue of a patient, and the aperture dimension includes a pupil dimension. In some cases, the pupil dimension includes a pupil radius.

In yet another aspect, embodiments of the present invention encompass computer program products for calculating a modified normalized Zernike expansion coefficient for an optical system. Exemplary computer program product can include code for accepting an original normalized Zernike expansion coefficient for the optical system, where the original normalized Zernike expansion coefficient is associated with a first aperture dimension, and code for calculating the modified normalized Zernike expansion coefficient for the optical system, where the modified normalized Zernike expansion coefficient is associated with a second aperture dimension, and the second aperture dimension is greater than the first aperture dimension. The modified normalized Zernike expansion coefficient can be calculated based on the original normalized Zernike expansion coefficient scaled by a scaling factor, and the scaling factor can include a ratio of the second aperture dimension to the first aperture dimension, where the ratio is raised to the power of a factor that includes a radial degree of the coefficient. Computer program products may also include a computer-readable medium for storing the codes. In some cases, the optical system includes an optical tissue of a patient, and the first aperture dimension includes a first pupil dimension. In some cases, the first pupil dimension includes a first pupil radius. In some cases, the optical system includes an optical tissue of a patient, and the second aperture dimension includes a second pupil dimension. In some cases, the second pupil dimension includes a second pupil radius. In some cases, the first aperture dimension includes a first aperture radius. In some cases, the second aperture dimension includes a second aperture radius.

In still a further aspect, embodiments of the present invention encompass computer program products for determining an optical surface model for an optical tissue system of an eye. Exemplary computer program products include code for accepting a first optical data corresponding to the optical tissue system of the eye, where the first optical data includes a first set of normalized Zernike expansion coefficients corresponding to a first aperture dimension, and code for calculating a second optical data corresponding to the optical tissue of the eye, where the second optical data includes a second set of normalized Zernike expansion coefficients corresponding to a second aperture dimension, and the second aperture dimension is greater than the first aperture dimension. The second set of normalized Zernike expansion coefficient can be calculated based on the first set of normalized Zernike expansion coefficients scaled by a scaling factor, where the scaling factor includes a ratio of the second aperture dimension to the first aperture dimension, and the ratio is raised to the power of a factor including a radial degree of the coefficient. Computer program products can also include code for determining the optical surface model based on the second optical data. Computer program products can also include a computer-readable medium for storing the codes. In some cases, the first aperture dimension includes a first pupil dimension. In some cases, the first pupil dimension includes a first pupil radius. In some cases, the second aperture dimension includes a second pupil dimension. In some cases, the second pupil dimension includes a second pupil radius. Computer program products can also include code for determining a treatment for the eye based on the optical surface model.

In another aspect, embodiments of the present invention encompass computer program products for calculating effective powers of an optical system. Exemplary computer program products include code for calculating a first effective power using a first Zernike expansion coefficient for the optical system, where the first Zernike expansion coefficient is associated with a first aperture dimension, and code for calculating a second effective power using a second Zernike expansion coefficient for the optical system, where the second Zernike expansion coefficient is associated with a second aperture dimension, and the second aperture dimension is greater than the first aperture dimension. The second Zernike expansion coefficient can be scaled relative to the first Zernike expansion coefficient using a scaling factor that includes a ratio of the second aperture dimension to the first aperture dimension raised to a power of a factor that includes a radial degree of the coefficient. Computer program products can also include a computer-readable medium for storing the codes. In some cases, the first aperture dimension includes a first aperture radius and the second aperture dimension includes a second aperture radius. In some cases, the optical system includes an optical tissue of a patient. In some cases, the first aperture dimension includes a first pupil dimension and the second aperture dimension includes a second pupil dimension. In some cases, the first pupil dimension includes a first pupil radius and the second pupil dimension includes a second pupil radius.

In some aspects, embodiments of the present invention encompass systems and methods for establishing a prescription that mitigates or treats a vision condition of an eye in a particular patient. Exemplary systems may include a first module having a tangible medium embodying machine-readable code that accepts a first geometrical configuration of the eye, a second module having a tangible medium embodying machine-readable code that determines an original set of coefficients for a basis function characterizing the first geometrical configuration, where the basis function can be separated into a product of a first set of radial polynomials and a first triangular function, a third module having a tangible medium embodying machine-readable code that accepts a second geometrical configuration of the eye, where a difference between the first geometrical configuration of the eye and the second geometrical configuration of the eye includes a pupil dilation, a fourth module having a tangible medium embodying machine-readable code that determines a transformed set of coefficients for the basis function, where the transformed set of coefficients are based on the first geometrical configuration of the eye, the original set of coefficients, and the second geometrical configuration of the eye, such that each coefficient of the transformed set of coefficients is based on a corresponding coefficient of the original set of coefficients and a corresponding polynomial, and a fifth module having a tangible medium embodying machine-readable code that derives the prescription for the particular patient based on the transformed set of coefficients, where the prescription mitigates or treats the vision condition of the eye. In some cases, a difference between the first geometrical configuration of the eye and the second geometrical configuration of the eye includes a pupil center shift. In some cases, a difference between the first geometrical configuration of the eye and the second geometrical configuration of the eye includes a cyclorotation. In some cases, the basis function includes a Zernike basis function. In some cases, the basis function includes a Taylor basis function. In some cases, the basis function includes a Seidel basis function.

In yet another aspect, embodiments of the present invention encompass systems and methods for establishing a prescription that mitigates or treats a vision condition of an eye in a particular patient. Exemplary methods may include inputting a first geometrical configuration of the eye, determining an original set of coefficients for a basis function characterizing the first geometrical configuration, where the basis function can be separated into a product of a first set of radial polynomials and a first triangular function, inputting a second geometrical configuration of the eye, where a difference between the first geometrical configuration of the eye and the second geometrical configuration of the eye includes a pupil dilation, and determining a transformed set of coefficients for the basis function, where the transformed set of coefficients are based on the first geometrical configuration of the eye, the original set of coefficients, and the second geometrical configuration of the eye, such that each coefficient of the transformed set of coefficients is based on a corresponding coefficient of the original set of coefficients and a corresponding polynomial. Methods may also include establishing the prescription for the particular patient based on the transformed set of coefficients, where the prescription mitigates or treats the vision condition of the eye. In some cases, a difference between the first geometrical configuration of the eye and the second geometrical configuration of the eye includes a pupil center shift. In some cases, a difference between the first geometrical configuration of the eye and the second geometrical configuration of the eye includes a cyclorotation. In some cases, the basis function includes a Zernike basis function. In some cases, the basis function includes a Taylor basis function. In some cases, the basis function includes a Seidel basis function.

In still another aspect, embodiments of the present invention encompass systems and methods for treating a particular patient with a prescription that mitigates or treats a vision condition of an eye of the patient. Exemplary methods may include obtaining a first wavefront map of the eye that corresponds to a first geometrical configuration of the eye in an evaluation context, where the first wavefront map is characterized by an original set of coefficients for a basis function that can be separated into a product of a first set of radial polynomials and a first triangular function, and determining a second wavefront map of the eye that corresponds to a second geometrical configuration of the eye in a treatment context, where a difference between the first geometrical configuration of the eye and the second geometrical configuration of the eye includes a pupil dilation, and where the second wavefront map is characterized by a transformed set of coefficients for the basis function that is based on the first geometrical configuration of the eye, the original set of coefficients, and the second geometrical configuration of the eye, such that each coefficient of the transformed set of coefficients is based on a corresponding coefficient of the original set of coefficients and a corresponding polynomial. Methods may also include establishing the prescription for the particular patient based on the transformed set of coefficients. Methods may also include treating the patient with the prescription to mitigate or treat the vision condition of the eye. In some cases, a difference between the first geometrical configuration of the eye and the second geometrical configuration of the eye includes a pupil center shift. In some cases, a difference between the first geometrical configuration of the eye and the second geometrical configuration of the eye includes a cyclorotation. In some cases, the basis function includes a Zernike basis function. In some cases, the basis function includes a Taylor basis function. In some cases, the basis function includes a Seidel basis function.

In still yet another aspect, embodiments of the present invention encompass systems and methods for treating a particular patient with a prescription that mitigates or treats a vision condition of an eye of the patient. Exemplary systems may include a first module that accepts a first wavefront map of the eye that corresponds to a first geometrical configuration of the eye in an evaluation context, where the first wavefront map is characterized by an original set of coefficients for a basis function that can be separated into a product of a first set of radial polynomials and a first triangular function, a second module that determines a second wavefront map of the eye that corresponds to a second geometrical configuration of the eye in a treatment context, where a difference between the first geometrical configuration of the eye and the second geometrical configuration of the eye includes a pupil dilation, and where the second wavefront map is characterized by a transformed set of coefficients for the basis function that is based on the first geometrical configuration of the eye, the original set of coefficients, and the second geometrical configuration of the eye, such that each coefficient of the transformed set of coefficients is based on a corresponding coefficient of the original set of coefficients and a corresponding polynomial, a third module that establishes the prescription for the particular patient based on the transformed set of coefficients, and a laser ablation system that modifies an optical tissue surface of the eye of the patient according to the prescription. In some cases, a difference between the first geometrical configuration of the eye and the second geometrical configuration of the eye includes a pupil center shift.

In some cases, a difference between the first geometrical configuration of the eye and the second geometrical configuration of the eye includes a cyclorotation. In some cases, the basis function includes a Zernike basis function. In some cases, the basis function includes a Taylor basis function. In some cases, the basis function includes a Seidel basis function.

In another aspect, embodiments of the present invention encompass computer program products for establishing a prescription that mitigates or treats a vision condition of an eye in a particular patient. Exemplary computer program products may include code for accepting a first geometrical configuration of the eye, code for determining an original set of coefficients for a basis function characterizing the first geometrical configuration, where the basis function can be separated into a product of a first set of radial polynomials and a first triangular function, code for accepting a second geometrical configuration of the eye, where a difference between the first geometrical configuration of the eye and the second geometrical configuration of the eye includes a pupil dilation, code for determining a transformed set of coefficients for the basis function, where the transformed set of coefficients are based on the first geometrical configuration of the eye, the original set of coefficients, and the second geometrical configuration of the eye, such that each coefficient of the transformed set of coefficients is based on a corresponding coefficient of the original set of coefficients and a corresponding polynomial, and code for establishing the prescription for the particular patient based on the transformed set of coefficients, where the prescription mitigates or treats the vision condition of the eye. In some cases, a difference between the first geometrical configuration of the eye and the second geometrical configuration of the eye includes a pupil center shift. In some cases, a difference between the first geometrical configuration of the eye and the second geometrical configuration of the eye includes a cyclorotation. In some cases, the basis function includes a Zernike basis function. In some cases, the basis function includes a Taylor basis function. In some cases, the basis function includes a Seidel basis function.

In yet another aspect, embodiments of the present invention encompass computer program products for treating a particular patient with a prescription that mitigates or treats a vision condition of an eye of the patient. Exemplary computer program products include code for accepting a first wavefront map of the eye that corresponds to a first geometrical configuration of the eye in an evaluation context, where the first wavefront map is characterized by an original set of coefficients for a basis function that can be separated into a product of a first set of radial polynomials and a first triangular function, code for determining a second wavefront map of the eye that corresponds to a second geometrical configuration of the eye in a treatment context, where a difference between the first geometrical configuration of the eye and the second geometrical configuration of the eye includes a pupil dilation, and where the second wavefront map is characterized by a transformed set of coefficients for the basis function that is based on the first geometrical configuration of the eye, the original set of coefficients, and the second geometrical configuration of the eye, such that each coefficient of the transformed set of coefficients is based on a corresponding coefficient of the original set of coefficients and a corresponding polynomial, code for establishing the prescription for the particular patient based on the transformed set of coefficients, and code for providing instructions to a laser ablation system to modify an optical tissue surface of the eye of the patient according to the prescription. In some cases, a difference between the first geometrical configuration of the eye and the second geometrical configuration of the eye includes a pupil center shift. In some cases, a difference between the first geometrical configuration of the eye and the second geometrical configuration of the eye includes a cyclorotation. In some cases, the basis function includes a Zernike basis function. In some cases, the basis function includes a Taylor basis function. In some cases, the basis function includes a Seidel basis function.

In another aspect, embodiments of the present invention encompass systems and methods of determining a high order aberration induced by a change in geometrical configuration in an eye of a patient. Exemplary methods may include inputting a first geometrical configuration of the eye, inputting an original set of coefficients for a basis function characterizing the first geometrical configuration of the eye, where the basis function can be separated into a product of a first set of radial polynomials and a first triangular function, inputting a second geometrical configuration of the eye, inputting a transformed set of coefficients for the basis function, where the transformed set of coefficients are based on the first geometrical configuration of the eye, the original set of coefficients, and the second geometrical configuration of the eye, and where a difference between the first geometrical configuration and the second geometrical configuration includes a pupil dilation, and determining the induced high order aberration based on the transformed set of coefficients. In some cases, a difference between the first geometrical configuration and the second geometrical configuration includes a pupil center shift. In some cases, a difference between the first geometrical configuration and the second geometrical configuration includes a cyclorotation and a pupil center shift. In some cases, the basis function includes a Zernike basis function. In some cases, the basis function includes a Taylor basis function. In some cases, the basis function includes a Seidel basis function. In some cases, the induced high order aberration includes coma, secondary coma, trefoil, primary spherical aberration, secondary spherical aberration, secondary astigmatism, or tertiary astigmatism. Exemplary methods may also include determining a predicted vision symptom based on the induced high order aberration. In some cases, the vision symptom includes a predicted night vision symptom. Exemplary methods may include determining a treatment based on the induced high order aberration. Some methods may include displaying the transformed set of coefficients for the basis function. Some methods may include displaying the induced high order aberration.

In yet another aspect, embodiments of the present invention encompass systems and methods for determining a high order aberration induced by a change in geometrical configuration in an eye of a patient. Exemplary systems may include a first module that accepts a first geometrical configuration of the eye, a second module that accepts an original set of coefficients for a basis function characterizing the first geometrical configuration of the eye, where the basis function can be separated into a product of a first set of radial polynomials and a first triangular function, a third module that accepts a second geometrical configuration of the eye, a fourth module that determines a transformed set of coefficients for the basis function, where the transformed set of coefficients are based on the first geometrical configuration of the eye, the original set of coefficients, and the second geometrical configuration of the eye, and where a difference between the first geometrical configuration and the second geometrical configuration includes a pupil dilation, and a fifth module that determines the induced high order aberration based on the transformed set of coefficients. In some cases, a difference between the first geometrical configuration and the second geometrical configuration includes a pupil center shift. In some cases, a difference between the first geometrical configuration and the second geometrical configuration includes a cyclorotation and a pupil center shift.

In another aspect, embodiments of the present invention encompass computer program products for determining a high order aberration induced by a change in geometrical configuration in an eye of a patient. Exemplary computer program products include code for accepting a first geometrical configuration of the eye, code for determining an original set of coefficients for a basis function characterizing the first geometrical configuration, where the basis function can be separated into a product of a first set of radial polynomials and a first triangular function, code for accepting a second geometrical configuration of the eye, code for determining a transformed set of coefficients for the basis function, where the transformed set of coefficients are based on the first geometrical configuration of the eye, the original set of coefficients, and the second geometrical configuration of the eye, and where a difference between the first geometrical configuration and the second geometrical configuration includes a pupil dilation, and code for determining the induced high order aberration based on the transformed set of coefficients. In some cases, computer program products can include code for determining a treatment based on the induced high order aberration. In some cases, computer program products can include code for displaying the transformed set of coefficients for the basis function.

In a further aspect, embodiments of the present invention encompass a system for establishing a prescription that mitigates or treats a vision condition of an eye in a particular patient. The system can include, for example, a first module having a tangible medium embodying machine-readable code that accepts a first geometrical configuration of the eye, a second module having a tangible medium embodying machine-readable code that determines an original set of coefficients for a basis function characterizing the first geometrical configuration. The basis function can be separated into a product of a first set of radial polynomials and a first triangular function. The system can also include a third module having a tangible medium embodying machine-readable code that accepts a second geometrical configuration of the eye, and a fourth module having a tangible medium embodying machine-readable code that determines a transformed set of coefficients for the basis function. The transformed set of coefficients can be based on the first geometrical configuration of the eye, the original set of coefficients, and the second geometrical configuration of the eye. The system can also include a fifth module having a tangible medium embodying machine-readable code that derives the prescription for the particular patient based on the transformed set of coefficients. The prescription may mitigate or treat the vision condition of the eye. In some cases, a difference between the first geometrical configuration of the eye and the second geometrical configuration of the eye is characterized by a pupil center shift. In some cases, a difference between the first geometrical configuration of the eye and the second geometrical configuration of the eye is characterized by a cyclorotation. In some cases, a difference between the first geometrical configuration of the eye and the second geometrical configuration of the eye is characterized by a pupil constriction or dilation. A basis function may include a Zernike basis function, a Taylor basis function, a Seidel basis function, or the like.

In another aspect, embodiments of the present invention provide methods for establishing a prescription that mitigates or treats a vision condition of an eye in a particular patient. An exemplary method includes inputting a first geometrical configuration of the eye, and determining an original set of coefficients for a basis function characterizing the first geometrical configuration, where the basis function can be separated into a product of a first set of radial polynomials and a first triangular function. The method can also include inputting a second geometrical configuration of the eye, and determining a transformed set of coefficients for the basis function, where the transformed set of coefficients are based on the first geometrical configuration of the eye, the original set of coefficients, and the second geometrical configuration of the eye. The method can also include establishing the prescription for the particular patient based on the transformed set of coefficients, where the prescription mitigates or treats the vision condition of the eye. In some cases, a difference between the first geometrical configuration of the eye and the second geometrical configuration of the eye is characterized by a pupil center shift. In some cases, a difference between the first geometrical configuration of the eye and the second geometrical configuration of the eye is characterized by a cyclorotation. In some cases, a difference between the first geometrical configuration of the eye and the second geometrical configuration of the eye is characterized by a pupil constriction or dilation. A basis function may include a Zernike basis function, a Taylor basis function, a Seidel basis function, or the like.

In another aspect, embodiments of the present invention encompass methods for treating a particular patient with a prescription that mitigates or treats a vision condition of an eye of the patient. For example, a method can include obtaining a first wavefront map of the eye that corresponds to a first geometrical configuration of the eye in an evaluation context, where the first wavefront map is characterized by an original set of coefficients for a basis function that can be separated into a product of a first set of radial polynomials and a first triangular function. The method can also include determining a second wavefront map of the eye that corresponds to a second geometrical configuration of the eye in a treatment context, where the second wavefront map is characterized by a transformed set of coefficients for the basis function that is based on the first geometrical configuration of the eye, the original set of coefficients, and the second geometrical configuration of the eye. Further, the method can include establishing the prescription for the particular patient based on the transformed set of coefficients, and treating the patient with the prescription to mitigate or treat the vision condition of the eye. In some cases, a difference between the first geometrical configuration of the eye and the second geometrical configuration of the eye is characterized by a pupil center shift. In some cases, a difference between the first geometrical configuration of the eye and the second geometrical configuration of the eye is characterized by a cyclorotation. In some cases, a difference between the first geometrical configuration of the eye and the second geometrical configuration of the eye is characterized by a pupil constriction or dilation. A basis function may include a Zernike basis function, a Taylor basis function, a Seidel basis function, or the like.

In still another aspect, embodiments of the present invention encompass systems and methods for determining a high order aberration induced by a change in geometrical configuration in an eye of a patient. Exemplary methods may include inputting a first geometrical configuration of the eye, and inputting an original set of coefficients for a basis function characterizing the first geometrical configuration of the eye. In some cases, the basis function can be separated into a product of a first set of radial polynomials and a first triangular function. Methods may also include inputting a second geometrical configuration of the eye, and inputting a transformed set of coefficients for the basis function. In some cases, the transformed set of coefficients are based on the first geometrical configuration of the eye, the original set of coefficients, and the second geometrical configuration of the eye. Methods may also include determining the induced high order aberration based on the transformed set of coefficients. According to some embodiments, a difference between the first geometrical configuration and the second geometrical configuration is related to or corresponds to a pupil center shift. According to some embodiments, a difference between the first geometrical configuration and the second geometrical configuration is related to or corresponds to a pupil constriction or a pupil dilation. According to some embodiments, a difference between the first geometrical configuration and the second geometrical configuration is related to or corresponds to a cyclorotation and a pupil center shift, a pupil constriction, or a pupil dilation. In some instances, the basis function includes a Zernike basis function. In some instances, the basis function includes a Taylor basis function. In some instances, the basis function includes a Seidel basis function. The induced high order aberration can include, for example, coma, secondary coma, trefoil, primary spherical aberration, secondary spherical aberration, secondary astigmatism, or tertiary astigmatism. Methods may also include determining a predicted vision symptom based on the induced high order aberration. In some cases, the vision symptom comprises a predicted night vision symptom. Optionally, methods may include determining a treatment based on the induced high order aberration. Methods may also include displaying the transformed set of coefficients for the basis function. In some cases, methods may include displaying the induced high order aberration.

In a further aspect, embodiments of the present invention encompass systems and methods for determining a high order aberration induced by a change in geometrical configuration in an eye of a patient. Exemplary systems may include a first module that accepts a first geometrical configuration of the eye, and a second module that accepts an original set of coefficients for a basis function characterizing the first geometrical configuration of the eye. In some cases, the basis function can be separated into a product of a first set of radial polynomials and a first triangular function. Systems may also include a third module that accepts a second geometrical configuration of the eye, and a fourth module that determines a transformed set of coefficients for the basis function. In some cases, the transformed set of coefficients are based on the first geometrical configuration of the eye, the original set of coefficients, and the second geometrical configuration of the eye. Systems may also include a fifth module that determines the induced high order aberration based on the transformed set of coefficients.

According to some system embodiments, a difference between the first geometrical configuration and the second geometrical configuration corresponds to a pupil center shift. According to some system embodiments, a difference between the first geometrical configuration and the second geometrical configuration corresponds to a pupil constriction or a pupil dilation. According to some system embodiments, a difference between the first geometrical configuration and the second geometrical configuration corresponds to a cyclorotation and a pupil center shift, a pupil constriction, or a pupil dilation.

In some aspects, embodiments of the present invention encompass computer program products for determining a high order aberration induced by a change in geometrical configuration in an eye of a patient. Exemplary computer program products may include code for accepting a first geometrical configuration of the eye, and code for determining an original set of coefficients for a basis function characterizing the first geometrical configuration. In some cases, the basis function can be separated into a product of a first set of radial polynomials and a first triangular function. Computer program products may also include code for accepting a second geometrical configuration of the eye, and code for determining a transformed set of coefficients for the basis function. In some cases, the transformed set of coefficients are based on the first geometrical configuration of the eye, the original set of coefficients, and the second geometrical configuration of the eye. Further, computer program products may include code for determining the induced high order aberration based on the transformed set of coefficients. In some instances, computer program products may include code for determining a treatment based on the induced high order aberration. In some instances, computer program products may include code for displaying the transformed set of coefficients for the basis function.

In another aspect, embodiments of the present invention provide a method of calculating a modified normalized Zernike expansion coefficient for an optical system. The method may include inputting an original normalized Zernike expansion coefficient for the optical system, where the original normalized Zernike expansion coefficient is associated with a first aperture dimension. The method may also include calculating a modified normalized Zernike expansion coefficient for the optical system, where the modified normalized Zernike expansion coefficient is associated with a second aperture dimension. In some cases, the modified normalized Zernike expansion coefficient can be calculated based on the original normalized Zernike expansion coefficient scaled by a scaling factor. The scaling factor can include a ratio of the second aperture dimension to the first aperture dimension, where the ratio raised to the power of a factor comprising a radial degree of the coefficient. In some cases, the aperture dimension includes an aperture radius. In some cases, the optical system include an optical tissue of a patient, and the aperture dimension includes a pupil dimension. In some cases, the pupil dimension includes a pupil radius. Optionally, the first aperture dimension may be greater than or smaller than the second aperture dimension.

In another aspect, embodiments of the present invention provide a method of determining an optical surface model for an optical tissue system of an eye. The method can include inputting a first optical data corresponding to the optical tissue system of the eye, where the first optical data includes a first set of normalized Zernike expansion coefficients corresponding to a first pupil radius of the eye. The method can also include calculating a second optical data corresponding to the optical tissue of the eye, where the second optical data includes a second set of normalized Zernike expansion coefficients corresponding to a second pupil radius of the eye. The second set of normalized Zernike expansion coefficient can be calculated based on the first set of normalized Zernike expansion coefficients scaled by a scaling factor. The scaling factor can include a ratio of the second aperture dimension to the first aperture dimension. The ratio can be raised to the power of a factor that includes a radial degree of the coefficient. The method can further include determining the optical surface model based on the second optical data. Optionally, the first pupil radius of the eye can be greater than or smaller than the second pupil radius of the eye.

In another aspect, embodiments of the present invention provide a system for calculating a modified normalized Zernike expansion coefficient for an optical system. The system can include, for example, means for inputting an original normalized Zernike expansion coefficient for the optical system, where the original normalized Zernike expansion coefficient is associated with a first aperture dimension. The system can also include means for calculating a modified normalized Zernike expansion coefficient for the optical system, where the modified normalized Zernike expansion coefficient is associated with a second aperture dimension. The modified normalized Zernike expansion coefficient can be calculated based on the original normalized Zernike expansion coefficient scaled by a scaling factor. The scaling factor can include a ratio of the second aperture dimension to the first aperture dimension, where the ratio raised to the power of a factor comprising a radial degree of the coefficient. The aperture dimension can include an aperture radius. In some cases, the optical system includes an optical tissue of a patient, and the aperture dimension includes a pupil dimension. Optionally, the pupil dimension may include a pupil radius. In some cases, the first aperture dimension is greater than or smaller than the second aperture dimension.

In another aspect, embodiments of the present invention provide a method of calculating effective powers of an optical system. The method can include, for example, calculating a first effective power using a first Zernike expansion coefficient for the optical system, where the first Zernike expansion coefficient is associated with a first aperture dimension. The method can also include calculating a second effective power using a second Zernike expansion coefficient for the optical system, where the second Zernike expansion coefficient is associated with a second aperture dimension. The second Zernike expansion coefficient can be scaled relative to the first Zernike expansion coefficient using a scaling factor that includes a ratio of the second aperture dimension to the first aperture dimension raised to a power of a factor that includes a radial degree of the coefficient. In some cases, the optical system includes an optical tissue of a patient, and the aperture dimension includes a pupil dimension. In some cases, the pupil dimension includes a pupil radius.

In another aspect, embodiments of the present invention provide a system for calculating effective power for an optical system. The system can include means for inputting a first Zernike expansion coefficient for the optical system, where the first Zernike expansion coefficient is associated with a first aperture dimension. The system can also include means for calculating a second effective power using a second Zernike expansion coefficient for the optical system, where the second Zernike expansion coefficient is associated with a second aperture dimension and scaled relative to the first Zernike expansion coefficient using a scaling factor that includes a ratio of the second aperture dimension to the first aperture dimension raised to a power of a factor that includes a radial degree of the coefficient. In some cases, the optical system includes an optical tissue of a patient, and the aperture dimension includes a pupil dimension. In some cases, the pupil dimension includes a pupil radius.

In a further aspect, embodiments of the present invention provide a computer program product for determining an optical surface model for an optical tissue system of an eye. The computer program product can include, for example, code for accepting a first optical data corresponding to the optical tissue system of the eye, where the first optical data includes a first set of normalized Zernike expansion coefficients corresponding to a first pupil radius of the eye. The product can also include code for calculating a second optical data corresponding to the optical tissue of the eye, where the second optical data includes a second set of normalized Zernike expansion coefficients corresponding to a second pupil radius of the eye. According to code, the second set of normalized Zernike expansion coefficient can be calculated based on the first set of normalized Zernike expansion coefficients scaled by a scaling factor. The scaling factor can include a ratio of the second aperture dimension to the first aperture dimension, and the ratio can be raised to the power of a factor comprising a radial degree of the coefficient. the product can also include code for determining the optical surface model based on the second optical data. Optionally, the product includes a computer-readable medium for storing the codes. In some cases, the optical system includes an optical tissue of a patient, and the aperture dimension includes a pupil dimension.

For a fuller understanding of the nature and advantages of the present invention, reference should be had to the ensuing detailed description taken in conjunction with the accompanying drawings.

BRIEF DESCRIPTION OF THE DRAWINGS

FIGS. 11A and 11B show illustrations of wavefront maps for a human eye, according to embodiments of the present invention.

FIGS. 12A to 12C show degrees of freedom for rotational eye movements, according to embodiments of the present invention.

FIG. 13 depicts coordinates before and after a cyclorotation, according to embodiments of the present invention.

FIGS. 14A to 14D show illustrations of wavefront maps for a human eye, according to embodiments of the present invention.

FIGS. 15A to 15H show illustrations of wavefront contour maps for a human eye, according to embodiments of the present invention.

FIGS. 16A to 16G show illustrations of point spread functions and corresponding simulated images, according to embodiments of the present invention.

FIGS. 19A to 19H show illustrations of wavefront contour maps for a human eye, according to embodiments of the present invention.

FIGS. 20A to 20G show illustrations of point spread functions and corresponding simulated images, according to embodiments of the present invention.

FIGS. 21A and 21B show illustrations of wavefront contour maps for a human eye, according to embodiments of the present invention.

FIGS. 22A to 22D show illustrations of wavefront contour maps for a human eye, according to embodiments of the present invention.

DETAILED DESCRIPTION OF THE INVENTION

Figure 1:
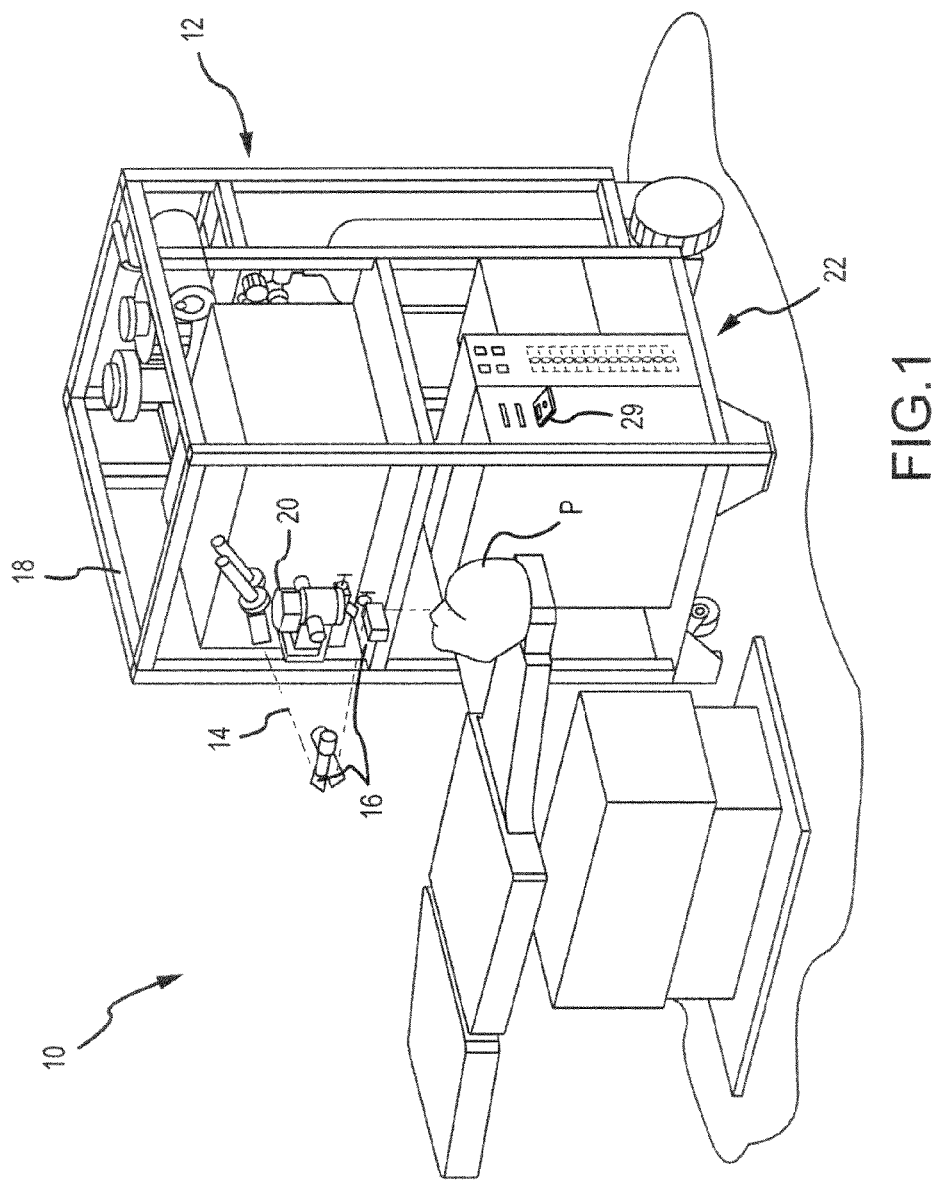
FIG. 1 illustrates a laser ablation system according to embodiments of the present invention.

Embodiments of the present invention encompass techniques for wavefront transformation and iris registration, wavefront representation for pupil resizing, wavefront representation for cyclorotation, and wavefront representation for decentration. Related examples and derivations are also provided. Pupil resizing approaches encompass Taylor resizing monomials, Zernike resizing polynomials, and pupil resizing with Seidel series. Pupil resizing techniques can also involve effective power and the treatment of presbyopia. Cyclorotation approaches encompass wavefront rotation with Taylor monomials and Zernike polynomials. Decentration approaches encompass wavefront extrapolation, wavefront decentration with Taylor monomials and Zernike polynomials, and wavefront refraction of decentered aberrations. Wavefront representation techniques can also involve wavefront transformation and subsequent refraction. Embodiments disclosed herein provide refraction calculation formulas for various cases of geometrical transformations, including rotation, decentration, and constriction.

Embodiments of the present invention provide techniques for rescaling polynomials that correspond to a patient pupil, and encompass methods and systems for calculating Zernike resizing polynomials and for deriving scaling for Taylor, Seidel, and other basis functions. In some cases, the present techniques involve a nonrecursive approach. In some cases, the present techniques involve an analytical based approach for determining ocular aberrations and refractive treatments. Embodiments disclosed herein provide techniques for establishing pupil resizing polynomials for various basis functions. For example, in the situation where an eye presents a wavefront and the pupil of the eye constricts, it is possible to define a circle with a radius that corresponds to the constricted pupil, and to define an aberration pattern that corresponds to the circle. In some cases, the normalized radius is constricted or contracted. An epsilon as a ratio can be established that represents a ratio of the new smaller pupil radius to the original pupil radius. In the original wavefront, the part that is within the boundary when the normalized pupil is epsilon describes the wavefront that is to be constricted. It is possible to equate that part of the wavefront to a wavefront represented within the constricted pupil to obtain a representation of a generic formula. Hence, from the definition of polynomials it is possible to obtain a pupil scaling factor epsilon and pupil radius rho. For polynomials that can be separated into radial polynomials and angular component, it is possible ignore the angular component and assume the constriction is concentric. Hence, it is possible to determine a generic pupil rescaling formula (GPRF) for any basis function that can be separated into radial polynomials and a triangular function. In some cases, the GPRF can be defined as the product of a pupil rescaling/resizing polynomial factor, and a radial polynomial, where the radial polynomial is determined prior to resizing. Embodiments of the present invention provide pupil resizing polynomials for Zernike basis functions, Taylor basis functions, Seidel basis functions, and the like, and methods and system for obtaining such pupil resizing polynomials and for using the same for resizing purposes. Embodiments also encompass methods and systems for calculating or determining refractions based on a new set of polynomials, after a geometrical transformation such as a pupil constriction, a rotations, or a decentration.

The present invention can be readily adapted for use with existing laser systems, wavefront measurement systems, and other optical measurement devices. Although the systems, software, and methods of the present invention are described primarily in the context of a laser eye surgery system, it should be understood the present invention may be adapted for use in alternative eye treatment procedures, systems, or modalities, such as spectacle lenses, intraocular lenses, accommodating IOLs, contact lenses, corneal ring implants, collagenous corneal tissue thermal remodeling, corneal inlays, corneal onlays, other corneal implants or grafts, and the like. Relatedly, systems, software, and methods according to embodiments of the present invention are well suited for customizing any of these treatment modalities to a specific patient. Thus, for example, embodiments encompass custom intraocular lenses, custom contact lenses, custom corneal implants, and the like, which can be configured to treat or ameliorate any of a variety of vision conditions in a particular patient based on their unique ocular characteristics or anatomy.

Turning now to the drawings, FIG. 1 illustrates a laser eye surgery system 10 of the present invention, including a laser 12 that produces a laser beam 14. Laser 12 is optically coupled to laser delivery optics 16, which directs laser beam 14 to an eye E of patient P. A delivery optics support structure (not shown here for clarity) extends from a frame 18 supporting laser 12. A microscope 20 is mounted on the delivery optics support structure, the microscope often being used to image a cornea of eye E.

Laser 12 generally comprises an excimer laser, ideally comprising an argon-fluorine laser producing pulses of laser light having a wavelength of approximately 193 nm. Laser 12 will preferably be designed to provide a feedback stabilized fluence at the patient's eye, delivered via delivery optics 16. The present invention may also be useful with alternative sources of ultraviolet or infrared radiation, particularly those adapted to controllably ablate the corneal tissue without causing significant damage to adjacent and/or underlying tissues of the eye. Such sources include, but are not limited to, solid state lasers and other devices which can generate energy in the ultraviolet wavelength between about 185 and 205 nm and/or those which utilize frequency-multiplying techniques. Hence, although an excimer laser is the illustrative source of an ablating beam, other lasers may be used in the present invention.

Laser system 10 will generally include a computer or programmable processor 22. Processor 22 may comprise (or interface with) a conventional PC system including the standard user interface devices such as a keyboard, a display monitor, and the like. Processor 22 will typically include an input device such as a magnetic or optical disk drive, an internet connection, or the like. Such input devices will often be used to download a computer executable code from a tangible storage media 29 embodying any of the methods of the present invention. Tangible storage media 29 may take the form of a floppy disk, an optical disk, a data tape, a volatile or non-volatile memory, RAM, or the like, and the processor 22 will include the memory boards and other standard components of modern computer systems for storing and executing this code. Tangible storage media 29 may optionally embody wavefront sensor data, wavefront gradients, a wavefront elevation map, a treatment map, a corneal elevation map, and/or an ablation table. While tangible storage media 29 will often be used directly in cooperation with a input device of processor 22, the storage media may also be remotely operatively coupled with processor by means of network connections such as the internet, and by wireless methods such as infrared, Bluetooth, or the like.

Laser 12 and delivery optics 16 will generally direct laser beam 14 to the eye of patient P under the direction of a computer 22. Computer 22 will often selectively adjust laser beam 14 to expose portions of the cornea to the pulses of laser energy so as to effect a predetermined sculpting of the cornea and alter the refractive characteristics of the eye. In many embodiments, both laser beam 14 and the laser delivery optical system 16 will be under computer control of processor 22 to effect the desired laser sculpting process, with the processor effecting (and optionally modifying) the pattern of laser pulses. The pattern of pulses may by summarized in machine readable data of tangible storage media 29 in the form of a treatment table, and the treatment table may be adjusted according to feedback input into processor 22 from an automated image analysis system in response to feedback data provided from an ablation monitoring system feedback system. Optionally, the feedback may be manually entered into the processor by a system operator. Such feedback might be provided by integrating the wavefront measurement system described below with the laser treatment system 10, and processor 22 may continue and/or terminate a sculpting treatment in response to the feedback, and may optionally also modify the planned sculpting based at least in part on the feedback. Measurement systems are further described in U.S. Pat. No. 6,315,413, the full disclosure of which is incorporated herein by reference.

Laser beam 14 may be adjusted to produce the desired sculpting using a variety of alternative mechanisms. The laser beam 14 may be selectively limited using one or more variable apertures. An exemplary variable aperture system having a variable iris and a variable width slit is described in U.S. Pat. No. 5,713,892, the full disclosure of which is incorporated herein by reference. The laser beam may also be tailored by varying the size and offset of the laser spot from an axis of the eye, as described in U.S. Pat. Nos. 5,683,379, 6,203,539, and 6,331,177, the full disclosures of which are incorporated herein by reference.

Still further alternatives are possible, including scanning of the laser beam over the surface of the eye and controlling the number of pulses and/or dwell time at each location, as described, for example, by U.S. Pat. No. 4,665,913, the full disclosure of which is incorporated herein by reference; using masks in the optical path of laser beam 14 which ablate to vary the profile of the beam incident on the cornea, as described in U.S. Pat. No. 5,807,379, the full disclosure of which is incorporated herein by reference; hybrid profile-scanning systems in which a variable size beam (typically controlled by a variable width slit and/or variable diameter iris diaphragm) is scanned across the cornea; or the like. The computer programs and control methodology for these laser pattern tailoring techniques are well described in the patent literature.

Additional components and subsystems may be included with laser system 10, as should be understood by those of skill in the art. For example, spatial and/or temporal integrators may be included to control the distribution of energy within the laser beam, as described in U.S. Pat. No. 5,646,791, the full disclosure of which is incorporated herein by reference. Ablation effluent evacuators/filters, aspirators, and other ancillary components of the laser surgery system are known in the art. Further details of suitable systems for performing a laser ablation procedure can be found in commonly assigned U.S. Pat. Nos. 4,665,913, 4,669,466, 4,732,148, 4,770,172, 4,773,414, 5,207,668, 5,108,388, 5,219,343, 5,646,791 and 5,163,934, the complete disclosures of which are incorporated herein by reference. Suitable systems also include commercially available refractive laser systems such as those manufactured and/or sold by Alcon, Bausch & Lomb, Nidek, WaveLight, LaserSight, Schwind, Zeiss-Meditec, and the like. Basis data can be further characterized for particular lasers or operating conditions, by taking into account localized environmental variables such as temperature, humidity, airflow, and aspiration.

Figure 2:
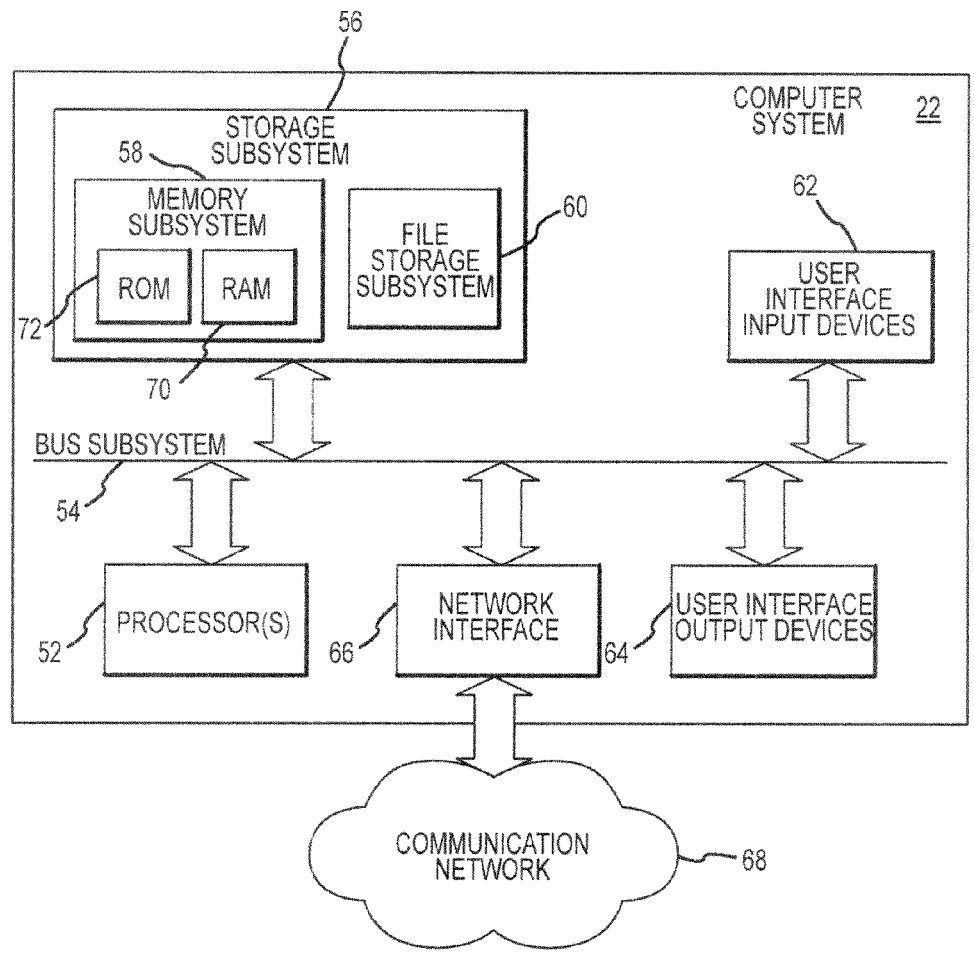
FIG. 2 illustrates a simplified computer system according to embodiments of the present invention.

FIG. 2 is a simplified block diagram of an exemplary computer system 22 that may be used by the laser surgical system 10 of the present invention. Computer system 22 typically includes at least one processor 52 which may communicate with a number of peripheral devices via a bus subsystem 54. These peripheral devices may include a storage subsystem 56, comprising a memory subsystem 58 and a file storage subsystem 60, user interface input devices 62, user interface output devices 64, and a network interface subsystem 66. Network interface subsystem 66 provides an interface to outside networks 68 and/or other devices, such as the wavefront measurement system 30.

User interface input devices 62 may include a keyboard, pointing devices such as a mouse, trackball, touch pad, or graphics tablet, a scanner, foot pedals, a joystick, a touchscreen incorporated into the display, audio input devices such as voice recognition systems, microphones, and other types of input devices. User input devices 62 will often be used to download a computer executable code from a tangible storage media 29 embodying any of the methods of the present invention. In general, use of the term "input device" is intended to include a variety of conventional and proprietary devices and ways to input information into computer system 22.

User interface output devices 64 may include a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide a non-visual display such as via audio output devices. In general, use of the term "output device" is intended to include a variety of conventional and proprietary devices and ways to output information from computer system 22 to a user.

Storage subsystem 56 can store the basic programming and data constructs that provide the functionality of the various embodiments of the present invention. For example, a database and modules implementing the functionality of the methods of the present invention, as described herein, may be stored in storage subsystem 56. These software modules are generally executed by processor 52. In a distributed environment, the software modules may be stored on a plurality of computer systems and executed by processors of the plurality of computer systems. Storage subsystem 56 typically comprises memory subsystem 58 and file storage subsystem 60.

Memory subsystem 58 typically includes a number of memories including a main random access memory (RAM) 70 for storage of instructions and data during program execution and a read only memory (ROM) 72 in which fixed instructions are stored. File storage subsystem 60 provides persistent (non-volatile) storage for program and data files, and may include tangible storage media 29 (FIG. 1) which may optionally embody wavefront sensor data, wavefront gradients, a wavefront elevation map, a treatment map, and/or an ablation table. File storage subsystem 60 may include a hard disk drive, a floppy disk drive along with associated removable media, a Compact Digital Read Only Memory (CD-ROM) drive, an optical drive, DVD, CD-R, CD-RW, solid-state removable memory, and/or other removable media cartridges or disks. One or more of the drives may be located at remote locations on other connected computers at other sites coupled to computer system 22. The modules implementing the functionality of the present invention may be stored by file storage subsystem 60.

Bus subsystem 54 provides a mechanism for letting the various components and subsystems of computer system 22 communicate with each other as intended. The various subsystems and components of computer system 22 need not be at the same physical location but may be distributed at various locations within a distributed network. Although bus subsystem 54 is shown schematically as a single bus, alternate embodiments of the bus subsystem may utilize multiple busses.

Computer system 22 itself can be of varying types including a personal computer, a portable computer, a workstation, a computer terminal, a network computer, a control system in a wavefront measurement system or laser surgical system, a mainframe, or any other data processing system. Due to the ever-changing nature of computers and networks, the description of computer system 22 depicted in FIG. 2 is intended only as a specific example for purposes of illustrating one embodiment of the present invention. Many other configurations of computer system 22 are possible having more or less components than the computer system depicted in FIG. 2.

Figure 3:
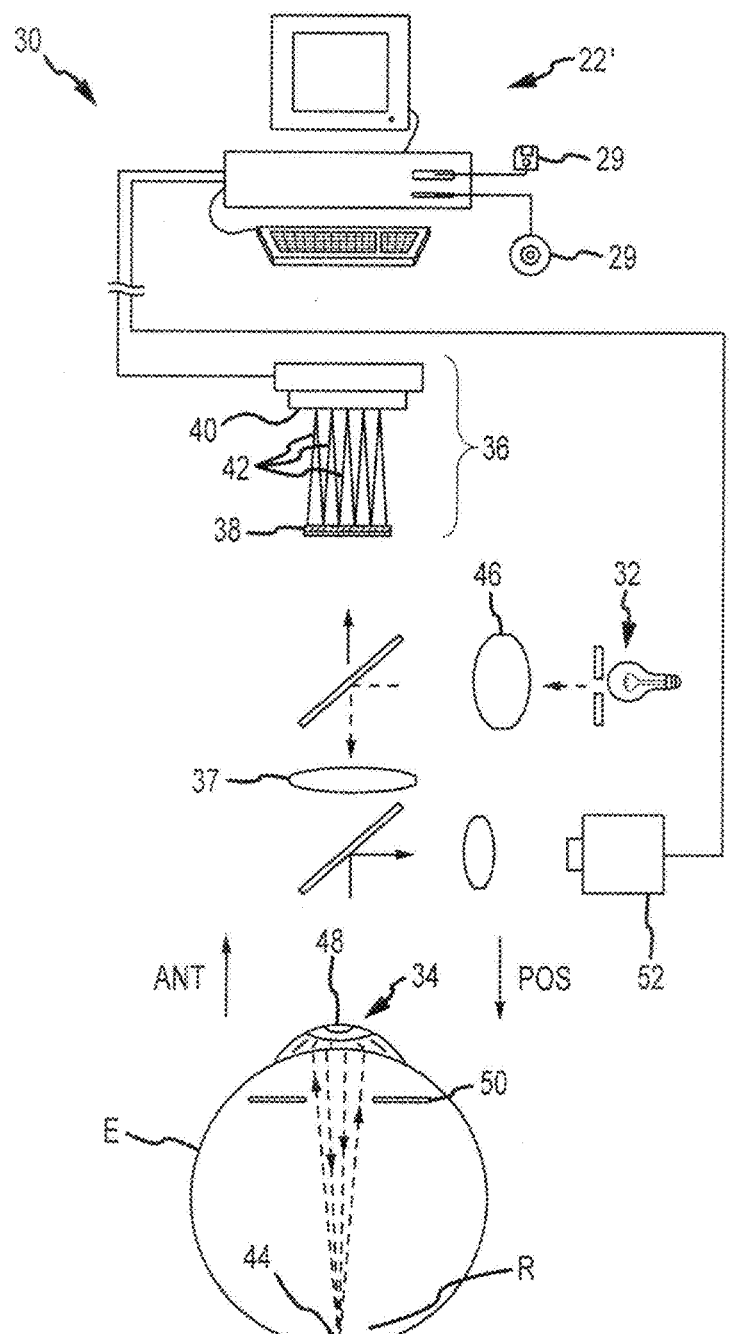
FIG. 3 illustrates a wavefront measurement system according to embodiments of the present invention.

Referring now to FIG. 3, one embodiment of a wavefront measurement system 30 is schematically illustrated in simplified form. In very general terms, wavefront measurement system 30 is configured to sense local slopes of a gradient map exiting the patient's eye. Devices based on the Hartmann-Shack principle generally include a lenslet array to sample the gradient map uniformly over an aperture, which is typically the exit pupil of the eye. Thereafter, the local slopes of the gradient map are analyzed so as to reconstruct the wavefront surface or map.

More specifically, one wavefront measurement system 30 includes an image source 32, such as a laser, which projects a source image through optical tissues 34 of eye E so as to form an image 44 upon a surface of retina R. The image from retina R is transmitted by the optical system of the eye (e.g., optical tissues 34) and imaged onto a wavefront sensor 36 by system optics 37. The wavefront sensor 36 communicates signals to a computer system 22' for measurement of the optical errors in the optical tissues 34 and/or determination of an optical tissue ablation treatment program. Computer 22' may include the same or similar hardware as the computer system 22 illustrated in FIGS. 1 and 2. Computer system 22' may be in communication with computer system 22 that directs the laser surgery system 10, or some or all of the components of computer system 22, 22' of the wavefront measurement system 30 and laser surgery system 10 may be combined or separate. If desired, data from wavefront sensor 36 may be transmitted to a laser computer system 22 via tangible media 29, via an I/O port, via an networking connection 66 such as an intranet or the Internet, or the like.

Wavefront sensor 36 generally comprises a lenslet array 38 and an image sensor 40. As the image from retina R is transmitted through optical tissues 34 and imaged onto a surface of image sensor 40 and an image of the eye pupil P is similarly imaged onto a surface of lenslet array 38, the lenslet array separates the transmitted image into an array of beamlets 42, and (in combination with other optical components of the system) images the separated beamlets on the surface of sensor 40. Sensor 40 typically comprises a charged couple device or "CCD," and senses the characteristics of these individual beamlets, which can be used to determine the characteristics of an associated region of optical tissues 34. In particular, where image 44 comprises a point or small spot of light, a location of the transmitted spot as imaged by a beamlet can directly indicate a local gradient of the associated region of optical tissue.

Eye E generally defines an anterior orientation ANT and a posterior orientation POS. Image source 32 generally projects an image in a posterior orientation through optical tissues 34 onto retina R as indicated in FIG. 3. Optical tissues 34 again transmit image 44 from the retina anteriorly toward wavefront sensor 36. Image 44 actually formed on retina R may be distorted by any imperfections in the eye's optical system when the image source is originally transmitted by optical tissues 34. Optionally, image source projection optics 46 may be configured or adapted to decrease any distortion of image 44.

In some embodiments, image source optics 46 may decrease lower order optical errors by compensating for spherical and/or cylindrical errors of optical tissues 34. Higher order optical errors of the optical tissues may also be compensated through the use of an adaptive optic element, such as a deformable mirror (described below). Use of an image source 32 selected to define a point or small spot at image 44 upon retina R may facilitate the analysis of the data provided by wavefront sensor 36. Distortion of image 44 may be limited by transmitting a source image through a central region 48 of optical tissues 34 which is smaller than a pupil 50, as the central portion of the pupil may be less prone to optical errors than the peripheral portion. Regardless of the particular image source structure, it will be generally be beneficial to have a well-defined and accurately formed image 44 on retina R.

In one embodiment, the wavefront data may be stored in a computer readable medium 29 or a memory of the wavefront sensor system 30 in two separate arrays containing the x and y wavefront gradient values obtained from image spot analysis of the Hartmann-Shack sensor images, plus the x and y pupil center offsets from the nominal center of the Hartmann-Shack lenslet array, as measured by the pupil camera 51 (FIG. 3) image. Such information contains all the available information on the wavefront error of the eye and is sufficient to reconstruct the wavefront or any portion of it. In such embodiments, there is no need to reprocess the Hartmann-Shack image more than once, and the data space required to store the gradient array is not large. For example, to accommodate an image of a pupil with an 8 mm diameter, an array of a 20×20 size (i.e., 400 elements) is often sufficient. As can be appreciated, in other embodiments, the wavefront data may be stored in a memory of the wavefront sensor system in a single array or multiple arrays.

While the methods of the present invention will generally be described with reference to sensing of an image 44, a series of wavefront sensor data readings may be taken. For example, a time series of wavefront data readings may help to provide a more accurate overall determination of the ocular tissue aberrations. As the ocular tissues can vary in shape over a brief period of time, a plurality of temporally separated wavefront sensor measurements can avoid relying on a single snapshot of the optical characteristics as the basis for a refractive correcting procedure. Still further alternatives are also available, including taking wavefront sensor data of the eye with the eye in differing configurations, positions, and/or orientations. For example, a patient will often help maintain alignment of the eye with wavefront measurement system 30 by focusing on a fixation target, as described in U.S. Pat. No. 6,004,313, the full disclosure of which is incorporated herein by reference. By varying a position of the fixation target as described in that reference, optical characteristics of the eye may be determined while the eye accommodates or adapts to image a field of view at a varying distance and/or angles.

The location of the optical axis of the eye may be verified by reference to the data provided from a pupil camera 52. In the exemplary embodiment, a pupil camera 52 images pupil 50 so as to determine a position of the pupil for registration of the wavefront sensor data relative to the optical tissues.

Figure 3A:
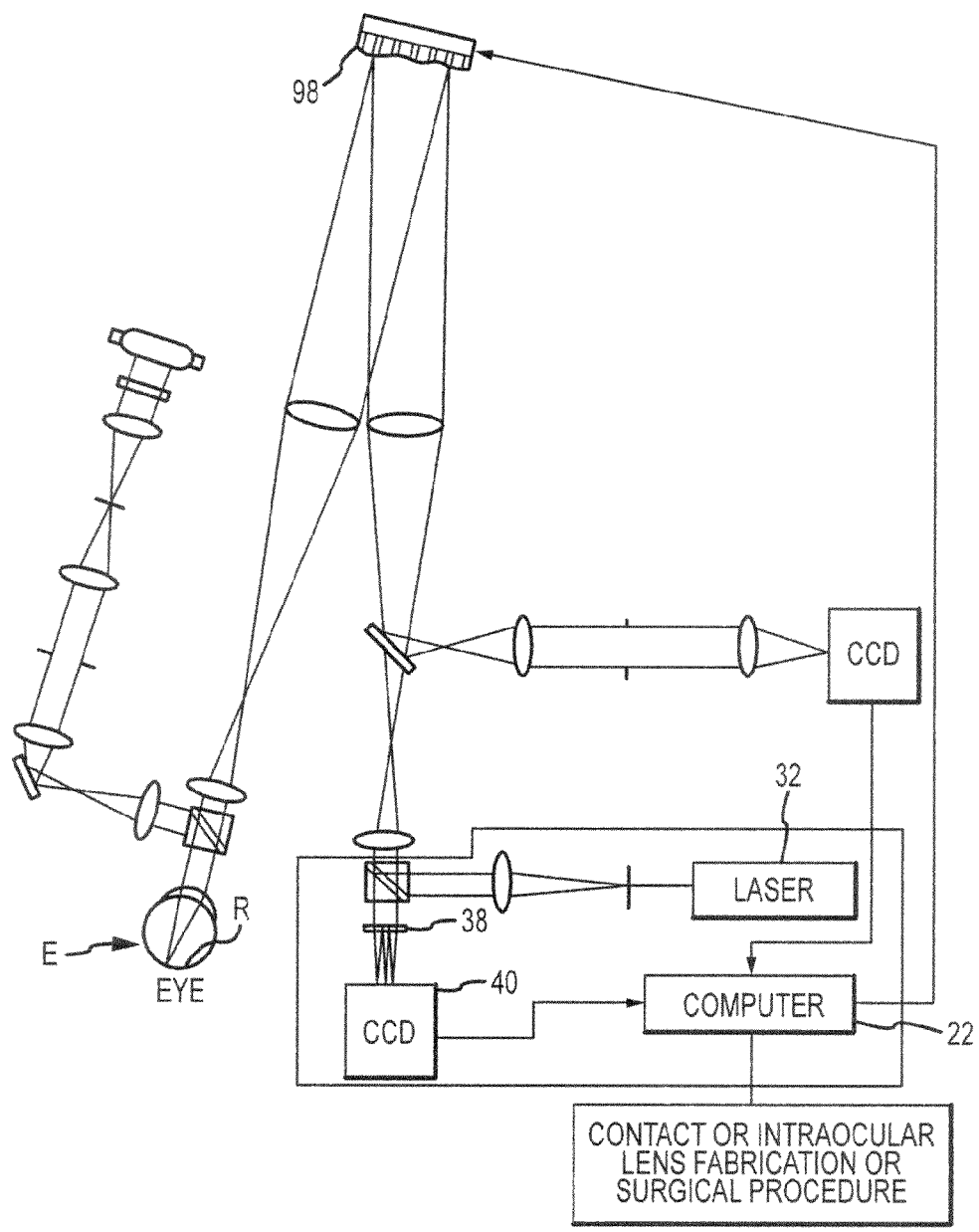
FIG. 3A illustrates another wavefront measurement system according to embodiments of the present invention.

An alternative embodiment of a wavefront measurement system is illustrated in FIG. 3A. The major components of the system of FIG. 3A are similar to those of FIG. 3. Additionally, FIG. 3A includes an adaptive optical element 53 in the form of a deformable mirror. The source image is reflected from deformable mirror 98 during transmission to retina R, and the deformable mirror is also along the optical path used to form the transmitted image between retina R and imaging sensor 40. Deformable mirror 98 can be controllably deformed by computer system 22 to limit distortion of the image formed on the retina or of subsequent images formed of the images formed on the retina, and may enhance the accuracy of the resultant wavefront data. The structure and use of the system of FIG. 3A are more fully described in U.S. Pat. No. 6,095,651, the full disclosure of which is incorporated herein by reference.

The components of an embodiment of a wavefront measurement system for measuring the eye and ablations may comprise elements of a WaveScan® system, available from VISX, INCORPORATED of Santa Clara, Calif. One embodiment includes a WaveScan system with a deformable mirror as described above. An alternate embodiment of a wavefront measuring system is described in U.S. Pat. No. 6,271,915, the full disclosure of which is incorporated herein by reference. It is appreciated that any wavefront aberrometer could be employed for use with the present invention. Relatedly, embodiments of the present invention encompass the implementation of any of a variety of optical instruments provided by WaveFront Sciences, Inc., including the COAS wavefront aberrometer, the ClearWave contact lens aberrometer, the CrystalWave IOL aberrometer, and the like. Embodiments of the present invention may also involve wavefront measurement schemes such as a Tscherning-based system, which may be provided by WaveFront Sciences, Inc. Embodiments of the present invention may also involve wavefront measurement schemes such as a ray tracing-based system, which may be provided by Tracey Technologies, Corp.

Ocular wavefront transformation is suitable for use in wavefront optics for vision correction because the pupil size of a human eye often changes due to accommodation or the change of lighting, and because the pupil constriction is commonly not concentric. Certain features of these ocular effects are discussed in, for example, Wilson, M. A. et al., *Optom. Vis. Sci.*, 69:129-136 (1992), Yang, Y. et al., *Invest. Ophthal. Vis. Sci.*, 43:2508-2512 (2002), and Donnenfeld, E. J., *Refract. Surg.*, 20:593-596 (2004). For example, in laser vision correction, the pupil size of an eye is relatively large when an ocular wavefront is captured under an aberrometer. To obtain the entire ocular wavefront, it is often recommended that the ambient light be kept low so as to dilate the pupil size during the wavefront exam. A larger wavefront map can provide surgeons the flexibility for treatment over a smaller zone, because the wavefront information over any smaller zone within a larger zone is known. When a smaller wavefront map is captured, however, it is also useful to devise an accurate treatment over a larger zone. When the patient is under the laser, the pupil size can change due to changes in the ambient light. In many cases, the surgery room is brighter than a wavefront examination room, in particular when the patient is under the hood. Furthermore, the cyclorotation of the eye due to the change from a sitting position to a laying position can make the pupil center change between the wavefront capture and the laser ablation, for example as discussed in Chernyak, D. A., *J. Cataract. Refract. Surg.*, 30:633-638 (2004). Theoretically, it has been reported that correction of error due to rotation and translation of the pupil can provide significant benefits in vision correction. Certain aspects of these ocular effects are discussed in Bará, S. et al., *Appl. Opt.*, 39:3413-3420 (2000) and Guirao, A. et al., *J. Opt. Soc. Am. A*, 18:1003-1015 (2001).

Figure 3B:
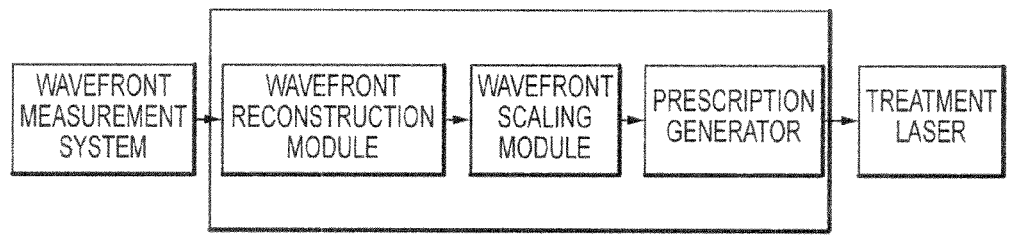
FIG. 3B is a schematic block diagram illustrating software and/or hardware modules which may be included in the computer system of FIG. 2 for use in embodiments of the invention.
Figure 3C:
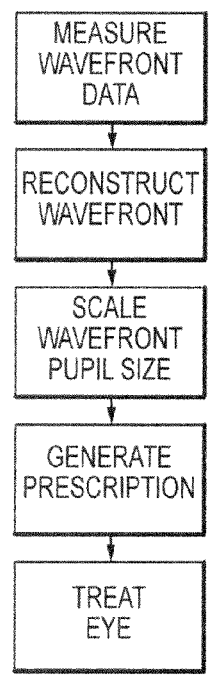
FIG. 3C is a flowchart schematically illustrating an embodiment of a method of the invention.

FIGS. 3B and 3C schematically illustrate embodiments of hardware and/or software modules of computer system 22 and a related method, respectively. These embodiments can generate scaled wavefront reconstruction data suitable for analysis of a patient's eye when a pupil of the patient changes size from a relatively large wavefront measurement pupil size to a smaller size or from a relatively small wavefront measurement pupil size to a larger size. Structures and methods for reconstructing a wavefront and/or generating prescriptions from wavefront data are well documented in a variety of patent literature, including U.S. patent application Ser. Nos. 10/738,358, as filed on Dec. 5, 2003 and entitled "Presbyopia Correction Using Patient Data;" and 11/134,630, as filed on May 19, 2005 and entitled "Residual Accommodation Threshold for Correction of Presbyopia and Other Presbyopia Correction Using Patient Data," the full disclosures of which are incorporated herein by reference. The following description will address scaling of the wavefront data, particularly scaling of Zernike polynomial expansion coefficients of a wavefront so as to accommodate or model constriction or dilation of the pupil of the patient when viewing objects under different lighting conditions, differing viewing distances, and the like.

If $W(Rr, \theta)$ represents the ocular aberrations of a human eye measured as the optical path difference, the wavefront can be decomposed into a set of complete and orthogonal basis functions as:

$$W(Rr, \theta) = \sum_{i=0}^{\infty} a_i F_i(r, \theta), \quad \text{(Eq. 1A)}$$

where $a_i$ is the coefficient of the ith basis function $F_i(r, \theta)$ and R is the pupil radius. Here, r is the radial variable in the polar coordinates defining the unit circle. Zernike polynomials have been widely used as a set of basis functions because of their connection to classical aberrations in optical systems with circular apertures.

The normalized Zernike polynomials may be defined as:

$$Z_i(r,\theta) = R_n^{\{|m|\}}(r)\theta^m(\theta) \quad \text{(Eq. 2A)}$$

where n and m denote the radial degree and the azimuthal frequency, respectively; the radial polynomials are defined as:

$$R_n^{\{|m|\}}(r) = \sum_{s=0}^{(n-|m|)/2} \frac{(-1)^s \sqrt{n+1}\,(n-s)!}{s![(n+m)/2-s]![(n-m)/2-s]!} r^{n-2s} \quad \text{(Eq. 3A)}$$

and the triangular functions as:

$$\theta^m(\theta) = \begin{cases} \sqrt{2}\cos|m|\theta & (m>0) \\ 1 & (m=0) \\ \sqrt{2}\sin|m|\theta & (m<0) \end{cases} \quad \text{(Eq. 4A)}$$

Both the single-index i and the double-index m and n may be referred to herein. These two different indexing schemes can be effectively identical. For example, the decision whether to use a single or double index may be based on convenience.

It can be usefully assumed that (1) the optical properties of the human eye do not change when the pupil constricts or dilates and (2) the constriction or dilation of the pupil is concentric.

Figures 3D, 3E:
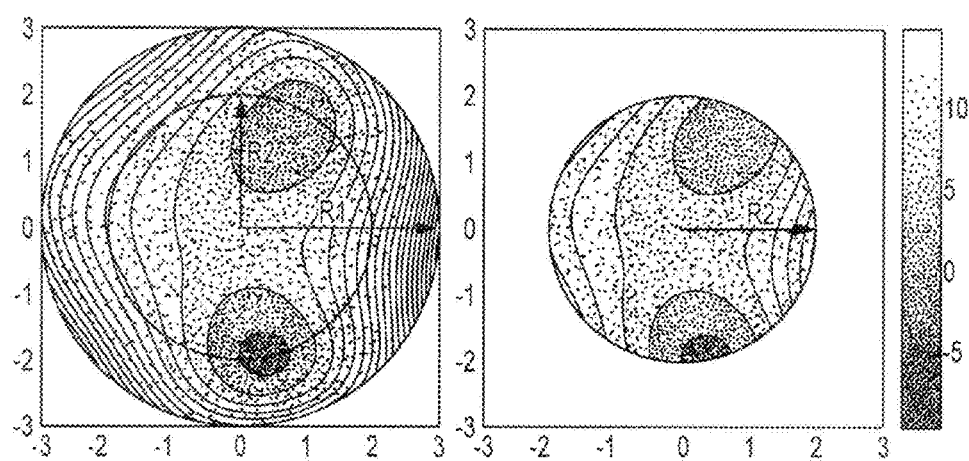
FIGS. 3D and 3E are contour plots of a wavefront at two different pupil sizes.

Assume that the pupil aperture changes from $R_1$ to $R_2$, as shown in FIGS. 3D and 3E. The ocular aberrations of the pupil with the smaller radius, $R_2$, are the same as the aberrations of the area defined by radius $R_2$ when the pupil size is $R_1$; i.e., the aberrations do not change when the pupil size changes.

FIGS. 3D and 3E graphically illustrate contour plots of a wavefront map with pupil radius $R_1$ (in FIG. 3D) and the wavefront map when the pupil size constricts to pupil radius $R_1$ to $R_2$ (in FIG. 3E). The two maps are in the same scale. Units are in micrometers of optical path difference. Note that the portion of the wavefront defined by $R_2$ in FIG. 3D is the same as the plot in FIG. 3E.

If $F_i(r, \theta)$ is replaced by Zernike polynomials $Z_i(r, \theta)$ in Eq. (1A), the entire wavefront over the pupil with radius $R_1$ can be written as:

$$W_1(R_1 r, \theta) = \sum_{i=0}^{\infty} a_i Z_i(r, \theta), \quad \text{(Eq. 5A)}$$

where $a_i$ is the ith Zernike coefficient representing the Zernike expansion into the pupil when the pupil radius is $R_1$. Similarly, the entire wavefront over the pupil with radius $R_2$ can be written as:

$$W_2(R_2 r, \theta) = \sum_{i=0}^{\infty} b_i Z_i(\epsilon r, \theta), \quad \text{(Eq. 6A)}$$

where $b_i$ is the ith Zernike coefficient representing the Zernike expansion into the pupil when the pupil radius is $R_2$. The next step is to determine the relationship of $\{b_i\}$ to $\{a_i\}$.

From Eq. (5A), to represent only the area defined by radius $R_2$, $W'_1(R_1 r, \theta)$, only r (which runs from 0 to 1) needs to be scaled by a scaling factor of $\epsilon r$, which runs from 0 to $\epsilon$. Therefore, $$W'_1(R_1 r, \theta) = \sum_{i=0}^{\infty} a_i Z_i(\epsilon r, \theta). \quad \text{(Eq. 7A)}$$

As shown in FIGS. 3D and 3E, it is known that $$W_1'(R_1 r, \theta) = W_2(R_2 r, \theta) \quad \text{(Eq. 8A)}$$

And so, from Eqs. (6A)-(8A), it is found that $$\sum_{i=0}^{\infty} b_i Z_i(r, \theta) = \sum_{i=0}^{\infty} a_i Z_i(\epsilon r, \theta). \quad \text{(Eq. 9A)}$$

Derivation of Eq. (9A) comes from the definition of wavefront expansion into basis functions. Equation (9A) can be applied to any set of basis functions. If the triangular function is the same in both sides of Eq. (9A), i.e., there is no rotation, after Eq. (2A) is applied the relationship between the sets of coefficients $\{a_i\}$ and $\{b_i\}$ is $$\sum_n \sum_m b_n^m R_n^{|m|}(r) = \sum_n \sum_m a_n^m R_n^{|m|}(\in r). \tag{Eq. 10A}$$

Substituting $R_n^m(r)$ from Eq. (3A) to Eq. (10A) yields $$\sum_{n=0}^{N} \sum_m b_n^m \sum_{s=0}^{(n-|m|)/2} \frac{(-1)^s \sqrt{n+1}\,(n-s)!\,r^{n-2s}}{s![(n+m)/2-s]![(n-m)/2-s]!} = \tag{Eq. 11A}$$

$$\sum_{n=0}^{N} \sum_m a_n^m \sum_{s=0}^{(n-|m|)/2} \frac{(-1)^s \sqrt{n+1}\,(n-s)!\,\in^{n-2s} r^{n-2s}}{s![(n+m)/2-s]![(n-m)/2-s]!},$$

where N is the total number of orders used for the expansion. Expanding this equation into a radial series yields radial powers of r from 0 to N, resulting in (N+1) equations. This leads to a solution for (N+1) relations between $a_n^m$ and $b_n^m$.

Going from top to bottom for radial powers of r in Eq. (11A), consider the $r^N$ case. We get $r^N$ terms only when n=N and s=0. Then Eq. (11A) results in $$b_N^m = \in^N a_N^m \tag{Eq. 12A}$$

Similarly, for the $r^{N-1}$ case, we get the terms only when n=N−1 and s=0. Then Eq. (11A) yields $$b_{N-1}^m = \in^{N-1} a_{N-1}^m \tag{Eq. 13A}$$

To obtain a general solution, consider the order n with azimuthal frequency m. So far $r^n$, we know that s=0 for order n, s=1 for order n+2, s=2 for order n+4, ..., or s=(N−n)/2 for order n+2[(N−n)/2] can have the radial order of $r^n$. Hence, $$\sum_{i=0}^{(N-n)/2} b_{n+2i}^m \frac{(-1)^i \sqrt{n+2i+1}\,(n-i)!\,r^n}{i![(n+2i+m)/2-i]![(n+2i-m)/2-i]!} = \tag{Eq. 14A}$$

$$\sum_{i=0}^{(N-n)/2} a_{n+2i}^m \frac{(-1)^i \sqrt{n+2i+1}\,(n-i)!\,\in^n r^n}{i![(n+2i+m)/2-i]![(n+2i-m)/2-i]!},$$

In Eq. (14A), index i was used to prevent confusion with index s used in Eq. (11A), although both i and s have the same summation structure. Because Eq. (14A) was derived for $r^n$ only, m can be any integer from −n to n with a step of 2.

Because the denominators at both sides of Eq. (14A) are the same for any given i, then $$\sum_{i=0}^{(N-n)/2} \frac{b_{n+2i}^m}{i!}(-i)^i \sqrt{n+2i+1}\,(n+i)! = \tag{Eq. 15A}$$

$$\sum_{i=0}^{(N-n)/2} \frac{\in^n a_{n+2i}^m}{i!}(-1)^i \sqrt{n+2i+1}\,(n+i)!.$$

Expanding i=0 case from Eq. (15A), we can obtain a recursive formula as $$b_n^m = \in^n a_n^m + \sum_{i=1}^{(N-n)/2} \frac{(-1)^i}{i!n!} \sqrt{\frac{n+2i+1}{n+1}} \times \tag{Eq. 16A}$$

$$(n+i)!(\in^n a_{n+2i}^m - b_{n+2i}^m)$$

$$= \in^n a_n^m + \sum_{i=1}^{(N-n)/2} \frac{(-1)^i}{i!} \sqrt{(n+2i+1)(n+1)} \times$$

$$(n+i)(n+i-1)\cdots(n+2)(\in^n a_{n+2i}^m - b_{n+2i}^m)$$

$$= \in^n a_n^m + \sum_{i=1}^{(N-n)/2} \frac{(-1)^i(n+i)!}{(n+1)!i!}$$

$$\sqrt{(n+2i+1)(n+1)} \times (\in^n a_{n+2i}^m - b_{n+2i}^m).$$

Equation (16A) is the final recursive formula. With the use of Eq. (16A) and Eqs. (12A) and (13A), relations between $\{b_i\}$ and $\{a_i\}$ can be obtained analytically.

To obtain a nonrecursive formula, Eq. (16A) is applied to replace $b_{n+2i}^m$. For example, the coefficient of the (n+2)th order can be written as $$b_{n+2}^m = \in^{n+2} a_{n+2}^m + \sum_{i=1}^{(N-n)/2-1} \frac{(-1)^i(n+i+2)!}{(n+3)!i!} \times \tag{Eq. 17A}$$

$$\sqrt{(n+2i+3)(n+3)}\,(\in^{n+2} a_{n+2i+2}^m - b_{n+2i+2}^m).$$

With the expansion of $b_{n+2i}^m$ to each order higher than n for $b_{n+2i}$ in Eq. (16A) and some laborious arithmetic (see the derivation of Eq. 18A below), a final analytical formula is obtained as $$b_n^m = \in^n \left[ \begin{array}{c} a_n^m + \sum_{i=1}^{(N-n)/2} a_{n+2i}^m \sqrt{(n+2i+1)(n+1)} \times \\ \sum_{j=0}^{i} \frac{(-1)^{i+j}(n+i+j)!}{(n+j+1)!(i-j)!j!} \in^{2j} \end{array} \right]. \tag{Eq. 18A}$$

Sometimes it is useful to use unnormalized Zernike polynomials. In this case, Eq. (18A) can be derived (see the derivation of Eq. 19A below) as $$b_n^m = \tag{Eq. 19A}$$

$$\in^n \left[ a_n^m + (n+1) \sum_{i=1}^{(N-n)/2} a_{n+2i}^m \sum_{j=0}^{i} \frac{(-1)^{i+j}(n+i+j)!}{(n+j+1)!(i-j)!j!} \in^{2j} \right].$$

The dioptric power of human eyes is typically the power desired from a thin lens with a uniform optical power to give the subject the best distance vision. This dioptric power may be independent of pupil size. However, if high-order aberrations are present, especially radially symmetrical terms, dioptric power can change when pupil size changes. The instantaneous power that is dependent on pupil size is herein called effective power.

Because of the aberration-balancing nature of Zernike polynomials, all symmetrical terms are balanced to give a minimum root-means-square error. And so, an aspherical optical surface represented by different high-order spherical aberrations can be used to increase the depth of field. Therefore, the effective power can be defined only by the defocus term as $$P_{eff} = -\frac{4\sqrt{3}\, a_2^0}{R^2}, \qquad \text{(Eq. 20A)}$$

where R stands for the instantaneous pupil radius in millimeters when the instantaneous coefficient of defocus term $a_2^0$ is given in micrometers to get the effective power of the diopters. If a wavefront map is defined in radius R with a set of Zernike polynomials, when the pupil constricts, the smaller map is then redefined with a new set of Zernike polynomials, and it will have a set of Zernike coefficients that is different from the original set.

If only the defocus term (n=2, m=0) is considered, Eq. (18A) becomes $$b_2^0 = \epsilon^2 \qquad \text{(Eq. 21A)}$$
$$\left[ a_2^0 \sum_{i=1}^{N/2-1} a_{2(i+1)}^0 \sqrt{3(3+2i)} \sum_{j=0}^{i} \frac{(-1)^{i+j}(i+j+2)!}{(i-j)!(j+3)!j!} \epsilon^{2j} \right].$$

Taking $a_2^0$ as $b_2^0$ and R as $\epsilon R$ in Eq. (20A) and using Eq. (21A), the effective power becomes $$P_{eff}(\epsilon) = -\frac{4\sqrt{3}}{R^2} \qquad \text{(Eq. 22A)}$$
$$\left[ a_2^0 + \sum_{i=1}^{N/2-1} a_{2(i+1)}^0 \sqrt{3(3+2i)} \times \sum_{j=0}^{i} \frac{(-1)^{i+j}(i+j+2)!}{(i-j)!(j+3)!j!} \epsilon^{2j} \right].$$

Sometimes wavefronts of radially symmetric aspheric optical surfaces are not represented by Zernike polynomials but by power series. In this case, the wavefront is written as $$W(Rr) = \sum_{n=0}^{N/2} a_{2n} r^{2n}, \qquad \text{(Eq. 23A)}$$

where R stands for the pupil radius, r is the radial variable in polar coordinates that defines the unit circle, and N is the maximum radial power. The coefficients $\{a_{2n}\}$ of the power series of Eq. (23A) can be converted into Zernike polynomials so that the effective power can be written as $$P_{eff}(\epsilon) = -\frac{12}{R^2} \sum_{n=1}^{N/2} \frac{n\, \epsilon^{2(n-1)}}{(n+1)(n+2)} a_{2n}. \qquad \text{(Eq. 24A)}$$

The influence of spherical aberration on refraction may not have previously been quantified analytically. Equation (22A) indicates that when higher-order spherical aberrations exist, the effective power is no longer determined only by the defocus term. With Eqs. (22A) and (24A), it is now possible to evaluate the influence of an aspheric shape on refraction.

Embodiments of the present invention encompass nonrecursive formulae for calculating a new set of Zernike polynomial expansion coefficients for ocular aberrations when the pupil constricts or dilates. A relationship has been established between the effective power and the high-order radially symmetrical terms that can be useful for determining the influence of high-order spherical aberrations on refraction. Some or all of the approaches described herein may be embodied in methods and systems for measuring optical characteristics (often including wavefront data) of eyes and other optical systems, for generating desired refractive changes (including prescriptions), and/or for implementing refractive changes (including laser eye surgery, contact lenses, intraocular lenses, and the like). Such embodiments may optionally include (and/or make use of) some or all of the structures described above regarding FIGS. 1-3A, optionally per the exemplary embodiments of FIGS. 3B and 3C. A wide variety of alternative embodiments may also be implemented, optionally using any of the wide variety of known eye measurement and refraction altering techniques, new eye measurement and refraction altering techniques which are developed, or a combination of both. Exemplary embodiments may, for example, be used for calculation of effective powers of an eye at differing pupil sizes and/or locations, including those induced by differing viewing distances (and/or other viewing conditions). As explained in more detail US Patent Publication No. 20040169820, the full disclosure of which is incorporated herein by reference, such calculations of effective powers may have advantages for treatment of presbyopia.

Derivation of Equation (18A)

Begin with the formula for orders n+2. Expand Eq. (17A) as $$b_{n+2}^m = \epsilon^{n+2} a_{n+2}^m - \sqrt{(n+5)(n+3)}\, (\epsilon^{n+2} a_{n+4}^m - b_{n+4}^m) + \qquad \text{(Eq. A1A)}$$
$$\frac{1}{2}(n+4)\sqrt{(n+7)(n+3)}\, (\epsilon^{n+2} a_{n+6}^m - b_{n+6}^m) -$$
$$\frac{1}{6}(n+5)\times(n+4)\sqrt{(n+9)(n+3)}\, (\epsilon^{n+2} a_{n+8}^m - b_{n+8}^m) +$$
$$\ldots + (-1)^{(N-n)/2-1} \frac{\sqrt{(N+1)(n+3)}}{[(N-n)/2-1]!} [(N+n)/2+1] \times$$
$$[(N+n)/2]\ldots(n+5)(n+4)(\epsilon^{n+2} a_N^m - b_N^m),$$

where it is assume that N−n is even. If N−n is odd, Eq. (A1A) becomes $$b_{n+2}^m = \epsilon^{n+2} a_{n+2}^m - \sqrt{(n+5)(n+3)}\, (\epsilon^{n+2} a_{n+4}^m - b_{n+4}^m) + \qquad \text{(Eq. A2A)}$$
$$\frac{1}{2}(n+4)\times\sqrt{(n+7)(n+3)}\, (\epsilon^{n+2} a_{n+6}^m - b_{n+6}^m) -$$
$$\frac{1}{6}(n+5)(n+4)\times\sqrt{(n+9)(n+3)}\, (\epsilon^{n+2} a_{n+8}^m - b_{n+8}^m) +$$
$$\ldots + (-1)^{(N-n-3)/2} \times$$
$$\frac{\sqrt{N(n+3)}}{[(N-n-3)/2]!} [(N+n+1)/2][(N+n-1)/2]$$
$$\ldots \times (n+5)(n+4)(\epsilon^{n+2} a_{N-1}^m - b_{N-1}^m).$$

It is assumed for the next two formulas that N−n is even. If N−n is odd, an adjustment similar to that in Eq. (A2A) can be done. To simplify the process, formulas for N−n being odd will not be given for the next two cases.

Similarly, for order n+4, the expression becomes $$b_{n+4}^m = \epsilon^{n+4} a_{n+4}^m - \sqrt{(n+7)(n+5)} \, ( \epsilon^{n+4} a_{n+6}^m - b_{n+6}^m) + \qquad \text{(Eq. A3A)}$$
$$\frac{1}{2}(n+6) \times \sqrt{(n+9)(n+5)} \, ( \epsilon^{n+4} a_{n+8}^m - b_{n+8}^m) -$$
$$\frac{1}{6}(n+7)(n+6) \times \sqrt{(n+11)(n+5)}$$
$$( \epsilon^{n+4} a_{n+10}^m - b_{n+10}^m) + \ldots + (-1)^{(N-n)/2-2} \times$$
$$\frac{\sqrt{(N+1)(n+5)}}{[(N-n)/2-2]!} [(N+n)/2+2][(N+n)/2+1]$$
$$\ldots \times (n+7)(n+6)( \epsilon^{n+4} a_N^m - b_N^m).$$

And for order n+6, the expression is $$b_{n+6}^m = \epsilon^{n+6} a_{n+6}^m - \sqrt{(n+9)(n+7)} \, ( \epsilon^{n+6} a_{n+8}^m - b_{n+8}^m) + \qquad \text{(Eq. A4A)}$$
$$\frac{1}{2}(n+8) \times \sqrt{(n+11)(n+7)} \, ( \epsilon^{n+6} a_{n+10}^m - b_{n+10}^m) -$$
$$\frac{1}{6}(n+9)(n+8) \times \sqrt{(n+11)(n+7)}$$
$$( \epsilon^{n+6} a_{n+12}^m - b_{n+12}^m) + \ldots + (-1)^{(N-n)/2-3} \times$$
$$\frac{\sqrt{(N+1)(n+7)}}{[(N-n)/2-3]!} [(N+n)/2+3][(N+n)/2+2]$$
$$\ldots \times (n+9)(n+8)( \epsilon^{n+6} a_N^m - b_N^m).$$

If this process continues, we would finally obtain either Eq. (12A) or Eq. (13A) depending on whether N−n is even or odd. With the use of Eqs. (A1A)-(A4A), Eqs. (12A) and (13A), and combinations of terms for $a_n^m$, $a_{n+2}^m$, $a_{n+4}^m$, ..., Eq. (16A) becomes $$b_n^m = \epsilon^n a_n^m - \sqrt{(n+3)(n+1)} \, \epsilon^n (1-\epsilon^2) a_{n+2}^m + \qquad \text{(Eq. A5A)}$$
$$\frac{1}{2}[(n+2)-2(n+3)\epsilon^2 +(n+4)\epsilon^4] \times$$
$$\sqrt{(n+5)(n+1)} \, \epsilon^n a_{n+4}^m - \frac{1}{6}[(n+2)(n+3)-3(n+3)$$
$$(n+4)\epsilon^2 + 3(n+4)(n+5)\epsilon^4 -(n+5)(n+6)\epsilon^6]$$
$$\sqrt{(n+7)(n+1)} \, \epsilon^n$$
$$a_{n+6}^m + \ldots \; .$$

Noticing that the fraction in each summation term of a Zernike coefficient can be expressed as $(-1)^j/j!$, where j is the order of the summation term, and that the number of expansion into $\epsilon$ with each summation is similar to a binomial expansion with an increasing number of multiplication factors relating to n, we can express a final analytical formula as $$b_n^m = \epsilon^n \left[ a_n^m \sum_{i=1}^{(N-n)/2} a_{n+2i}^m \sqrt{(n+2i+1)(n+1)} \times \qquad \text{(Eq. A6A)} \right.$$
$$\left. \sum_{j=0}^{i} \frac{(-1)^{i+j}(n+i+j)!}{(n+j+1)!(i-j)!j!} \epsilon^{2j} \right]$$

Derivation of Equation (19A)

The unnormalized Zernike polynomials can be written as $$Z_i(r,\theta) = R_n^{\{|m|\}}(r)\theta^m(\theta) \qquad \text{(Eq. B1A)}$$

where the unnormalized Zernike radial polynomials are defined as $$R_n^{\{|m|\}}(r) = \sum_{s=0}^{(n-|m|)/2} \frac{(-1)^s (n-s)!}{s![(n+m)/2-s]![(n-m)/2-s]!} r^{n-2s}. \qquad \text{(Eq. B2A)}$$

Following a process similar to that described previously, the recursive formula for unnormalized Zernike coefficients can be derived as $$b_n^m = \epsilon^n a_n^m + \sum_{i=1}^{(N-n)/2} \frac{(-1)^i (n+i)!}{n!i!} ( \epsilon^n a_{n+2i}^m - b_{n+2i}^m). \qquad \text{(Eq. B3A)}$$

With the same process as described in Appendix A, a final nonrecursive formula for unnormalized Zernike coefficients can be written as $$b_n^m = \epsilon^n \left[ a_n^m + \qquad \text{(Eq. B4A)} \right.$$
$$\left. (n+1) \sum_{i=1}^{(N-n)/2} a_{n+2i}^m \times \sum_{j=0}^{i} \frac{(-1)^{i+j}(n+i+j)!}{(n+j+1)!(i-j)!j!} \epsilon^{2j} \right].$$

Iris registration, as discussed for example in Chernyak, D. A., *J. Refract. Surg.*, 21:463-468 (2005), can be used to correct or reduce the error from the misalignment between the pupil in front of the aberrometer and the pupil under the laser. Because the iris features are typically not affected by the change of pupil size, they can be used as reliable references to establish the relative geometrical displacement between two image frames, as discussed in Daugman, J., *IEEE Trans, PAMI*, 15:1148-1161 (1993). A common coordinate system can thus be established so as to facilitate the full correction of ocular aberrations. For practical applications, however, a full correction may not be possible partly because of the fluctuation of the high order aberrations and partly because of the instrument error. Therefore, it may be useful to have a tool for the error analysis of an imperfect correction for the misalignment of the eye between the pupil in front of the aberrometer and the pupil under the laser. Embodiments of the present invention provide systems and methods for predicting error if no registration is performed, or if registration is inaccurately performed. Moreover, for a majority of the data analysis for ocular aberrations, it is often helpful to standardize pupil sizes of different wavefront exams to a given pupil size. Embodiments of the present invention encompass pupil resizing of known wavefronts. In addition, the constriction, dilation, and decentration of a pupil can lead to wavefront refraction change when high order aberrations are present. Certain aspects of this ocular effect can be used as the basis for designing optical surfaces for the correction or treatment of presbyopia, a condition which is discussed in Dai, G-m., *Appl. Opt.*, 45:4184-4195 (2006).

1. Wavefront Transformation and Iris Registration

In understanding wavefront transformation and iris registration, it is helpful to consider features of a human eye and how an iris registration is implemented.

1.1 Definitions

Figure 4:
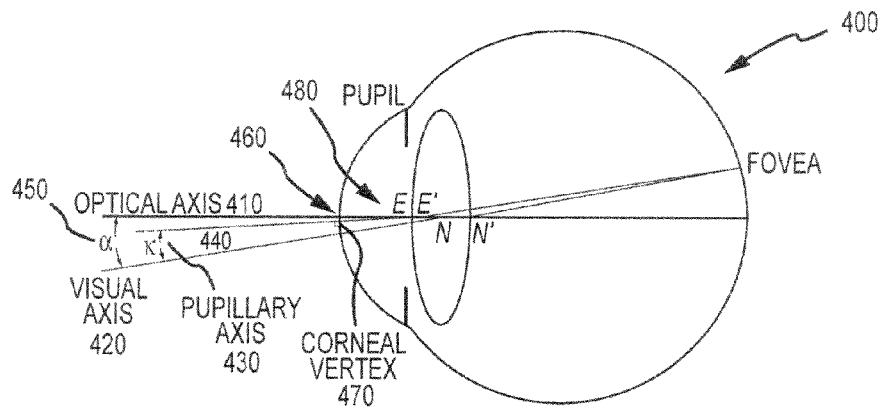
FIG. 4 shows an illustration of the human eye according to embodiments of the present invention.

The following exemplary definitions may be useful for a discussion of wavefront transformation and iris registration for vision correction, according to some embodiments of the present invention. FIG. 4 shows an illustration of the human eye 400, and depicts the following features: optical axis, visual axis, pupillary axis, angle alpha, angle kappa (angle lambda), and corneal vertex (not to scale). N and N' are the first and second nodal points, and E and E' are the centers of the entrance and exit pupils, respectively.

Purkinje images can be defined as images of a light source reflected by different surfaces of the optics of the eye. A first Purkinje image (Purkinje I) can be the reflection from the anterior surface of the cornea. A second Purkinje image (Purkinje II) can be the reflection from the posterior surface of the cornea. A third Purkinje image (Purkinje III) can be the reflection of the anterior surface of the crystalline lens. A fourth Purkinje image (Purkinje IV) can be the reflection of the posterior surface of the crystalline lens and can be the only inverted image. The brightness of the Purkinje images can be calculated from the Fresnel equation.

The optical axis 410 of a human eye can be defined as an imaginary line that connects a point source and all Purkinje images when they are aligned to coincide. Because the eye is typically not rotationally symmetric, this alignment of all Purkinje images may be difficult to achieve.

The visual axis 420 of a human eye can be defined as a line that connects the light source and first nodal point (N) and the second nodal point (N') to the fovea when the eye is fixated to the target. The visual axis can also be referred to as the line of sight.

The pupillary axis 430 of a human eye can be defined as the line that is perpendicular to the cornea and connects to the center of the entrance pupil (E) and the center of the exit pupil (E') to the fovea. In some embodiments, this can be achieved by adjusting the first Purkinje image to the center of the entrance pupil so the line connecting the light source and the pupil center defines the pupillary axis.

Angle Kappa 440 can be defined as the angle between the pupillary axis and visual axis, or the line of sight. Angle kappa may also be referred to as angle lambda. Angle kappa can be defined as positive if the pupillary axis is nasal to the visual axis, and negative if it is temporal to the visual axis. Typically, the angle kappa is smaller than the angle alpha.

Angle Alpha 450 can be defined as the angle between the visual axis and the optical axis. A typical value of angle alpha can be within a range from about $4° \leq a \leq 8°$.

The corneal apex 460 can be defined as the point on the cornea that has the steepest curvature. For example, the corneal apex 460 can be disposed at the intersection of the anterior surface of the cornea and the optical axis. In some embodiments, it is a fixed point to a given cornea and does not depend upon any measurements. The corneal apex can sometimes be confused with the corneal vertex.

The corneal vertex 470 can be defined as the intersection of the pupillary axis with the anterior surface of the cornea, if the pupillary axis coincides with the optical axis of the measuring device, such as a corneal topographer.

The pupil center 480 can be defined as the center of a best fit ellipse to the pupil. The majority of human pupils are elliptical to some extent. Some pupils are even irregular.

As an exemplary illustration, it is possible to estimate the distance on the cornea for a kappa angle of 3.5° as follows. Using a nominal value of 3.5 mm as the anterior chamber depth, we obtain $3.5 \times \tan(3.5\pi/180) = 0.214$ mm. Therefore, in this example the corneal vertex is two tenths of a millimeter nasal to the pupil center.

1.2 Iris Registration

Figures 5A, 5B:
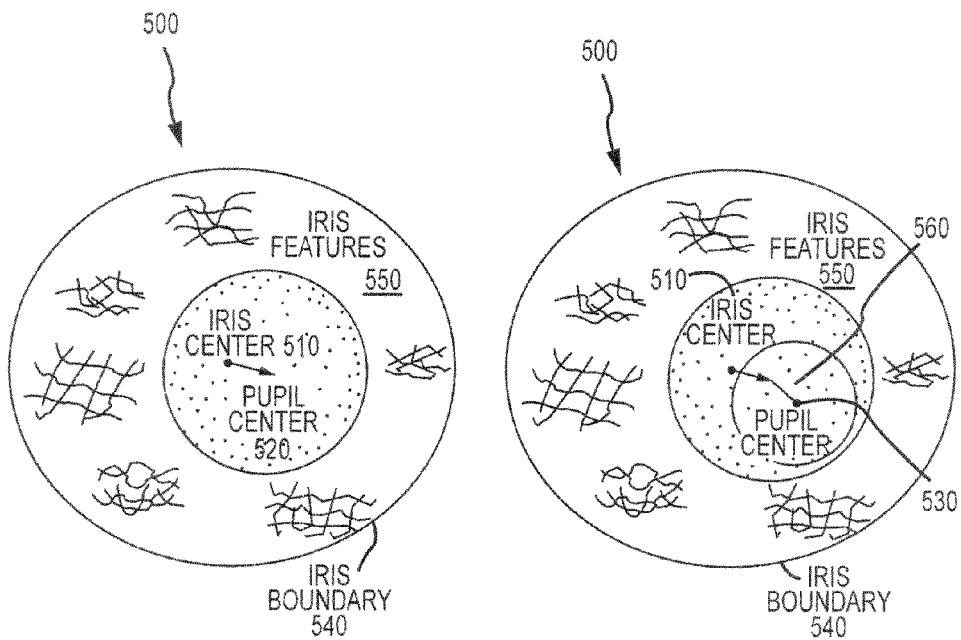
FIGS. 5A and 5B show exemplary illustrations of a human eye in various contexts, according to embodiments of the present invention.

In understanding iris registration, it is helpful to consider a typical situation for wavefront-driven refractive surgery as shown in FIGS. 5A and 5B. The patient is brought in for pre-operatively wavefront exam in front of a wavefront aberrometer. In some embodiments, to capture the entire ocular aberration of the eye, the wavefront measurement room is usually dimmed to scotopic conditions. As such, the pupil size is relatively large. In some embodiments, when the patient is laying under the laser, the surgery room is relatively bright so the pupil constricts to a smaller size. In general, the pupil constriction is not concentric. Therefore, the pupil center can shift between these two situations with respect to a stationary reference, such as the iris of the eye. FIG. 5A provides an exemplary illustration of a human eye when the patient is in front of the wavefront device. This may correspond to an evaluation environment or context. FIG. 5B provides an exemplary illustration of a human eye when the patient is under the laser (not to scale). This may correspond to a treatment environment or context. As shown here, an eye 500 can present an iris center 510, a pupil center 520 when the patient is in front of the wavefront device, a pupil center 530 when the patient is under the laser, an iris boundary 540, and one or more iris features 550. A distance between the two pupil centers 520, 530 can be referred to as a pupil center shift 560.

When the ocular wavefront is examined, a treatment plan is typically generated based on the ocular aberrations. If a treatment is referenced to the pupil center, it may not be delivered to the correct location if the pupil center shifts, as can be seen in FIGS. 5A and 5B. The iris of the human eye contains irregular texture that can be used as coordinate references, because the iris (together with the texture) typically does not change when the pupil size changes. Hence, in an exemplary approach a certain number of iris features can be identified and used as references. A treatment plan can be referenced to the stable iris features when the plan is created. When the patient is laying under the laser, the eye of the patient can be captured and analyzed. The iris features can be identified again and the coordinate can be established. The laser delivery optics are aligned properly so the two coordinate systems coincide. Consequently, the treatment can be delivered correctly as planned.

Figure 6:
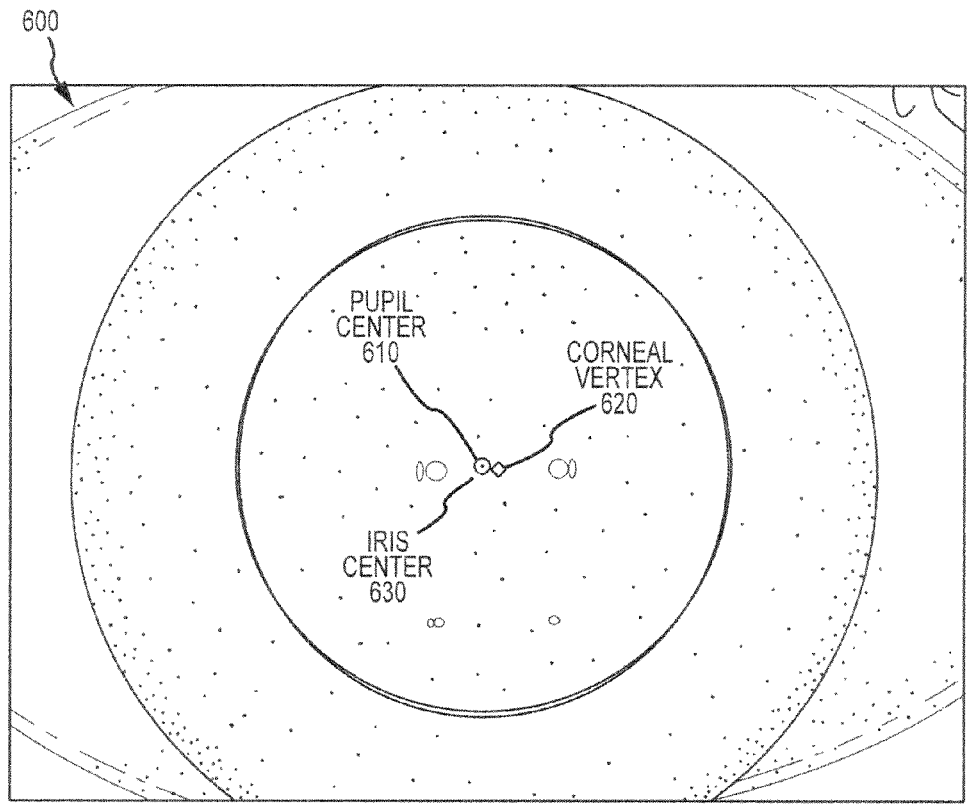
FIG. 6 shows an illustration of the human eye according to embodiments of the present invention.

One of the side results may be a determination of the corneal vertex from the first Purkinje image of the laser source of the wavefront device, as shown in FIG. 6. As seen in this exemplary diagram of an eye 600, a pupil center 610 and a corneal vertex 620 are the two intersections of the visual axis and the pupillary axis, respectively, with the anterior surface of the cornea. Therefore, the distance between the pupil center and the corneal vertex can determine the angle kappa on the anterior surface of the cornea. Although the visual axis may not strictly pass through the pupil center, the deviation can be very small and often negligible. FIG. 6 presents a pupil image that shows an iris center 630, pupil center 610, and corneal vertex 620 that is the Purkinje reflex of the laser source of the wavefront device. Both the iris boundary and the pupil boundary can be detected with best-fit ellipses.

For the correction of presbyopia, which is discussed for example in Dai, G-m., *Appl. Opt.*, 45:4184-4195 (2006), some surgeons believe that it is better to put the presbyopic correction shape over the corneal vertex instead of the pupil center as the pupil center can tend to move toward the corneal vertex during accommodation. Some studies, including Yang, Y. et al., *Invest. Ophthal. Vis. Sci.*, 43:2508-2512 (2002), Walsh, G., *Ophthal. Physiol. Opt.*, 8:178-182 (1988), and Wyatt, H. J., *Vis. Res.*, 35:2021-2036 (1995) have indicated that the pupil center tends to move nasally and inferiorly when the pupil constricts. It has now been discovered that there is a weak but statistically significant correlation between the pupil center shift and the angle kappa in the x direction. Embodiments of the present invention encompass systems and methods for putting a presbyopic correction shape over an accommodated pupil center, rather than putting it over the corneal vertex.

2. Wavefront Representation for Pupil Resizing

As discussed elsewhere herein, a pupil can constrict because of an increase of the ambient lighting and because of accommodation. For wavefront analysis, a commonly used metric involves the root mean square (RMS) error of the wavefront. However, the RMS wavefront error typically depends upon the pupil size, or more strictly speaking, the wavefront diameter. Therefore, it can be helpful to normalize (or resize) wavefront maps to the same pupil size.

Typically, pupil constriction is not concentric. According to some embodiments of the present invention, the pupil constriction can be treated as concentric. A discussion of non-concentric pupil constriction is further discussed in Section 5, below. For the majority of wavefront analysis, the pupil resizing does not involve a large amount of pupil size changes. For example, for non-presbyopic eyes, a 6 mm pupil size is often used as a normalized pupil size; for presbyopic eyes, a 5 mm pupil size can be used instead. The pupil center shift due to the pupil size change under these conditions is relatively small and may be ignored for most of the analysis. In the case where a more accurate analysis is needed or desired, it is helpful to refer to the discussion in Section 5, below. Embodiments of the present invention encompass wavefront representations for pupil resizing for both pupil constrictions and pupil dilations.

2.1 General Consideration

A discussion of wavefront representation for pupil constriction is provided in Dai, G.-m., *J. Opt. Soc. Am. A.*, 23:539-543 (2006), when Zernike polynomials are used as the basis functions. It may be assumed that optical properties of human eye do not change when pupil size changes. A resizing technique has now been discovered that can be used with any basis functions. Suppose an ocular wavefront is represented by a set of basis functions $\{F_i(\rho,\theta)\}$ as $$W(R_1\rho, \theta) = \sum_{i=0}^{J} a_i F_i(\rho, \theta). \quad (1)$$

where $R_1$ is the pupil radius, J is the highest basis function, and $a_i$ is the coefficient of the ith basis function. We further assume that $\{F_i(\rho,\theta)\}$ can be separated into a set of radial polynomials and a triangular function as $$F_i(\rho,\theta)=S_i(\rho)T_i(\theta). \quad (2)$$

Figures 7A, 7B:
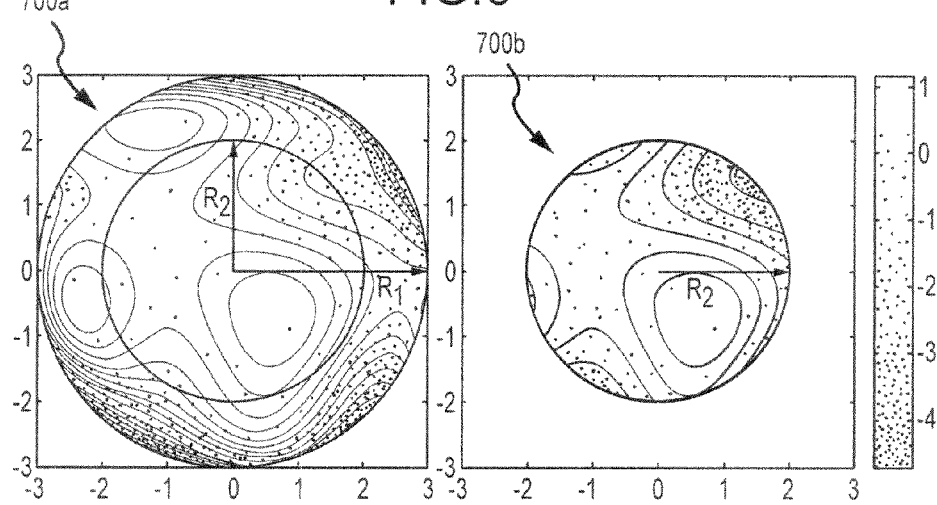
FIGS. 7A and 7B show exemplary illustrations of wavefront map contour plots for a human eye, according to embodiments of the present invention.

FIG. 7A provides a contour plots of a wavefront map 700a with pupil radius R1 and FIG. 7B provides a contour plot of the wavefront map 700b when the pupil size constricts to pupil radius R2. Both maps are in the same scale, and units can be in microns of optical path difference. The portion of the wavefront defined by R2 in FIG. 7A is the same as the plot in FIG. 7B. Consider for example an ocular wavefront of 6 mm pupil, which may be illustrated by FIG. 7A. When the pupil constricts to $R_2$, only the part that is within radius $R_2$ is represented, as may be illustrated in FIG. 7B. Because the optical components, which are often mainly the cornea and the crystalline lens, typically do not change during the pupil constriction, the aberration pattern of the constricted wavefront shown in FIG. 7B is the same as the original wavefront within radius $R_2$ as shown in FIG. 7A. When $\rho=1$, $W(R_1\rho,\theta)$ represents the entire wavefront. When $\rho$ becomes smaller than 1, the represented wavefront becomes smaller. Hence, the part of the wavefront within radius $R_2$ in FIG. 7A can be expressed as $W(R_2\rho,\theta)$, or expressed as $W(R_1\epsilon\rho,\theta)$ by simply scaling the radial variable $\rho$ by $\epsilon=R_2/R_1$ to $\epsilon\rho$. Therefore, we have $$W(R_1\epsilon\rho,\theta)=W(R_2\rho,\theta). \quad (3)$$

For the wavefront as shown in FIG. 7B, we can represent it as $$W(R_2\rho, \theta) = \sum_{i=0}^{J} b_i F_i(\rho, \theta), \quad (4)$$

where $b_i$ is the coefficient of the ith basis function. Substituting Eqs. (1) and (6) into (3), we get $$\sum_{i=0}^{J} a_i F_i(\epsilon\rho, \theta) = \sum_{i=0}^{J} b_i F_i(\rho, \theta). \quad (5)$$

Substituting Eq. (2) into Eq. (5) and considering the fact that the triangular function $T_i(\theta)$ can be the same on both sides of Eq. (5) because no rotation is involved, we obtain $$\sum_{i=0}^{J} a_i S_i(\epsilon\rho) = \sum_{i=0}^{J} b_i S_i(\rho). \quad (6)$$

Equation (6) is the basis for relating the coefficients of a set of basis functions before and after pupil constriction. It can apply to any set of basis functions so long as the basis set can be separated into a product of a set of radial polynomials and a triangular function.

2.2 Pupil Resizing Polynomials

Suppose the radial polynomials $S_i(\rho)$ is orthogonal over the unit circle and the orthogonality is written as $$\frac{1}{A}\int_0^1 S_i(\rho)S_{i'}(\rho)\rho\, d\rho = \delta_{ii'}. \quad (7)$$

In Eq. (7), A is an orthogonalization constant. Multiplying $S_{i'}(\rho)$ on both sides of Eq. (6), integrating over the unit circle, and using the orthogonality in Eq. (7), we have $$b_{i'} = \sum_{i=0}^{J} a_i \int_0^1 S_i(\epsilon\rho)S_{i'}(\rho)\rho\, d\rho = \sum_{i=0}^{J} \mathcal{H}_{i'i}(\epsilon)a_i, \quad (8)$$

where the pupil resizing polynomials $H_{i'i}(\epsilon)$ can be expressed as $$\mathcal{H}_{i'i}(\epsilon) = \int_0^1 S_i(\epsilon\rho) S_{i'}(\rho) \rho d\rho. \tag{9}$$

Aspects of equation (9) are discussed in Janssen, A. J. E. M., *J. Microlith., Microfab., Microsyst.*, 5:030501 (2006). It has now been discovered that equation (9) can be applied to any set of basis functions of which the radial polynomials are orthogonal.

When the set of radial polynomials $\{S_i(\rho)\}$ is not orthogonal, a different approach can be used. Because the radial polynomials $\{S_i(\rho)\}$ are polynomials of $\rho$, we may write $S_i(\rho)$ as $$S_i(\rho) = \sum_{k=0}^{i} h_k \rho^k, \tag{10}$$

where $h_k$ is the kth polynomial coefficient that depends only upon the index k. Equation (10) indicates that the variables $\epsilon$ and $\rho$ are separable in the set of radial polynomials $S_i(\epsilon\rho)$ as $$S_i(\varepsilon\rho) = \sum_{k=0}^{i} \mathcal{H}_{ki}(\varepsilon) S_i(\rho). \tag{11}$$

Substituting Eqs. (10) and (11) into Eq. (6), we have $$\sum_{i=0}^{J} a_i \sum_{k=0}^{i} H_{ki}(\varepsilon) S_i(\rho) = \sum_{i=0}^{J} b_i S_i(\rho). \tag{12}$$

Since $S_i(\rho)$ appears on both sides of Eq. (12), it can be eliminated so that Eq. (12) is simplified as $$b_i(\rho) = \sum_{k=0}^{i} \mathcal{H}_{ki}(\varepsilon) a_i. \tag{13}$$

Equation (13) gives a general expression of a new set of coefficients as related to an original set of coefficients when the pupil size changes. The set of polynomials $\mathcal{H}_k(\epsilon)$ is termed the pupil resizing polynomials that is useful in the calculation of coefficients of basis functions when the pupil is resized. Equation (6) presents a generic formula, or a basis for pupil rescaling. Equations (9) and (13) present two different methods of the approach.

Hence, embodiments of the present invention encompass pupil resizing polynomials for several useful sets of basis functions, including Taylor monomials, Zernike polynomials, and Seidel series.

2.3 Taylor Resizing Monomials

When a wavefront is represented by Taylor monomials, the set of Taylor coefficients changes accordingly when the pupil size changes. Taylor monomials can be written as a product of the radial power and the triangular function as $$T_p^q(\rho, \theta) = \rho^p \cos^q \theta \sin^{p-q} \theta. \tag{14}$$

Therefore, the radial monomials can be written as $$S_p(\rho) = \rho^p. \tag{15}$$

Substituting Eq. (15) into Eq. (11), we have $$S_\rho(\epsilon\rho) = \epsilon^p \rho^p = \epsilon^p S_\rho(\rho). \tag{16}$$

Hence, the Taylor resizing monomials can be expressed as $$L_\rho(\epsilon) = \epsilon^p. \tag{17}$$

Equation (17) indicates that the set of Taylor resizing monomials is a set of power series of the pupil resizing ratio $\epsilon$. In other words, each new Taylor coefficient is scaled by $\epsilon^p$ where p is the radial degree of the Taylor monomial. Equation (17) can be a GPRF for a Taylor basis function. The triangular function discussed here is similar to the triangular function discussed for the Zernike polynomials.

Figure 8A:
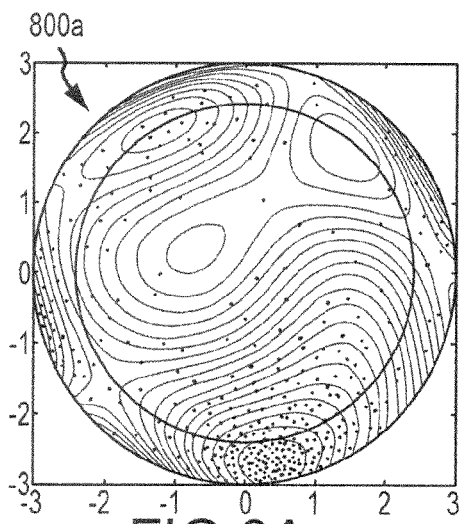
FIGS. 8A and 8B show exemplary illustrations of wavefront maps for a human eye, according to embodiments of the present invention.
Figure 8B:
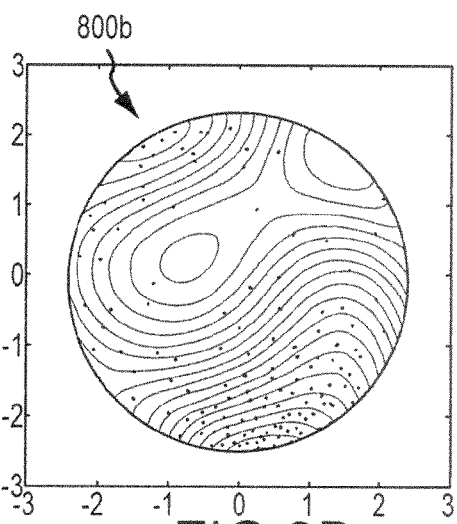

As an example, Table 1 shows a set of Taylor coefficients and the corresponding resized Taylor coefficients when a pupil resizing ratio of 0.8 is assumed. The original wavefront map 800a shown in FIG. 8A and the resized wavefront map 800b shown in FIG. 8B correspond to coefficients listed in Table 1. The resized wavefront appears identical to the inner part of the original wavefront within the new pupil size.

Table 1 shows Taylor coefficients before ($a_\rho^q$) and after ($b_\rho^q$) pupil constriction, where $\epsilon=0.8$.

TABLE 1

| i | p | q | $a_\rho^q$ | $b_\rho^q$ |
|---|---|---|------------|------------|
| 0 | 0 | 0 | 1.0660 | 1.0660 |
| 1 | 1 | 0 | 2.6335 | 2.1068 |
| 2 | 1 | 1 | −3.1810 | 2.1068 |
| 3 | 2 | 0 | −4.6450 | −2.9728 |
| 4 | 2 | 1 | 4.0090 | 2.5658 |
| 5 | 2 | 2 | −4.3256 | −2.2147 |
| 6 | 3 | 0 | −1.6533 | −0.8465 |
| 7 | 3 | 1 | 16.4753 | 8.4354 |
| 8 | 3 | 2 | 1.4026 | 0.7181 |
| 9 | 3 | 3 | 6.9912 | 2.8636 |
| 10 | 4 | 0 | −1.2680 | −0.5194 |
| 11 | 4 | 1 | 4.7939 | 1.9636 |
| 12 | 4 | 2 | 13.3486 | 5.4676 |
| 13 | 4 | 3 | −0.5777 | −0.2366 |
| 14 | 4 | 4 | 8.5984 | 2.8175 |
| 15 | 5 | 0 | 1.2909 | 0.4230 |
| 16 | 5 | 1 | −15.7024 | −5.1454 |
| 17 | 5 | 5 | −6.0772 | −1.9914 |
| 18 | 5 | 3 | −19.7837 | −6.4827 |
| 19 | 5 | 4 | −3.7889 | −1.2415 |
| 20 | 5 | 5 | −2.5517 | −0.6689 |
| 21 | 6 | 0 | 4.2625 | 1.1174 |
| 22 | 6 | 1 | −7.2498 | −1.9005 |
| 23 | 6 | 2 | 2.7658 | 0.7250 |
| 24 | 6 | 3 | −10.5176 | −2.7571 |
| 25 | 6 | 4 | −15.8385 | −4.1520 |
| 26 | 6 | 5 | −6.3212 | −1.6571 |
| 27 | 6 | 6 | −5.4349 | −1.1398 |

2.4 Zernike Resizing Polynomials

Techniques for calculating a new set of Zernike coefficients from an original set when the pupil size changes has been investigated by a number of authors. For example, see Dai, G.-m., *J. Opt. Soc. Am. A*, 23:539-543 (2006), Janssen, A. J. E. M., *J. Microlith., Microfab., Microsyst.*, 5:030501 (2006), Goldberg K. A. et al., *J. Opt. Soc. Am. A*, 18:2146-2152 (2001), Schwiegerling, J., *J. Opt. Soc. Am. A*, 19:1937-1945 (2002), Campbell, C. E., *J. Opt. Soc. Am. A*, 20:209-217 (2003), Shu, L. et al., *J. Opt. Soc. Am. A*, 23:1960-1968 (2006), Bará, S. et al., *J. Opt. Soc. Am. A*, 23:2061-2066 (2006), and Lundström L. et al., *J. Opt. Soc. Am. A*, 24:569-577 (2007). Zernike resizing polynomials can be written as $$G_n^i(\varepsilon) = \varepsilon^n \sqrt{(n+2i+1)(n+1)} \sum_{j=0}^{i} \frac{(-1)^{i+j}(n+i+j)!}{j!(n+j+1)!(i-j)!} \varepsilon^{2j}, \quad (18)$$

so a new set of Zernike coefficients can be related to the original set as $$b_n^m = \sum_{i=0}^{(N-n)/2} G_n^i(\varepsilon) a_{n+2i}^m \quad (19)$$

Table 2 shows the formulas for Zernike resizing coefficients as functions of the Zernike resizing polynomials. Equation (19) indicates that (1) the scaled Zernike coefficients may depend only upon the original Zernike coefficients of the same azimuthal frequency m; (2) the scaled Zernike coefficients may not depend upon the original Zernike coefficients of lower orders. For example, a defocus aberration may not induce spherical aberration when the pupil constricts. On the other hand, a spherical aberration may induce defocus aberration when the pupil constricts.

In Eq. (18), the index n is referred to as the radial order, and the index i is referred to as the depth. When it is used for Zernike polynomials resizing, the depth i is related to the maximum order N of Zernike polynomial expansion as $i \leq (N-n)/2$. Table 3 shows Zernike resizing polynomials up to the 10th order.

There are several properties concerning Zernike resizing polynomials that can be useful for the following discussion. (1) According to some embodiments, Zernike resizing polynomials are zero except for $G_0^0$ when $\varepsilon=1$, i.e., $G_n^i(1)=0$. (2) According to some embodiments, Zernike resizing polynomials of depth zero equal the power of $\varepsilon$, i.e., $G_n^0(\varepsilon)=\varepsilon^n$. (3) According to some embodiments, Zernike resizing polynomials except for $G_n^0$ can be expressed as the difference of two Zernike radial polynomials as functions of $\varepsilon$. A detailed discussion and proof of these properties is given in Appendix A.

Table 2 shows Zernike resizing coefficients expressed as the original Zernike coefficients, where $\varepsilon(<1)$ is the pupil resizing ratio.

TABLE 2

| n | New Coefficients $b_n^m$ |
|---|---|
| 0 | $G_0^0(\varepsilon)a_0^0 + G_0^1(\varepsilon)a_2^0 + G_0^2(\varepsilon)a_4^0 + G_0^3(\varepsilon)a_6^0 + G_0^4(\varepsilon)a_8^0 + G_0^5(\varepsilon)a_{10}^0$ |
| 1 | $G_1^0(\varepsilon)a_1^m + G_1^1(\varepsilon)a_3^m + G_1^2(\varepsilon)a_5^m + G_1^3(\varepsilon)a_7^m + G_1^4(\varepsilon)a_9^m$ |
| 2 | $G_2^0(\varepsilon)a_2^m + G_2^1(\varepsilon)a_4^m + G_2^2(\varepsilon)a_6^m + G_2^3(\varepsilon)a_8^m + G_2^4(\varepsilon)a_{10}^m$ |
| 3 | $G_3^0(\varepsilon)a_3^m + G_3^1(\varepsilon)a_5^m + G_3^2(\varepsilon)a_7^m + G_3^3(\varepsilon)a_9^m$ |
| 4 | $G_4^0(\varepsilon)a_4^m + G_4^1(\varepsilon)a_6^m + G_4^2(\varepsilon)a_8^m + G_4^3(\varepsilon)a_{10}^m$ |
| 5 | $G_5^0(\varepsilon)a_5^m + G_5^1(\varepsilon)a_7^m + G_5^2(\varepsilon)a_9^m$ |
| 6 | $G_6^0(\varepsilon)a_6^m + G_6^1(\varepsilon)a_8^m + G_6^2(\varepsilon)a_{10}^m$ |
| 7 | $G_7^0(\varepsilon)a_7^m + G_7^1(\varepsilon)a_9^m$ |
| 8 | $G_8^0(\varepsilon)a_8^m + G_8^1(\varepsilon)a_{10}^m$ |
| 9 | $G_9^0(\varepsilon)a_9^m$ |
| 10 | $G_{10}^0(\varepsilon)a_{10}^m$ |

According to embodiments of the present invention, it is possible to express the resized coefficient of the vertical coma as a function of the coefficients of primary, secondary, and tertiary coma. Consider the special case for $\varepsilon=0.8$, such as a 6 mm pupil constricts to 4.8 mm. From Table 2, we have $b_3^1 = G_3^0(\varepsilon)a_3^1 + G_3^1(\varepsilon)a_5^1 + G_3^2(\varepsilon)a_7^1$. Substituting the Zernike resizing polynomials from Table 3, we get $b_3^1 = \varepsilon^3 [a_3^1 - 2\sqrt{6}(1-\varepsilon^2)a_5^1 + 2\sqrt{2}(5-12\varepsilon^2+7\varepsilon^4)a_7^1]$. Similarly, for $b_3^{-1}$, we have $b_3^{-1} = \varepsilon^3 [a_3^{-1} - 2\sqrt{6}(1-\varepsilon^2)a_5^{-1} + 2\sqrt{2}(5-12\varepsilon^2+7\varepsilon^4)a_7^{-1}]$. Because $G_3^1(0.8) = -2\sqrt{6}(1-0.8^2) \times 0.8^3 = -0.903$, $G_3^2(0.8) = 2\sqrt{2}(5-12 \times 0.8^2 + 7 \times 0.8^4) \times 0.8^3 = 0.271$, and $G_3^3(0.8) = -2\sqrt{10}(5-21 \times 0.8^2 + 28 \times 0.8^4 - 12 \times 0.8^6) \times 0.8^3 = -0.379$, we find $b_3^1 = 0.8^3 a_3^1 - 0.903 a_5^1 + 0.271 a_7^1 - 0.379 a_9^1) = 0.512 a_3^1 - 0.903 a_5^1 + 0.27 a_7^1 - 0.379 a_9^1$. Similarly, $b_3^{-1} = 0.512 a_3^{-1} - 0.903 a_5^{-1} + 0.271 a_7^{-1} 0.379 a_9^{-1}$.

Table 3 shows Zernike resizing polynomials up to the 10th order.

TABLE 3

| n | i | $G_n^i(\varepsilon)$ |
|---|---|---|
| 0 | 1 | $-\sqrt{3}(1 - \varepsilon^2)$ |
| 0 | 2 | $\sqrt{5}(1 - 3\varepsilon^2 + 2\varepsilon^4)$ |
| 0 | 3 | $-\sqrt{7}(1 - 6\varepsilon^2 + 10\varepsilon^4 - 5\varepsilon^6)$ |
| 0 | 4 | $\sqrt{9}(1 - 10\varepsilon^2 + 30\varepsilon^4 - 35\varepsilon^6 + 14\varepsilon^8)$ |
| 0 | 5 | $-\sqrt{11}(1 - 15\varepsilon^2 + 70\varepsilon^4 - 140\varepsilon^6 + 126\varepsilon^8 - 42\varepsilon^{10})$ |
| 1 | 1 | $-2\sqrt{2}\varepsilon(1 - \varepsilon^2)$ |
| 1 | 2 | $\sqrt{3}\varepsilon(3 - 8\varepsilon^2 + 5\varepsilon^4)$ |
| 1 | 3 | $-4\varepsilon(2 - 10\varepsilon^2 + 15\varepsilon^4 - 7\varepsilon^6)$ |
| 1 | 4 | $\sqrt{5}\varepsilon(5 - 40\varepsilon^2 + 105\varepsilon^4 - 112\varepsilon^6 + 42\varepsilon^8)$ |
| 2 | 1 | $-\sqrt{15}\varepsilon^2 (1 - \varepsilon^2)$ |
| 2 | 2 | $\sqrt{21}\varepsilon^2 (2 - 5\varepsilon^2 + 3\varepsilon^4)$ |
| 2 | 3 | $-\sqrt{3}\varepsilon^2 (10 - 45\varepsilon^2 + 63\varepsilon^4 - 28\varepsilon^6)$ |
| 2 | 4 | $\sqrt{33}\varepsilon^2 (5 - 35\varepsilon^2 + 84\varepsilon^4 - 84\varepsilon^6 + 30\varepsilon^8)$ |
| 3 | 1 | $-2\sqrt{6}\varepsilon^3 (1 - \varepsilon^2)$ |
| 3 | 2 | $2\sqrt{2}\varepsilon^3 (5 - 12\varepsilon^2 7\varepsilon^4)$ |
| 3 | 3 | $-2\sqrt{10}\varepsilon^3 (5 - 21\varepsilon^2 + 28\varepsilon^4 - 12\varepsilon^6)$ |
| 4 | 1 | $-\sqrt{35}\varepsilon^4 (1 - \varepsilon^2)$ |
| 4 | 2 | $3\sqrt{5}\varepsilon^4 (3 - 7\varepsilon^2 + 4\varepsilon^4)$ |
| 4 | 3 | $-\sqrt{55}\varepsilon^4 (7 - 28\varepsilon^2 + 36\varepsilon^4 - 15\varepsilon^6)$ |
| 5 | 1 | $-4\sqrt{3}\varepsilon^5 (1 - \varepsilon^2)$ |
| 5 | 2 | $\sqrt{15}\varepsilon^5 (1 - 16\varepsilon^2 + 9\varepsilon^4)$ |
| 6 | 1 | $-3\sqrt{7}\varepsilon^6 (1 - \varepsilon^2)$ |
| 6 | 2 | $\sqrt{77}\varepsilon^6 (4 - 9\varepsilon^2 + 5\varepsilon^4)$ |
| 7 | 1 | $-4\sqrt{5}\varepsilon^7 (1 - \varepsilon^2)$ |
| 8 | 1 | $-3\sqrt{11}\varepsilon^8 (1 - \varepsilon^2)$ |

Figure 9A:
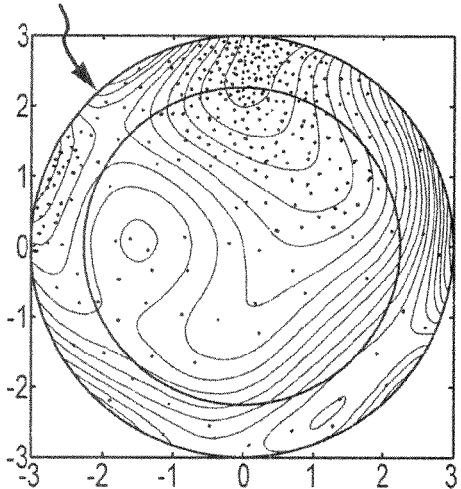
FIGS. 9A and 9B show exemplary illustrations of wavefront maps for a human eye, according to embodiments of the present invention.
Figure 9B:
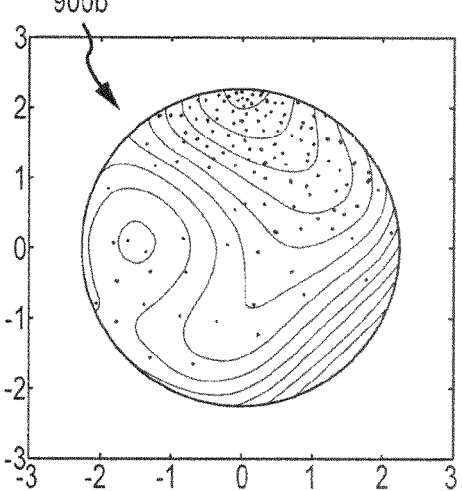

Table 4 shows a set of Zernike coefficients and the corresponding resized Zernike coefficients when a pupil resizing ratio of 0.75 is assumed. The original wavefront map 900a shown in FIG. 9A and the resized wavefront map 900b shown in FIG. 9B correspond to Zernike coefficients listed in Table 4. The resized wavefront appears identical to the inner part of the original wavefront within the new pupil size. Table 4 shows Zernike coefficients before ($a_n^m$) and after ($b_n^m$) pupil constriction ($\varepsilon=0.75$).

TABLE 4

| i | n | m | $a_n^m$ | $b_n^m$ |
|---|---|---|---|---|
| 0 | 0 | 0 | 0.8724 | 0.5849 |
| 1 | 1 | -1 | -0.6983 | -0.5119 |
| 2 | 1 | 1 | 0.1979 | -0.1070 |
| 3 | 2 | -2 | -0.1216 | -0.2145 |
| 4 | 2 | 0 | 0.3600 | 0.1197 |
| 5 | 2 | 2 | 0.2358 | 0.2308 |
| 6 | 3 | -3 | 0.0624 | 0.0140 |
| 7 | 3 | -1 | -0.0023 | -0.0831 |
| 8 | 3 | 1 | 0.2665 | 0.1814 |
| 9 | 3 | 3 | 0.1608 | -0.0546 |
| 10 | 4 | -4 | 0.0725 | -0.0324 |
| 11 | 4 | 2 | 0.1590 | 0.0376 |
| 12 | 4 | 0 | 0.0801 | 0.0404 |
| 13 | 4 | 2 | -0.0790 | -0.0781 |
| 14 | 4 | 4 | -0.0841 | -0.0597 |
| 15 | 5 | -5 | -0.0635 | -0.0151 |
| 16 | 5 | -3 | 0.0136 | 0.0032 |
| 17 | 5 | -1 | 0.0908 | 0.0215 |
| 18 | 5 | 1 | -0.0763 | -0.0181 |
| 19 | 5 | 3 | 0.1354 | 0.0321 |
| 20 | 5 | 5 | 0.0227 | 0.0054 |

TABLE 4-continued

| i | n | m | $a_n^m$ | $b_n^m$ |
|---|---|---|---|---|
| 21 | 6 | −6 | −0.0432 | −0.0077 |
| 22 | 6 | −4 | 0.0676 | 0.0120 |
| 23 | 6 | −2 | 0.0155 | 0.0028 |
| 24 | 6 | 0 | −0.0184 | −0.0033 |
| 25 | 6 | 2 | 0.0649 | 0.0116 |
| 26 | 6 | 4 | 0.0404 | 0.0072 |
| 27 | 6 | 6 | 0.0842 | 0.0150 |

2.5 Effective Power and Correction of Presbyopia

Traditionally, the refractive power is referred to as the sphere and cylinder that best correct the refractive error of the human eye so as to achieve the best visual acuity. Therefore, the refractive power may be independent of pupil size. When high order aberrations exist, as discussed in Dai, G.-m., *J. Opt. Soc. Am. A*, 23:539-543 (2006), the refractive power may be pupil size dependent. The instantaneous refractive power that is dependent upon the pupil size can be termed effective power. For an ocular wavefront that is associated with the set of Zernike coefficients $\{a_i\}$, when the pupil constricts the new set of Zernike coefficients becomes $\{b_i\}$. Aspects of effective power are discussed in U.S. Patent Publication No. 2005/0270491.

The sphere, cylinder, and cylinder axis in the plus cylinder notation after the pupil constriction can be written as $$S = -\frac{4\sqrt{3}\, b_2^0}{\varepsilon^2 R^2} - \frac{2\sqrt{6}\,\sqrt{(b_2^{-2})^2 + (b_2^2)^2}}{\varepsilon^2 R^2}, \quad (20a)$$

$$C = \frac{4\sqrt{6}\,\sqrt{(b_2^{-2})^2 + (b_2^2)^2}}{\varepsilon^2 R^2}, \quad (20b)$$

$$\theta = \frac{1}{2}\tan^{-1}\left(\frac{b_2^{-2}}{b_2^2}\right). \quad (20c)$$

From Table 2, we have $$b_2^{-2} = \sum_{i=0}^{N/2-1} G_2^i(\varepsilon) a_{2(i+1)}^{-2}, \quad (21a)$$

$$b_2^0 = \sum_{i=0}^{N/2-1} G_2^i(\varepsilon) a_{2(i+1)}^0, \quad (21b)$$

$$b_2^2 = \sum_{i=0}^{N/2-1} G_2^i(\varepsilon) a_{2(i+1)}^2. \quad (21c)$$

Substituting Eq. (21) into Eq. (20), we have $$S = -\frac{4\sqrt{3}}{\varepsilon^2 R^2} \sum_{i=0}^{N/2-1} G_2^i(\varepsilon) a_{2(i+1)}^0 - C/2, \quad (22a)$$

$$C = -\frac{4\sqrt{6}}{\varepsilon^2 R^2} \left\{ \sum_{i=0}^{N/2-1} \sum_{i'+1}^{N/2-1} G_2^i(\varepsilon) G_2^{i'}(\varepsilon) \left[ a_{2(i+1)}^{-2} a_{2(i'+1)}^{-2} + a_{2(i+1)}^2 + a_{2(i'+1)}^2 \right] \right\}^{1/2}, \quad (22b)$$

$$\theta = \frac{1}{2}\tan^{-1}\left[\frac{\sum_{i=0}^{N/2-1} G_2^i(\varepsilon) a_{2(i+1)}^{-2}}{\sum_{i=0}^{N/2-1} G_2^i(\varepsilon) a_{2(i+1)}^2}\right]. \quad (22c)$$

Equations (22a), (22b), and (22c) can be combined to determine a refraction for a general resizing case.

For the first four orders of Zernike polynomials, or N=4, Eq. (22) can be written as $$S = -\frac{4\sqrt{3}}{R^2}\left[a_2^0 - \sqrt{15}(1-\varepsilon^2)a_4^0\right] - C/2, \quad (23a)$$

$$C = \frac{4\sqrt{6}}{\varepsilon^2 R^2}\left\{\begin{array}{c}(a_2^{-2})^2 + (a_2^2)^2 - 2\sqrt{15}(1-\varepsilon^2) \\ [a_2^{-2}a_4^{-2} + a_2^2 a_4^2] + \\ 15(1-\varepsilon^2)^2[(a_4^{-2})^2 + (a_4^2)^2]\end{array}\right\}^{1/2}, \quad (23b)$$

$$\theta = \frac{1}{2}\tan^{-1}\left[\frac{a_2^{-2} - \sqrt{15}(1-\varepsilon^2)a_4^{-2}}{a_2^2 - \sqrt{15}(1-\varepsilon^2)a_4^2}\right]. \quad (23c)$$

Table 5 shows Zernike coefficients before the pupil constriction for a 6 mm pupil (R=3 mm).

TABLE 5

| Zernike index i | n | m | $a_n^m$ |
|---|---|---|---|
| 3 | 2 | −2 | 2.315 |
| 4 | 2 | 0 | 3.630 |
| 5 | 2 | 2 | −1.288 |
| 11 | 4 | −2 | 0.075 |
| 12 | 4 | 0 | −0.230 |
| 13 | 4 | 2 | −0.158 |
| 23 | 6 | −2 | 0.042 |
| 24 | 6 | 0 | 0.089 |
| 25 | 6 | 2 | −0.012 |

Table 6 shows wavefront refractions over different pupil sizes.

TABLE 6

| Pupil size (mm) | 6 | 5 | 4 | 3 | 2 | 1 | 0 |
|---|---|---|---|---|---|---|---|
| Sphere (D) | −1.35 | −1.65 | −1.97 | −2.27 | −2.52 | −2.67 | −2.73 |
| Cylinder (D) | −2.88 | −2.70 | −2.64 | −2.66 | −2.70 | −2.74 | −2.76 |
| Axis | 59.5° | 58.2° | 56.8° | 55.6° | 54.7° | 54.2° | 54.0° |

For the minus cylinder notation, Eqs. (22) and (23) can be modified accordingly by changing the sign of C from plus to minus.

Equation (22), and Eq. (23) as a special case, indicate that the spherical equivalent (S+C/2) can depend upon defocus, primary, secondary, tertiary, and other higher order spherical aberrations of the original wavefront when the pupil size constricts. Similarly, the cylinder can depend upon the primary, secondary, tertiary, and other higher order astigmatism of the original wavefront when the pupil size constricts.

According to embodiments of the present invention, it is possible to calculate the sphere, cylinder, and cylinder axis in the minus cylinder notation as a function of the pupil size for the Zernike coefficients shown in Table 5.

Figure 10:
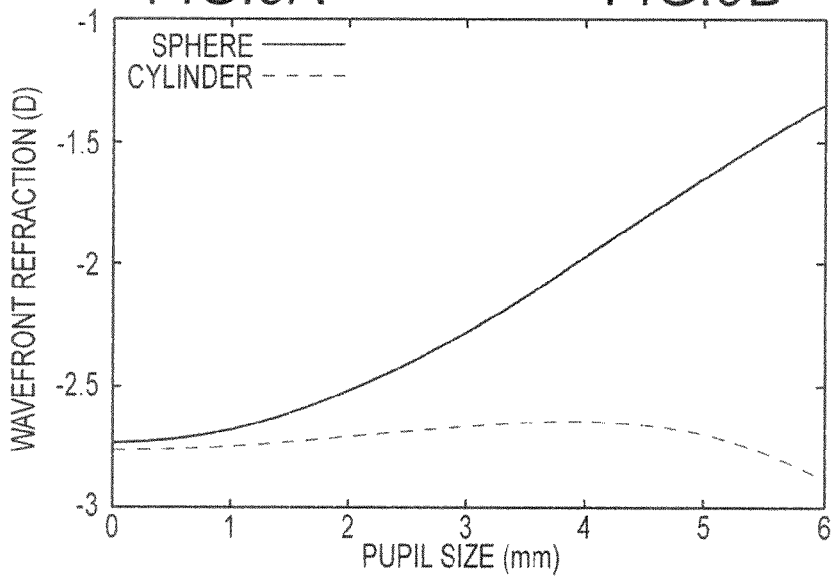
FIG. 10 shows a graph of effective power curves for sphere and cylinder as a function of pupil size, according to embodiments of the present invention.

For the cylinder, we have $C=-(4\sqrt{6}/3^2)\{[2.315-\sqrt{15}(1-\varepsilon^2)\times 0.075+\sqrt{21}(2-5\varepsilon^2+3\varepsilon^4)\times 0.042]^2+[-1.288-$ $\sqrt{15}(1-\epsilon^2)\times(-0.158)+\sqrt{21}(2-5\epsilon^2+3\epsilon^4)\times(-0.012)]^2\}^{1/2}$,
$S=-(4\sqrt{3}/3^2)[3.630-\sqrt{15}(1-\epsilon^2)\times(-0.230)+$
$\sqrt{21}(2-5\epsilon^2+3\epsilon^4)\times0.089]-C/2.$     $\theta=\tan^{-1}\{[2.315-$
$\sqrt{15}(1-\epsilon^2)\times0.075+\sqrt{21}(2-5\epsilon^2+3\epsilon^4)\times0.042]/[-1.288-$
$\sqrt{15}(1-\epsilon^2)\times(-0.158)+\sqrt{21}(2-5\epsilon^2+3\epsilon^4)\times(-0.012)]\}\times90/\pi.$ Applying $\epsilon$ from 6 to 0, we obtain the respective values of the sphere, the cylinder, and the cylinder axis, as shown in Table 6. FIG. 10 shows effective power curves for sphere and cylinder as a function of pupil size. In some embodiments, FIG. 10 shows effective power curves of the sphere and cylinder when the values of $\epsilon$ are continuous.

The power curves of the sphere and cylinder as a function of the pupil size can be useful for the correction of presbyopia, as the pupil size constricts during accommodation. Aspects of this feature are described in Lowenfeld, I. E., *The Pupil: Anatomy, Physiology, and Clinical Applications*, Butterworth-Heinemann, Boston (1999). A sphere power curve as shown in FIG. 10 may make the eye more myopic when the pupil constricts.

Suppose an emmetropic subject needs a presbyopic correction so he remains emmetropic when the pupil size is 4.5 mm but becomes −1.5 D myopic when the pupil constricts to 2.25 mm. It is possible to determine the amount of spherical aberration at 4.5 mm necessary to achieve that. The subject is emmetropic so he does not have cylinder error, or C=0. From Eq. (23), we obtain $S=-(4\sqrt{3}/2.25^2)[a_2^0-\sqrt{15}(1-\epsilon^2)a_4^0]$. When the pupil size is 4.5 mm, the subject remains emmetropic. Therefore, for $\epsilon=1$, $S=-(4\sqrt{3}/2.25^2)a_2^0=0$, or $a_2^0=0$. For $\epsilon=2.25/4.5=0.5$, the subject wants to achieve −1.5 D. That means $S=-(4\sqrt{3}/2.25^2)(-\sqrt{15})[1-(½)^2]a_4^0=-1.5$, or $a_4^0=-0.38$ μm. Hence, if we introduce 0.38 microns of negative spherical aberration to the eye, this subject can have a manifest refraction of −1.5 D at 2.25 mm pupil even though his manifest refraction is zero at 4.5 mm.

2.6 Pupil Resizing with Seidel Series

The set of Seidel series is a set of basis functions for describing optical aberrations. Although this set of basis functions may not be practical in all circumstances for ocular aberration representation because most ocular aberrations are not symmetric, it is useful to test pupil resizing embodiments described herein. Seidel series typically require x-axis rotational symmetry, and in normal aberrations such rotational symmetry is not observed. Nonetheless, Seidel series may be used because it represents a classical aberration.

Table 7 shows Seidel coefficients before ($a_n^m$) and after ($b_n^m$) pupil constriction ($\epsilon=0.85$).

TABLE 7

| i | n | m | $a_n^m$ | $b_n^m$ |
|---|---|---|---------|---------|
| 0 | 0 | 0 | −0.3386 | −0.3386 |
| 1 | 1 | 1 | 0.4501 | 0.3252 |
| 2 | 2 | 0 | −0.2689 | −0.1943 |
| 3 | 2 | 2 | 0.0712 | 0.0437 |
| 4 | 3 | 1 | −0.0093 | −0.0057 |
| 5 | 3 | 3 | 0.1956 | 0.1021 |
| 6 | 4 | 0 | 0.1310 | 0.0684 |
| 7 | 4 | 2 | −0.0218 | −0.0114 |
| 8 | 4 | 4 | −0.1926 | −0.0855 |
| 9 | 5 | 1 | 0.1286 | 0.0571 |
| 10 | 5 | 3 | −0.0221 | −0.0098 |
| 11 | 5 | 5 | 0.0385 | 0.0145 |
| 12 | 6 | 0 | 0.0973 | 0.0367 |
| 13 | 6 | 2 | 0.1406 | 0.0530 |
| 14 | 6 | 4 | 0.0794 | 0.0299 |
| 15 | 6 | 6 | −0.0925 | −0.0297 |

A Seidel series can be expressed as $$s_n^m(\rho,\theta)=\rho^n \cos^m \theta. \quad (24)$$

Since often Seidel radial polynomials are exactly the same as the radial polynomials in Taylor monomials, it can shown that the set of the pupil resizing polynomials is the same as in Taylor monomials as $$L_n(\epsilon)=\epsilon^n. \quad (25)$$

Hence, similar to Taylor monomials, each new Seidel coefficient can be scaled by $\epsilon^n$ where n is the radial order of the Seidel series. Equation (25) can represent the GPRF of a Seidel series.

Table 7 shows a set of Seidel coefficients and the corresponding resized Seidel coefficients when a pupil resizing ratio of 0.85 is assumed. The original wavefront map 1100*a* shown in FIG. 11A and the resized wavefront map 1100*b* shown in FIG. 11B correspond to Seidel coefficients listed in Table 7. The resized wavefront appears identical to the inner part of the original wavefront within the new pupil size. As can be seen from FIGS. 11A and 11B, the wavefront can be symmetric with respect to the x-axis. In some embodiments, the set of Seidel series may not be applicable to ocular wavefront representation.

3. Wavefront Representation for Cyclorotation

The ocular wavefront representation for cyclorotation can be considered in vision correction because human eyes have three degrees of freedom in rotational eye movements, as discussed in Chernyak, D. A., *J. Cataract. Refract. Surg.*, 30:633-638 (2004). This is also shown in FIGS. 12A to 12C, where FIG. 12A represents cyclorotation and FIGS. 12B and 12C represent pupil center shift. FIG. 12A shows an eye 1200*a*, having a pupil 1205*a*, rotating about a longitudinal axis 1210*a*. FIG. 12B shows an eye 1200*b*, having a pupil 1205*b*, rotating about a longitudinal axis 1210*b*. FIG. 12C shows an eye 1200*c*, having a pupil 1205*c*, rotating about a longitudinal axis 1210*c*. In this section, the cyclorotation of ocular wavefront maps is discussed. The pupil center shift caused by the eye movement is discussed in the next section. It is possible to evoke the directional or linear eye tracking, aspects of which are discussed in Yee, K. "*Active eye tracking for excimer laser refractive surgery*," in Aberration-Free Refractive Surgery, 2nd ed., J. Bille, C. F. H. Hamer, and F. H. Loesel, eds. (Springer, 2003), pp. 125-140, or the cyclotorsional eye tracking, aspects of which are discussed in Chernyak, D. A., *IEEE Trans. Bio. Eng.*, 52:2032-2040 (2005), during laser refractive surgery.

FIG. 13 shows the coordinates of a wavefront 1300 before (solid lines) and after (dashed lines) cyclorotation of the wavefront by an angle $\phi$. In some embodiments, a counter clockwise angle can be defined as positive. A relation between the coordinates can be given in the following equation.

$$x'=x \cos \phi + y \sin \phi, \quad (26)$$

$$y'=-x \sin \phi + y \cos \phi. \quad (26b)$$

3.1 Wavefront Rotation with Taylor Monomials

For the wavefront rotation with Taylor monomials, it can be shown (Appendix B) that the Taylor coefficients after the rotation are related to the original Taylor coefficients by $$b_p^q = \sum_{k=0}^{q} \sum_{l=0}^{p-q} \frac{(-1)^k q!(p-q)!}{k!l!(q-k)!(p-q-l)!}(\sin\phi)^{k+l}(\cos\phi)^{p-k-l}a_p^{q-k+l}. \quad (27)$$

Table 8 lists the conversion formulas for an original set of Taylor coefficients to a new set of Taylor coefficients when a cyclorotation of the wavefront map by an angle φ counter clockwise occurs. As shown here, Taylor coefficients of a rotated wavefront $b_i$ can be represented as a function of the original Taylor coefficients $a_i$ for $p \leq 5$.

TABLE 8

| p | q | Formula |
|---|---|---------|
| 0 | 0 | $b_0 = a_0$ |
| 1 | 0 | $b_1 = a_1 \cos\phi + a_2 \sin\phi$ |
| 1 | 1 | $b_2 = -a_1 \sin\phi + a_2 \cos\phi$ |
| 2 | 0 | $b_3 = a_3 \cos^2\phi + 2a_4 \sin\phi \cos\phi + a_5 \sin^2\phi$ |
| 2 | 1 | $b_4 = -a_3 \sin\phi \cos\phi + a_4(\cos^2\phi - \sin^2\phi) + a_5 \sin\phi \cos\phi$ |
| 2 | 2 | $b_5 = a_3 \sin^2\phi - 2a_4 \sin\phi \cos\phi + a_5 \cos^2\phi$ |
| 3 | 0 | $b_6 = a_6 \cos^3\phi + 3a_7 \cos^2\phi \sin\phi + 3a_8 \cos\phi \sin^2\phi + a_9 \sin^3\phi$ |
| 3 | 1 | $b_7 = -a_6 \cos^2\phi \sin\phi + a_7(\cos^2\phi - 2\sin^2\phi)\cos\phi + a_8(2\cos^2\phi - \sin^2\phi)\sin\phi + a_9 \cos\phi \sin^2\phi$ |
| 3 | 2 | $b_8 = a_6 \cos\phi \sin^2\phi - a_7(2\cos^2\phi - \sin^2\phi)\sin\phi + a_8(\cos^2\phi - 2\sin^2\phi)\cos\phi + a_9 \cos^2\phi \sin\phi$ |
| 3 | 3 | $b_9 = -a_6 \sin^3\phi + 3a_7 \cos\phi \sin^2\phi - 3a_8 \cos^2\phi \sin\phi + a_9 \cos^3\phi$ |
| 4 | 0 | $b_{10} = a_{10} \cos^4\phi + 4a_{11} \cos^3\phi \sin\phi + 6a_{12} \cos^2\phi \sin^2\phi + 4a_{13} \cos\phi \sin^3\phi + a_{14} \sin^4\phi$ |
| 4 | 1 | $b_{11} = -a_{10} \cos\phi \sin\phi + a_{11} \cos\phi (\cos^2\phi - 3\sin^2\phi) + 3a_{12} \sin\phi \cos\phi (\cos^2\phi - \sin^2\phi) + a_{13} \sin^2\phi (3\cos^2\phi - \sin^2\phi) + a_{14} \sin^3\phi \cos\phi$ |
| 4 | 2 | $b_{12} = a_{10} \sin^2\phi \cos^2\phi - 2a_{11} \sin\phi \cos\phi (\cos^2\phi - \sin^2\phi) + a_{12} \sin^2\phi (4\cos^2\phi + \sin^2\phi) + 2a_{13} \sin\phi \cos\phi (\cos^2\phi - \sin^2\phi) + a_{14} \sin^2\phi \cos^2\phi$ |
| 4 | 3 | $b_{13} = -a_{10} \sin^3\phi \cos\phi + a_{11} \sin^2\phi (3\cos^2\phi - \sin^2\phi) - 3a_{12} \sin\phi \cos\phi (\cos^2\phi - \sin^2\phi) + a_{13} \cos^2\phi (\cos^2\phi - 3\sin^2\phi) + a_{14} \sin\phi \cos^3\phi)$ |
| 4 | 4 | $b_{14} = a_{10} \sin^4\phi - 4a_{11} \sin^3\phi \cos\phi + 6a_{12} \sin^2\phi \cos^2\phi - 4a_{13} \sin\phi \cos^3\phi + a_{14} \cos^4\phi$ |
| 5 | 0 | $b_{15} = a_{15} \cos^5\phi + 5a_{16} \sin\phi \cos^4\phi + 10a_{17} \sin^2\phi \cos^3\phi + 10a_{18} \sin^3\phi \cos^2\phi + 5a_{19} \sin^4\phi \cos\phi + a_{20} \sin^5\phi$ |
| 5 | 1 | $b_{16} = -a_{15} \sin\phi \cos^4\phi + a_{16} \cos^3\phi (\cos^2\phi - 4\sin^2\phi) + 2a_{17} \sin\phi \cos^2\phi (2\cos^2\phi - 3\sin^2\phi) + 2a_{18} \sin^2\phi \cos\phi (3\cos^2\phi - 2\sin^2\phi) + a_{19} \sin^3\phi (4\cos^2\phi - \sin^2\phi) + a_{20} \sin^4\phi \cos\phi$ |
| 5 | 2 | $b_{17} = a_{15} \sin^2\phi \cos^3\phi - a_{16} \sin\phi \cos^2\phi (2\cos^2\phi - 3\sin^2\phi) + a_{17} \cos\phi (\cos^4\phi - 6\sin^2\phi \cos^2\phi + 3\sin^4\phi) + a_{18} \sin\phi (3\cos^4\phi - 6\sin^2\phi \cos^2\phi + \sin^4\phi) + a_{19} \sin^2\phi \cos\phi (3\cos^2\phi - 2\sin^2\phi) + a_{20} \sin^3\phi \cos^2\phi$ |
| 5 | 3 | $b_{18} = a_{15} \sin^3\phi \cos^2\phi + a_{16} \sin^2\phi \cos\phi (3\cos^2\phi - 2\sin^2\phi) - a_{17} \sin\phi (3\cos^4\phi - 6\sin^2\phi \cos^2\phi + \sin^4\phi) + a_{18} \cos\phi (3\sin^4\phi - 6\sin^2\phi \cos^2\phi + \cos^4\phi) + a_{19} \sin\phi \cos^2\phi (2\cos^2\phi - 3\sin^2\phi) + a_{20} \sin^2\phi \cos^3\phi$ |
| 5 | 4 | $b_{19} = a_{15} \sin^4\phi \cos\phi + a_{16} \sin^3\phi (\sin^2\phi - 4\cos^2\phi) + 2a_{17} \sin^2\phi \cos\phi (3\cos^2\phi - 2\sin^2\phi) - 2a_{18} \sin\phi \cos^2\phi (2\cos^2\phi - 3\sin^2\phi) - a_{19} \cos^3\phi (4\sin^2\phi - \cos^2\phi) + a_{20} \sin\phi \cos^4\phi$ |
| 5 | 5 | $b_{20} = -a_{15} \sin^5\phi + 5a_{16} \phi \sin^4\phi \cos\phi - 10a_{17} \sin^3\phi \cos^2\phi + 10a_{18} \sin^2\phi \cos^3\phi - 5a_{19} \sin\phi \cos^4\phi + a_{20} \cos^5\phi$ |

Because the radial order of both $a_p^{q-k+1}$ and $b_p^q$ is p, Eq. (27) indicates that Taylor coefficients after cyclorotation can be affected by those in the same order. For example, $b_3$, $b_4$, and $b_5$ can be affected by $a_3$, $a_4$, and $a_5$ because they are in the same radial order. Similarly, $b_{10}$ to $b_{14}$ can be affected by $a_{10}$ to $a_{14}$ because they are also in the same order. Table 8 confirms this observation.

As an example, Table 9 shows a list of Taylor coefficients of an original wavefront and the corresponding Taylor coefficients of the wavefront when it rotates by 90°, 180°, and 270°, respectively. The corresponding wavefront maps 1400a, 1400b, 1400c, and 1440d, are shown in FIGS. 14A to 14D, respectively. As can be seen from these maps, the features of the maps are rotated by the respective angles. FIG. 14A shows the original wavefront map. FIG. 14B shows the rotated map after 90° rotation. FIG. 14C shows the rotated map after 180° rotation. FIG. 14D shows the rotated map after 270° rotation.

It should be noted that when the rotational angle is not a multiple of 90°, error can occur when the wavefront is digitized, or sampled. This is because the formulas shown in Table 8 are analytical and correspond to a smooth wavefront with infinite sampling. With Taylor monomials, because of the power in the triangular functions, any error can be amplified. Therefore, according to some embodiments the set of Taylor monomials may not be ideal for the study of the wavefront rotation. Table 9 shows an example of the wavefront rotation with Taylor coefficients for the original and the rotated wavefronts after various rotation angles.

TABLE 9

| I | p | q | Original | 90° | 180° | 270° |
|---|---|---|----------|------|------|------|
| 0 | 0 | 0 | 1.6524 | 1.6524 | 1.6524 | 1.6524 |
| 1 | 1 | 0 | -1.7143 | 0.5963 | 1.7143 | -0.5963 |
| 2 | 1 | 1 | 0.5963 | 1.7143 | -0.5963 | -1.7143 |
| 3 | 2 | 0 | -4.0792 | -1.7784 | -4.0792 | -1.7784 |
| 4 | 2 | 1 | -6.3573 | 6.3573 | -6.3573 | 6.3573 |
| 5 | 2 | 2 | -1.7784 | -4.0792 | -1.7784 | -4.0792 |
| 6 | 3 | 0 | 5.5547 | -5.8774 | -5.5547 | 5.8774 |
| 7 | 3 | 1 | -5.2032 | -1.1222 | 5.2032 | 1.1222 |
| 8 | 3 | 2 | 1.1222 | -5.2032 | -1.1222 | 5.2032 |
| 9 | 3 | 3 | -5.8774 | -5.5547 | 5.8774 | 5.5547 |
| 10 | 4 | 0 | 11.3340 | 4.4274 | 11.3340 | 4.4274 |
| 11 | 4 | 1 | 8.7331 | -22.8555 | 8.7331 | -22.8555 |
| 12 | 4 | 2 | 1.6505 | 1.6505 | 1.6505 | 1.6505 |
| 13 | 4 | 3 | 22.8555 | -8.7331 | 22.8555 | -8.7331 |
| 14 | 4 | 4 | 4.4274 | 11.3340 | 4.4274 | 11.3340 |
| 15 | 5 | 0 | -3.5909 | 4.9062 | 3.5909 | -4.9062 |
| 16 | 5 | 1 | 5.9912 | 1.2298 | -5.9912 | -1.2298 |
| 17 | 5 | 2 | 5.8266 | 6.2527 | -5.8266 | -6.2527 |
| 18 | 5 | 3 | 6.2527 | -5.8266 | -6.2527 | 5.8266 |
| 19 | 5 | 4 | -1.2298 | 5.9912 | 1.2298 | -5.9912 |
| 20 | 5 | 5 | 4.9062 | 3.5909 | -4.9062 | -3.5909 |
| 21 | 6 | 0 | -10.3417 | -3.4241 | -10.3417 | -3.4241 |
| 22 | 6 | 1 | -6.2927 | 17.9847 | -6.2927 | 17.9847 |
| 23 | 6 | 2 | -11.4756 | -6.2223 | -11.4756 | -6.2223 |
| 24 | 6 | 3 | -21.4397 | 21.4397 | -21.4397 | 21.4397 |
| 25 | 6 | 4 | -6.2223 | -11.4756 | -6.2223 | -11.4756 |
| 26 | 6 | 5 | -17.9847 | 6.2927 | -17.9847 | 6.2927 |
| 27 | 6 | 6 | -3.4241 | -10.3417 | -3.4241 | -10.3417 |

3.2 Wavefront Rotation with Zernike Polynomials

Many refractive laser companies use Zernike polynomial represented ocular wavefronts to drive customized laser vision correction. Embodiments of the present invention provide systems and methods for determining new Zernike coefficients based on an original set when a cyclorotation of the wavefront occurs during a vision correction or treatment procedure. For example, a patient's ocular wavefront is measured with an aberrometer. However, during the refractive laser ablation, the patient's eye may exhibit a cyclotorsional movement. The treatment or ablated shape therefore may not exactly land on the location as intended, but instead may be rotated by a certain angle. This would lead to a residual wavefront error that is not zero, hence affecting the visual outcome after the correction or treatment.

From the definition of Zernike polynomials, it can be shown (Appendix C) that the new Zernike coefficients are related to the original Zernike coefficients of the same radial degree n and the absolute value of the azimuthal frequency m as $$b_n^{-|m|} = a_n^{-|m|} \cos|m|\phi + a_n^m \sin|m|\phi, \qquad (28a)$$

$$b_n^{|m|} = -a_n^{-|m|} \sin|m|\phi + a_n^{|m|} \cos|m|\phi. \qquad (28b)$$

Equations (28a) and (28b) represent the Zernike formulas. It is understood that the cylinder axis can be represented by the original axis offset by a rotational angle difference, and sphere and cylinder can be the same as the original. Hence, if cylinder is present and rotation occurs, the magnitude of the sphere and cylinder remains the same and the angle of cylinder axis changes. Thus, the refraction can be the same, except the angle will be changed. When combining decentration, rotation, and constriction, then the refraction may change due to the combination of changes, but when considering rotation only, then refraction may not change, except for the angle of rotation. Table 8 shows the conversion formulas for calculating the new Zernike coefficients $b_i$ from the original set $a_i$ when an angle $\phi$ of rotation counter clockwise happens. Because $Z_0$, $Z_4$, $Z_{12}$, and $Z_{24}$ are rotationally symmetric, their corresponding coefficients may not change with respect to the rotation.

Some have suggested a vector representation for Zernike polynomials. See, for example, Campbell, C. E., *Optom. Vis. Sci.*, 80:79-83 (2003). Zernike polynomials can be written as $$Z_n^m(\rho,\theta;\alpha) = \sqrt{2-\delta_{m0}} \, \mathfrak{R}_n^{|m|}(\rho)\cos[m(\theta-\alpha)] \quad (29)$$

where the coefficient that combines the two symmetric Zernike terms $Z_n^m$ and $Z_n^{-m}$ can be calculated as $$c_{n,m} = \sqrt{(c_n^{-m})^2 + (c_n^m)^2}, \quad (30)$$

and the direction of the vector a can be calculated by $$\alpha = \frac{1}{|m|}\tan^{-1}\left(\frac{c_n^{-|m|}}{c_n^{|m|}}\right). \quad (31)$$

With this new representation, the rotation of the wavefront map can be represented easily. The magnitude of the coefficient $c_{n,m}$ does not change, but the direction of the vector $\alpha$ simply becomes $\alpha-\phi$ where $\phi$ is the angle of the wavefront rotation.

According to embodiments of the present invention, an ocular wavefront may contain 0.5 μm of horizontal coma and −0.25 μm of vertical coma. If this ocular wavefront map is rotated by 37° clockwise, the new horizontal and vertical coma can be determined. The horizontal coma $a_3^1 = a_8 = 0.5$ and the vertical coma $a_3^{-1} = a_7 = 0.25$. Rotating 37° clockwise means 360°−37°=323° counterclockwise, or $\phi$=323°. From Table 10 we have $b_7 = a_7 \cos(323°) + a_8 \sin(323°) = -0.25 \cos(323°) + 0.5 \sin(323°) = -0.501$, $b_8 = -a_7 \sin(323°) + a_8 \cos(323°) = -0.25 \sin(323°) + 0.5 \cos(323°) = 0.249$. Therefore, after the rotation, the horizontal coma becomes 0.249 μm and the vertical coma becomes −0.501 μm. If we use the vector representation, the combined coma is $\sqrt{a_7^2 + a_8^2} = \sqrt{0.5^2 + (-0.25)^2} = 0.559$ μm and the direction angle is $a = \tan^{-1}(a_7/a_8) = \tan^{-1}(-0.25/0.5) = 153°$. After the rotation, the coma is $\sqrt{b_7^2 + b_8^2} = \sqrt{0.249^2 + (-0.501)^2} = 0.559$ μm and the direction angle is $a = \tan^{-1}(b_7/b_8) = \tan^{-1}(-0.501/0.249) = 116°$. The new angle a is 37° less than the original angle, meaning that the map is rotated by 37° clockwise. Table 10 shows Zernike coefficients of the rotated wavefront $b_i$ as a function of the original Zernike coefficients $a_i$ for $n \leq 7$.

TABLE 10

| n | m | Formula |
|---|---|---------|
| 0 | 0 | $b_0 = a_0$ |
| 1 | −1 | $b_1 = a_1 \cos \phi + a_2 \sin \phi$ |
| 1 | 1 | $b_2 = -a_1 \sin \phi + a_2 \cos \phi$ |
| 2 | −2 | $b_3 = a_3 \cos 2\phi + a_5 \sin 2\phi$ |
| 2 | 0 | $b_4 = a_4$ |
| 2 | 2 | $b_5 = -a_3 \sin 2\phi + a_5 \cos 2\phi$ |
| 3 | −3 | $b_6 = a_6 \cos 3\phi + a_9 \sin 3\phi$ |

TABLE 10-continued

| n | m | Formula |
|---|---|---------|
| 3 | −1 | $b_7 = a_7 \cos \phi + a_8 \sin \phi$ |
| 3 | 1 | $b_8 = -a_7 \sin \phi + a_8 \cos \phi$ |
| 3 | 3 | $b_9 = -a_6 \sin 3\phi + a_9 \cos 3\phi$ |
| 4 | −4 | $b_{10} = a_{10} \cos 4\phi + a_{14} \sin 4\phi$ |
| 4 | −2 | $b_{11} = a_{11} \cos 2\phi + a_{13} \sin 2\phi$ |
| 4 | 0 | $b_{12} = a_{12}$ |
| 4 | 2 | $b_{13} = -a_{11} \sin 2\phi + a_{13} \cos 2\phi$ |
| 4 | 4 | $b_{14} = -a_{10} \sin 4\phi + a_{14} \cos 4\phi$ |
| 5 | −5 | $b_{15} = a_{15} \cos 5\phi + a_{20} \sin 5\phi$ |
| 5 | −3 | $b_{16} = a_{16} \cos 3\phi + a_{19} \sin 3\phi$ |
| 5 | −1 | $b_{17} = a_{17} \cos \phi + a_{18} \sin \phi$ |
| 5 | 1 | $b_{18} = -a_{17} \sin \phi + a_{18} \cos \phi$ |
| 5 | 3 | $b_{19} = -a_{16} \sin 3\phi + a_{19} \cos 3\phi$ |
| 5 | 5 | $b_{20} = -a_{15} \sin 5\phi + a_{20} \cos 5\phi$ |
| 6 | −6 | $b_{21} = a_{21} \cos 6\phi + a_{27} \sin 6\phi$ |
| 6 | −4 | $b_{22} = a_{22} \cos 4\phi + a_{26} \sin 4\phi$ |
| 6 | −2 | $b_{23} = a_{23} \cos 2\phi + a_{25} \sin 2\phi$ |
| 6 | 0 | $b_{24} = a_{24}$ |
| 6 | 2 | $b_{25} = -a_{23} \sin 2\phi + a_{25} \cos 2\phi$ |
| 6 | 4 | $b_{26} = -a_{22} \sin 4\phi + a_{26} \cos 4\phi$ |
| 6 | 6 | $b_{27} = -a_{21} \sin 6\phi + a_{27} \cos 6\phi$ |
| 7 | −7 | $b_{28} = a_{28} \cos 7\phi + a_{35} \sin 7\phi$ |
| 7 | −5 | $b_{29} = a_{29} \cos 5\phi + a_{34} \sin 5\phi$ |
| 7 | −3 | $b_{30} = a_{30} \cos 3\phi + a_{33} \sin 3\phi$ |
| 7 | −1 | $b_{31} = a_{31} \cos \phi + a_{32} \sin \phi$ |
| 7 | 1 | $b_{32} = -a_{31} \sin \phi + a_{32} \cos \phi$ |
| 7 | 3 | $b_{33} = -a_{30} \sin 3\phi + a_{33} \cos 3\phi$ |
| 7 | 5 | $b_{34} = -a_{29} \sin 5\phi + a_{34} \cos 5\phi$ |
| 7 | 7 | $b_{35} = -a_{28} \sin 7\phi + a_{35} \cos 7\phi$ |

As an example, FIGS. 15A to 15H show an ocular wavefront and the effect of the partial correction resulting from the cyclorotation of the eye during, e.g., a refractive laser surgery. Accordingly, these figures can illustrate an example for the wavefront rotation and its influence on vision correction or treatment. FIG. 15A shows an original wavefront map. If the wavefront 1500a is rotated by 3°, 12°, and 47°, respectively, the corresponding maps, 1550b, 1500c, and 1500d, are shown in FIGS. 15B, 15C, and 15D, respectively. If a cyclorotation of the eye occurs as in FIGS. 15A, 15B, 15C, and 15D while the vision correction or treatment is applied, the residual wavefront or the ocular aberrations that would leave without correction, is shown in FIGS. 15E, 15F, 15G, and 15H, respectively. Put differently, FIGS. 15A, 15B, 15C, and 15D illustrate wavefront contour maps for 0°, 3°, 12°, and 47° rotation, respectively, and FIGS. 15E, 15F, 15G, and 15H illustrate residual wavefront contour maps 1500e, 1500f, 1500g, and 1500h, for 0°, 3°, 12°, and 47° rotation, respectively, during vision treatment or correction. Corresponding Zernike coefficients are listed in Table 11.

Table 11 shows Zernike coefficients for the rotated wavefronts and for the residual wavefronts after a partial vision correction due to a cyclorotation of the eye, as shown in FIGS. 15A to 15H. The original wavefront without rotation corresponds to a typical moderate hyperopic eye with a 6 mm pupil. The residual RMS wavefront error as well as the residual high order RMS wavefront error for the partial correction are also shown. Note that the coefficients of all rotationally symmetric terms, such as $a_0$, $a_4$, $a_{12}$, and $a_{24}$, typically do not change after the rotation.

TABLE 11

|   |   |   | Rotated wavefronts | | | | Residual wavefronts | | |
|---|---|---|---|---|---|---|---|---|---|
| i | n | m | 0° | 3° | 12° | 47° | 3° | 12° | 47° |
| 0 | 0 | 0 | 0.1734 | 0.1734 | 0.1734 | 0.1734 | 0.0000 | 0.0000 | 0.0000 |
| 1 | 1 | −1 | 0.9003 | 0.8709 | 0.7688 | 0.2208 | −0.0294 | −0.1021 | −0.5480 |
| 2 | 1 | 1 | −0.5377 | −0.5841 | −0.7131 | −1.0251 | −0.0464 | −0.1290 | −0.3120 |
| 3 | 2 | −2 | 1.1068 | 1.1416 | 1.1703 | 0.3131 | 0.0348 | 0.0287 | −0.8572 |
| 4 | 2 | 0 | −3.0140 | −3.0140 | −3.0140 | −3.0140 | 0.0000 | 0.0000 | 0.0000 |
| 5 | 2 | 2 | 0.3913 | 0.2735 | −0.0927 | −1.1314 | −0.1178 | −0.3662 | −1.0387 |
| 6 | 3 | −3 | 0.1747 | 0.2061 | 0.2673 | −0.0009 | 0.0314 | 0.0612 | −0.2682 |
| 7 | 3 | −1 | −0.0290 | −0.0458 | −0.0951 | −0.2545 | −0.0168 | −0.0493 | −0.1594 |
| 8 | 3 | 1 | −0.3210 | −0.3190 | −0.3080 | −0.1977 | 0.0020 | 0.0110 | 0.1103 |
| 9 | 3 | 3 | 0.2143 | 0.1843 | 0.0707 | −0.2765 | −0.0300 | −0.1136 | −0.3472 |
| 10 | 4 | −4 | −0.0276 | −0.0022 | 0.0700 | 0.0108 | 0.0254 | 0.0722 | −0.0592 |
| 11 | 4 | −2 | 0.0577 | 0.0794 | 0.1385 | 0.2064 | 0.0217 | 0.0591 | 0.0679 |
| 12 | 4 | 0 | 0.1460 | 0.1460 | 0.1460 | 0.1460 | 0.0000 | 0.0000 | 0.0000 |
| 13 | 4 | 2 | 0.2109 | 0.2037 | 0.1692 | −0.0723 | −0.0072 | −0.0345 | −0.2415 |
| 14 | 4 | 4 | 0.1191 | 0.1222 | 0.1002 | −0.1218 | 0.0031 | −0.0220 | −0.2220 |
| 15 | 5 | −5 | −0.1295 | −0.0843 | 0.0716 | −0.0547 | 0.0452 | 0.1559 | −0.1263 |
| 16 | 6 | −3 | −0.0377 | −0.0429 | −0.0516 | 0.0067 | −0.0052 | −0.0087 | 0.0583 |
| 17 | 5 | −1 | 0.1742 | 0.1827 | 0.2051 | 0.2408 | 0.0085 | 0.0224 | 0.0357 |
| 18 | 5 | 1 | 0.1668 | 0.1575 | 0.1269 | −0.0136 | −0.0093 | −0.0306 | −0.1405 |
| 19 | 5 | 3 | −0.0359 | −0.0296 | −0.0069 | 0.0516 | 0.0063 | 0.0227 | 0.0585 |
| 20 | 5 | 5 | 0.1575 | 0.1857 | 0.1909 | −0.1964 | 0.0282 | 0.0052 | −0.3873 |
| 21 | 6 | −6 | −0.1474 | −0.1712 | −0.1410 | 0.0676 | −0.0238 | 0.0302 | 0.2086 |
| 22 | 6 | −4 | −0.0490 | −0.0685 | −0.1064 | 0.0623 | −0.0195 | −0.0379 | 0.1687 |
| 23 | 6 | −2 | 0.1044 | 0.0912 | 0.0464 | −0.1274 | −0.0132 | −0.0448 | −0.1738 |
| 24 | 6 | 0 | −0.1634 | −0.1634 | −0.1634 | −0.1634 | 0.0000 | 0.0000 | 0.0000 |
| 25 | 6 | 2 | −0.1204 | −0.1307 | −0.1525 | −0.0957 | −0.0103 | −0.0218 | 0.0568 |
| 26 | 6 | 4 | −0.0991 | −0.0867 | −0.0299 | 0.0913 | 0.0124 | 0.0568 | 0.1212 |
| 27 | 6 | 6 | −0.1004 | −0.0499 | 0.1092 | −0.1651 | 0.0505 | 0.1591 | −0.2743 |
| Residual RMS wavefront error | | | | | | | 0.1687 | 0.5013 | 1.7165 |
| Residual high order RMS wavefront error | | | | | | | 0.1017 | 0.2989 | 0.8573 |

Table 11 shows the Zernike coefficients of the original wavefront as well as the coefficients of the rotated wavefronts with different rotation angles. Also shown are the coefficients of the residual wavefronts assuming a partial correction of the original wavefront due to a cyclorotation the of the eye. To estimate how much error may induce due to the cyclorotation of the eye, the residual RMS wavefront error as well as the residual high order RMS wavefront error for each of the rotation angles is shown. For this typical eye, a rotation of 12° induces about the same amount of high order aberrations as a typical wavefront-driven refractive surgery.

To further demonstrate the visual influence of the error due to cyclorotation of the eye during the vision correction, FIGS. 16A to 16G show the point spread function of the residual wavefronts due to the partial correction and the residual wavefronts with high order aberrations. We assume in this case that the low order aberrations can be corrected with, e.g., a trial lens, so as to estimate the influence of the cyclorotation on the best corrected visual acuity. The corresponding simulated blurred 20/20 letter E images are also shown. The top row illustrates the point spread function and the bottom row illustrates the corresponding blurred 20/20 letter E for the wavefront maps shown in FIGS. 15A to 15H. Hence, FIGS. 16A to 16D refer to the residual wavefronts as shown in FIGS. 15E to 15H. Relatedly, FIGS. 16E to 16G refer to the residual wavefronts excluding the low orders for the wavefronts corresponding to FIGS. 15F to 15H. The field of view for all the images of 6'×6'. The Strehl ratios from FIGS. 15A to 15H are 1, 0.251, 0.045, 0.006, 0.449, 0.105, and 0.009, respectively.

4 Wavefront Representation for Decentration

As discussed in Section 3 above, rotational eye movement can cause both cyclorotation and decentration of ocular wavefront maps. In this section, the representation of the decentration of ocular wavefronts and its effect on the visual outcomes is discussed. Some have proposed approximation techniques for decentration. For example, some have proposed approximations to the first order of a Taylor expansion, for instances where translation is minimal. Embodiments of the present invention provide precise determinations of decentration, regardless of the amount of shift or decentration present.

4.1 Wavefront Extrapolation.

When the pupil moves, some part of the known wavefront can move out of the pupil, and some part of the wavefront can move into the pupil. However, the part of the wavefront that moves into the pupil can be originally unknown because it may not be defined. This leaves us with one certain solution that a smaller pupil is used so that after the decentration of the constricted pupil, it is still within the original pupil.

However, this may be impractical. It is known the eye can move in three degrees of freedom, so the pupil moves with respect to the ocular aberrations. During the move, the pupil may not constrict. But if the pupil size does not change, the part of the wavefront that moves into the pupil is unknown. To solve this problem, it is possible extrapolate the original wavefront to a bigger pupil size to allow for the decentration of the pupil.

As discussed in Section 2 above, the coefficients of a set of basis functions can be calculated from an original set when the pupil constricts. The same formula can be used to calculate the coefficients of basis functions when the pupil dilates. When the number of terms in the wavefront expansion is the same when the pupil dilates, there is a set of coefficients associated with the dilated pupil size that when the pupil constricts to the original size, the new set of coefficients becomes the original set.

Figures 17A, 17B, 17C:
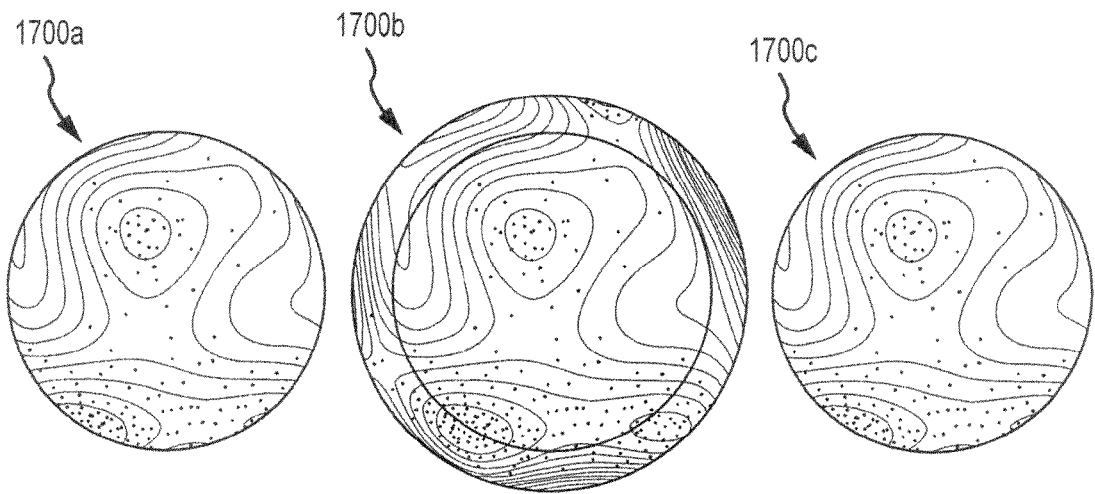
FIGS. 17A to 17C show illustrations of wavefront maps for a human eye, according to embodiments of the present invention.

FIGS. 17A to 17C show an example of an original ocular wavefront 1700a, extrapolated to an ocular wavefront 1700b corresponding to a larger pupil size, and then an ocular wavefront 1700c corresponding to a pupil constricted to the original pupil size. The original wavefront 1700a and the final wavefront 1700c are identical.

According to some embodiments of the present invention, care should be taken for the wavefront extrapolation in the following considerations. First of all, when the pupil size dilates, there might be higher spatial frequency information that should be captured, and hence it is possible to use more coefficients of the basis functions in the wavefront expansion. Once the number of basis functions increase, the above assumption may no longer be true, and the extrapolation can generate error. Secondly, in practice, the coefficients of basis functions during the wavefront reconstruction can be related to error in the aberrometers, such as the spot detection algorithm, centroid calculation algorithm, and the reconstruction algorithm. When the pupil dilates, such error in some cases may not scale linearly. Therefore, the extrapolation of the ocular wavefront may induce additional error related to the difference in the reconstruction error with different pupil sizes. Nevertheless, the ocular wavefront extrapolation can provide a very useful tool in the analysis of wavefront decentration, as discussed in the following subsections.

4.2 Wavefront Decentration with Taylor Monomials

Because of the simple form, the set of Taylor monomials can be a useful set in wavefront decentration analysis. Suppose the wavefront radius is R and the wavefront moves by $\Delta x$ and $\Delta y$ in the x- and y-directions, respectively. Because we normally use normalized coordinates, let $\Delta u = \Delta x/R$ and $\Delta v = \Delta y/R$. It can be shown (Appendix D) that Taylor coefficients of the decentered wavefront is related to Taylor coefficients of the original wavefront by $$b_i = \sum_{i'=0}^{J} C_{ii'}^{4t} a_{i'}, \quad (32)$$

where the conversion matrix $$C_{ii'}^{4t} = \sum_{i'=0}^{J} \frac{(-1)^{p'-p}(q')!(p'-q')!}{(q'-q)!(p'-p-q'+q)!q!(p-q)!} (\Delta u)^{q'-q} (\Delta v)^{p'-p-q'+q}, \quad (33)$$

where $p' \geq p$, $q' \geq q$ and $p'-p \geq q'-q$, p and q are associated with the index i and p' and q' are associated with the index i'. The relationship between the double index p, q and the single index i for Taylor monomials is given by Eqs. (33.1) and (33.2), respectively. Eq. (33.1) shows a conversion of a single-index to a double index.

$$\{p = int[(\sqrt{8i+1}-1)/2], q = 2i - p^2 - p\} \quad (33.1)$$

Eq. (33.2) shows a conversion of a double-index to a single-index.

$$i = \frac{p(p+1)}{2} + q \quad (33.2)$$

Figures 18A, 18B, 18C:
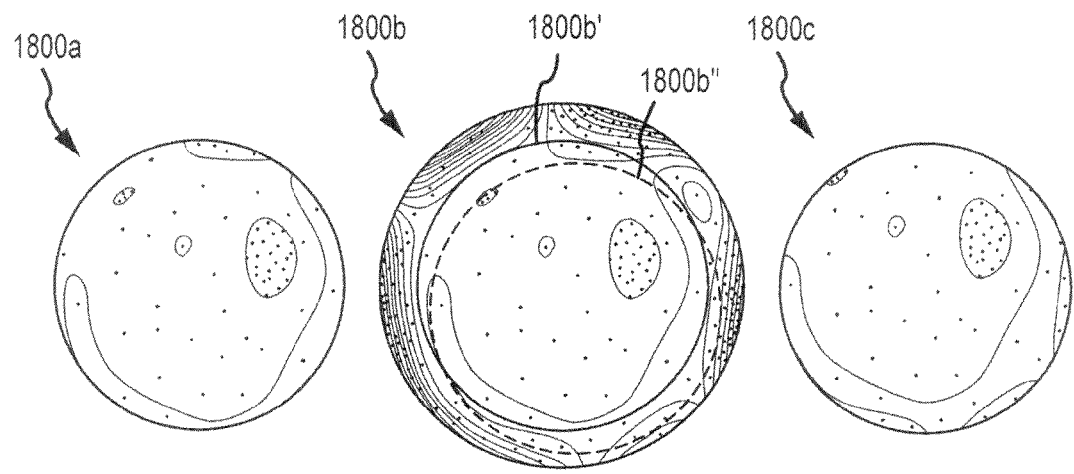
FIGS. 18A to 18C show illustrations of wavefront maps for a human eye, according to embodiments of the present invention.

Analytical formulas for $p \leq 6$ for the decentration of ocular wavefronts represented by Taylor monomials are listed in Table 12. In practice, as discussed in the previous subsection, these formulas can be used directly with the understanding that when a decentration occurs, the part of the wavefront that moves into the pupil can be extrapolated. FIGS. 18A to 18C show an example of the original wavefront 1800a, extrapolated to a larger pupil size 1800b that shows both the original wavefront 1800b' (solid circle) and the decentered wavefront 1800b" (dotted circle), and the decentered wavefront 1800c calculated directly from the formulas listed in Table 12. In this example of wavefront decentration, FIG. 18A shows the original wavefront 1800a with a 6 mm pupil, FIG. 18B shows the extrapolated wavefront 1800b to 7.5 mm pupil, and FIG. 18C shows the decentered wavefront 1800c ($\Delta u = -0.1$ and $\Delta v = 0.15$). Note the lower right corner of the decentered wavefront comes from the extrapolated wavefront. Apparently, the calculated decentered wavefront does represent the decentered wavefront of the extrapolated wavefront. The corresponding Taylor coefficients are shown in Table 13. In some embodiments, this approach can be used to determine an extrapolated wavefront for a patient who desires a vision treatment for specific viewing conditions. For example, if the wavefront is captured when the patient has a first geometrical configuration with a pupil size of 6 mm, and the patient desires a vision treatment for viewing conditions in dim light that correspond to a second geometrical configuration with a pupil size of 7 mm, it is possible to extrapolate the examined wavefront as described above, and to develop a vision treatment based on the extrapolation. Hence, a first set of basis function coefficients can be determined for the evaluation context or environment, and a second set of basis function coefficients can be determined for the viewing context or environment, where the second set of coefficients is based on the first geometrical configuration, the second geometrical configuration, and the first set of coefficients. Similarly, a first wavefront map can be determined for the evaluation context or environment, and a second wavefront map can be determined for the viewing context or environment, where the second wavefront map is based on the first geometrical configuration, the second geometrical configuration, and the first wavefront map. A prescription for treating the patient can be based on the second set of coefficients or the second wavefront map, for example.

4.3 Wavefront Decentration with Zernike Polynomials

Aspects of decentration of wavefronts represented by Zernike polynomials has been discussed in, for example, Bará, S. et al., *Appl. Opt.*, 39:3413-3420 (2000), Guirao, A. et al., *J. Opt. Soc. Am. A*, 18:1003-1015 (2001), Bará, S. et al., *J. Opt. Soc. Am. A*, 23:2061-2066 (2006), and Lundström L. et al., *J. Opt. Soc. Am. A*, 24:569-577 (2007). An analytical approach using Taylor expansion was suggested in Guirao, A. et al., *J. Opt. Soc. Am. A*, 18:1003-1015 (2001) for the calculation of the Zernike coefficients of a decentered wavefront from the original set of Zernike coefficients. A first order approximation was taken for practical applications. Lundström L. et al., *J. Opt. Soc. Am. A*, 24:569-577 (2007) reported another analytical approach with a matrix method that is based on a previous approach suggested in Campbell, C. E., *J. Opt. Soc. Am. A*, 20:209-217 (2003).

Table 12 shows decentered Taylor coefficients $b_i$ as a function of the original Taylor coefficients $a_i$ for $n \leq 6$.

TABLE 12

| p | Q | Formula |
|---|---|---|
| 0 | 0 | $b_0 = a_0 - a_1\Delta v - a_2\Delta u + a_3(\Delta v)^2 + a_4\Delta u\Delta v + a_5(\Delta u)^2 - a_6(\Delta v)^3 - a_7\Delta u(\Delta v)^2 - a_8(\Delta u)^2\Delta v - a_9(\Delta u)^3 + a_{10}(\Delta v)^4 + a_{11}\Delta u(\Delta v)^3 + a_{12}(\Delta u)^2(\Delta v)^2 + a_{13}(\Delta u)^3\Delta v + a_{14}(\Delta u)^4 - a_{15}(\Delta v)^5 - a_{16}\Delta u(\Delta v)^4 - a_{17}(\Delta u)^2(\Delta v)^3 - a_{18}(\Delta u)^3(\Delta v)^2 - a_{19}(\Delta u)^4\Delta v -$ |

TABLE 12-continued

| p | Q | Formula |
|---|---|---------|
|   |   | $a_{20}(\Delta v)^5 + a_{21}(\Delta v)^6 + a_{22}\Delta u(\Delta v)^5 + a_{23}(\Delta u)^2(\Delta v)^4 + a_{24}(\Delta u)^3(\Delta v)^3 + a_{25}(\Delta u)^4(\Delta v)^2 + a_{26}(\Delta u)^5\Delta v + a_{27}(\Delta u)^6$ |
| 1 | 0 | $b_1 = a_1 - 2a_3\Delta v - a_4\Delta u + 3a_6(\Delta v)^2 + 2a_7\Delta u\Delta v + a_8(\Delta u)^2 - 4a_{10}(\Delta v)^3 - 3a_{11}\Delta u(\Delta v)^2 - 2a_{12}(\Delta u)^2\Delta v - a_{13}(\Delta u)^3 + 5a_{15}(\Delta v)^4 + 4a_{16}\Delta u(\Delta v)^3 + 3a_{17}(\Delta u)^2(\Delta v)^2 + 2a_{18}(\Delta u)^3\Delta v + a_{19}(\Delta u)^4 - 6a_{21}(\Delta v)^5 - 5a_{22}\Delta u(\Delta v)^4 - 4a_{23}(\Delta u)^2(\Delta v)^3 - 3a_{24}(\Delta u)^3(\Delta v)^2 - 2a_{25}(\Delta u)^4\Delta v - a_{26}(\Delta u)^5$ |
| 1 | 1 | $b_2 = a_2 - a_4\Delta v - 2a_5\Delta u + a_7(\Delta v)^2 + 2a_8\Delta u\Delta v + 3a_9(\Delta u)^2 - a_{11}(\Delta v)^3 - 2a_{12}\Delta u(\Delta v)^2 - 3a_{13}(\Delta u)^2\Delta v - 4a_{14}(\Delta u)^3 + a_{16}(\Delta v)^4 + 2a_{17}\Delta u(\Delta v)^3 + 3a_{18}(\Delta u)^2(\Delta v)^2 + 4a_{19}(\Delta u)^3\Delta v + 5a_{20}(\Delta u)^4 - a_{22}(\Delta v)^5 - 2a_{23}\Delta u(\Delta v)^4 - 3a_{24}(\Delta u)^2(\Delta v)^3 - 4a_{25}(\Delta u)^3(\Delta v)^2 - 5a_{26}(\Delta u)^4\Delta v - 6a_{27}(\Delta u)^5$ |
| 2 | 0 | $b_3 = a_3 - 3a_6\Delta v - a_7\Delta u + 6a_{10}(\Delta v)^2 + 3a_{11}\Delta u\Delta v + a_{12}(\Delta u)^2 - 10a_{15}(\Delta v)^3 - 6a_{16}\Delta u(\Delta v)^2 - 3a_{17}(\Delta u)^2\Delta v - a_{18}(\Delta u)^3 + 15a_{21}(\Delta v)^4 + 10a_{22}\Delta u(\Delta v)^3 + 6a_{23}(\Delta u)^2(\Delta v)^2 + 3a_{24}(\Delta u)^3\Delta v + a_{25}(\Delta u)^4$ |
| 2 | 1 | $b_4 = a_4 - 2a_7\Delta v - 2a_8\Delta u + 3a_{11}(\Delta v)^2 + 4a_{12}\Delta u\Delta v + 3a_{13}(\Delta u)^2 - 4a_{16}(\Delta v)^3 - 6a_{17}\Delta u(\Delta v)^2 - 6a_{18}(\Delta u)^2\Delta v - 4a_{19}(\Delta u)^3 + 5a_{22}(\Delta v)^4 + 8a_{23}\Delta u(\Delta v)^3 + 9a_{24}(\Delta u)^2(\Delta v)2 + 8a_{25}(\Delta u)^3\Delta v + 5a_{26}(\Delta u)^4$ |
| 2 | 2 | $b_5 = a_5 - a_8\Delta v - 3a_9\Delta u + a_{12}(\Delta v)^2 + 3a_{13}\Delta u\Delta v + 6a_{14}(\Delta u)^2 - a_{17}(\Delta v)^3 - 3a_{18}\Delta u(\Delta v)^2 - 6a_{19}(\Delta u)^2\Delta v - 10a_{20}(\Delta u)^3 + a_{23}(\Delta v)^4 + 3a_{24}\Delta u(\Delta v)^3 + 6a_{25}(\Delta u)^2(\Delta v)^2 + 10a_{26}(\Delta u)^3\Delta v + 15a_{27}(\Delta u)^4$ |
| 3 | 0 | $b_6 = a_6 - 4a_{10}\Delta v - a_{11}\Delta u + 10a_{15}(\Delta v)^2 + 4a_{16}\Delta u\Delta v + a_{17}(\Delta u)^2 - 20a_{21}(\Delta v)^3 - 10a_{22}\Delta u(\Delta v)^2 - 4a_{23}(\Delta u)^2\Delta v - a_{24}(\Delta u)^3$ |
| 3 | 1 | $b_7 = a_7 - 3a_{11}\Delta v - 2a_{12}\Delta u + 6a_{16}(\Delta v)^2 + 6a_{17}\Delta u\Delta v + 3a_{18}(\Delta u)^2 - 10a_{22}(\Delta v)^3 - 12a_{23}\Delta u(\Delta v)^2 - 9a_{24}(\Delta u)^2\Delta v - 4a_{25}(\Delta u)^3$ |
| 3 | 2 | $b_8 = a_8 - 2a_{12}\Delta v - 3a_{13}\Delta u + 3a_{17}(\Delta v)^2 + 6a_{18}\Delta u\Delta v + 6a_{19}(\Delta u)^2 - 4a_{23}(\Delta v)^3 - 9a_{24}\Delta u(\Delta v)^2 - 12a_{25}(\Delta u)^2\Delta v - 10a_{26}(\Delta u)^3$ |
| 3 | 3 | $b_9 = a_9 - a_{13}\Delta v - 4a_{14}\Delta u + a_{18}(\Delta v)^2 + 4a_{19}\Delta u\Delta v + 10a_{20}(\Delta u)^2 - a_{24}(\Delta v)^3 - 4a_{25}\Delta u(\Delta v)^2 - 10a_{26}(\Delta u)^2\Delta v - 20a_{27}(\Delta v)^3$ |
| 4 | 0 | $b_{10} = a_{10} - 5a_{15}\Delta v - a_{16}\Delta u + 15a_{21}(\Delta v)^2 + 5a_{22}\Delta u\Delta v + a_{23}(\Delta u)^2$ |
| 4 | 1 | $b_{11} = a_{11} - 4a_{16}\Delta v - 2a_{17}\Delta u + 10a_{22}(\Delta v)^2 + 8a_{23}\Delta u\Delta v + 3a_{24}(\Delta u)^2$ |
| 4 | 2 | $b_{12} = a_{12} - 3a_{17}\Delta v - 3a_{18}\Delta u + 6a_{23}(\Delta v)^2 + 9a_{24}\Delta u\Delta v + 6a_{25}(\Delta u)^2$ |
| 4 | 3 | $b_{13} = a_{13} - 2a_{18}\Delta v - 4a_{19}\Delta u + 3a_{24}(\Delta v)^2 + 8a_{25}\Delta u\Delta v + 10a_{26}(\Delta u)^2$ |
| 4 | 4 | $b_{14} = a_{14} - a_{19}\Delta v - 5a_{20}\Delta u + a_{25}(\Delta v)^2 + 5a_{26}\Delta u\Delta v + 15a_{27}(\Delta u)^2$ |
| 5 | 0 | $b_{15} = a_{15} - 6a_{21}\Delta v - a_{22}\Delta u$ |
| 5 | 1 | $b_{16} = a_{16} - 5a_{22}\Delta v - 2a_{23}\Delta u$ |
| 5 | 2 | $b_{17} = a_{17} - 4a_{23}\Delta v - 3a_{24}\Delta u$ |
| 5 | 3 | $b_{18} = a_{18} - 3a_{24}\Delta v - 4a_{25}\Delta u$ |
| 5 | 4 | $b_{19} = a_{19} - 2a_{25}\Delta v - 5a_{26}\Delta u$ |
| 5 | 5 | $b_{20} = a_{20} - a_{26}\Delta v - 6a_{27}\Delta u$ |
| 6 | 0 | $b_{21} = a_{21}$ |
| 6 | 1 | $b_{22} = a_{22}$ |
| 6 | 2 | $b_{23} = a_{23}$ |
| 6 | 3 | $b_{24} = a_{24}$ |
| 6 | 4 | $b_{25} = a_{25}$ |
| 6 | 5 | $b_{26} = a_{26}$ |
| 6 | 6 | $b_{27} = a_{27}$ |

This section discusses a relationship between the new set of Zernike coefficients from the original set when the wavefront is decentered. The strategy is to convert the original set of Zernike coefficients to Taylor coefficients, calculate a new set of Taylor coefficients from the formulas given in Table 12, and convert the new set of Taylor coefficients to the new set of Zernike coefficients. Hence, we have $$b_i = \sum_{i'=0}^{J} C_{ii'}^{z4z} a_{i'}, \quad (34)$$

where the conversion matrix $C_{ii}^{z4z}$ CAP can be calculated as $$C^{z4z} = C^{t2z} C^{t4t} C^{z2t}, \quad (35)$$

where the matrices $C^{t2z}$ is the matrix converting Taylor coefficients to Zernike coefficients and $C^{z2t}$ is the matrix converting Zernike coefficients to Taylor coefficients. Aspects of these matrices are discussed in Dai, G.-m., "*Wavefront expansion basis functions and their relationships*" Journal of the Optical Society of America A, 23, 1657-1668 (2006). Note that $C^{z2t} = (C^{t2z})^{-1}$ so Eq. (35) may be written as:

$$C^{z4z} = C^{t2z} C^{t4t} (C^{t2z})^{-1}. \quad (36)$$

Eq. (34) provides a generic formula that, for example, can be expanded for $b_3$, $b_4$, and $b_5$ so as to correspond to Table 15. Hence, Eq. (34) can provide a full formula that can be used to calculate all terms. Table 15 corresponds to three terms associated with refraction changes. The three terms potentially effect or influence the calculation of refractions.

Table 13 provides a list of Taylor coefficients corresponding to wavefronts shown in FIGS. 18A to 18C.

TABLE 13

| i | p | q | Original | Extrapolated | Decentered |
|---|---|---|----------|--------------|------------|
| 0 | 0 | 0 | 0.6485 | 0.6485 | 0.2619 |
| 1 | 1 | 0 | 2.2684 | 2.8355 | 1.4310 |
| 2 | 1 | 1 | −1.0775 | −1.6836 | −0.6566 |
| 3 | 2 | 0 | −2.1462 | −3.3534 | 0.3992 |
| 4 | 2 | 1 | −8.5492 | −13.3581 | −11.7601 |
| 5 | 2 | 2 | −7.1252 | −13.9164 | −4.3075 |
| 6 | 3 | 0 | −5.7467 | −11.2240 | −4.3855 |
| 7 | 3 | 1 | 8.2492 | 16.1117 | −4.2935 |
| 8 | 3 | 2 | −14.0384 | −27.4187 | −11.1315 |
| 9 | 3 | 3 | 0.7262 | 1.7729 | 4.9569 |
| 10 | 4 | 0 | 4.1616 | 10.1602 | 2.4427 |
| 11 | 4 | 1 | 30.0251 | 73.3035 | 32.8528 |
| 12 | 4 | 2 | 13.2908 | 32.4482 | 8.5095 |
| 13 | 4 | 3 | 17.8017 | 43.4612 | 21.9792 |
| 14 | 4 | 4 | 19.2824 | 58.8452 | 16.4569 |
| 15 | 5 | 0 | 2.1909 | 6.6861 | 2.1715 |
| 16 | 5 | 1 | −10.0422 | −30.6464 | 8.3827 |
| 17 | 5 | 2 | 15.7452 | 48.0505 | 7.5533 |
| 18 | 5 | 3 | −2.2420 | −6.8420 | 5.3144 |
| 19 | 5 | 4 | 11.8121 | 36.0477 | 11.3796 |
| 20 | 5 | 5 | 0.7991 | 3.0483 | −5.1434 |
| 21 | 6 | 0 | −2.7227 | −10.3863 | −2.7227 |
| 22 | 6 | 1 | −24.6981 | −94.2158 | −24.6981 |
| 23 | 6 | 2 | −0.4933 | −1.8818 | −0.4933 |
| 24 | 6 | 3 | −28.2930 | −107.9292 | −28.2930 |
| 25 | 6 | 4 | −12.9387 | −49.3572 | −12.9387 |
| 26 | 6 | 5 | −8.6282 | −32.9140 | −8.6282 |
| 27 | 6 | 6 | −12.0612 | −57.5123 | −12.0612 |

FIGS. 19A to 19H show an example of an ocular wavefront of 6 mm in diameter and the decentered wavefronts for decentration of 0.05 mm, 0.15 mm, and 0.5 mm, respectively. The corresponding residual wavefronts are also shown if a vision correction is applied to the original wavefront. Table 14 shows the corresponding Zernike coefficients. In this example of wavefront decentration, FIG. 19A shows the original wavefront 1900*a* with a pupil size of 6 mm, FIG. 19B shows the decentered wavefront 1900*b* after 0.05 mm decentration in the x direction, FIG. 19C shows the decentered wavefront 1900*c* after 0.15 mm decentration in the x direction, and FIG. 19D shows the decentered wavefront 1900*d* after 0.5 mm decentration in the x direction. The residual wavefronts 1900*e*, 1900*f*, 1900*g*, and 1900*h*, that correspond to wavefronts from FIGS. 19A to 19D are shown in FIGS. 19E to 19H, respectively. The wavefront maps use the same scale. To see the influence of the decentration on the visual performance, FIGS. 20A to 20G show the point spread functions and the corresponding simulated blurred 20/20 letter E images. The top row illustrates the point spread function and the bottom row illustrates the corresponding blurred 20/20 letter E for the wavefront maps shown in FIGS. 19A to 19H. Hence, FIGS. 20A to 20D refer to the residual wavefronts as shown in FIGS. 19E to 19H. Relatedly, FIGS. 20E to 20G refer to the residual wavefronts excluding the low orders for the wavefronts corresponding to FIGS. 19F to 19H. The field of view for all the images of 6'×6'. The Strehl ratios from FIGS. 19A to 19H are 1, 0.720, 0.138, 0.025, 0.754, 0.182, and 0.020, respectively.

Table 14 lists Zernike coefficients for the decentered wavefronts and for the residual wavefronts after a partial vision correction due to a decentration of the eye, as shown in FIGS. 19A to 19H. The original wavefront without decentration corresponds to a low myopic eye with a lot of high order aberrations with a 6 mm pupil. The residual RMS wavefront error as well as the residual high order RMS wavefront error for the partial correction are also shown. Note that the coefficients of the sixth order, i.e., $a_{21}$ through $a_{27}$ may not change after the decentration.

TABLE 14

| | | | Decentered (mm) wavefronts | | | | Residual wavefronts | | |
|---|---|---|---|---|---|---|---|---|---|
| i | n | m | 0 | 0.05 | 0.15 | 0.5 | 0.05 | 0.15 | 0.5 |
| 0 | 0 | 0 | 0.4501 | 0.4416 | 0.4230 | 0.3130 | −0.0085 | −0.0271 | −0.1371 |
| 1 | 1 | −1 | −0.2689 | −0.2651 | −0.2523 | −0.1310 | 0.0038 | 0.0166 | 0.1379 |
| 2 | 1 | 1 | 0.0712 | 0.0484 | 0.0100 | 0.0321 | −0.0228 | −0.0612 | −0.0391 |
| 3 | 2 | −2 | −0.0093 | −0.0149 | −0.0309 | −0.1712 | −0.0056 | −0.0216 | −0.1619 |
| 4 | 2 | 0 | 0.2609 | 0.2497 | 0.2207 | 0.0280 | −0.0112 | −0.0402 | −0.2329 |
| 5 | 2 | 2 | 0.1310 | 0.1140 | 0.0682 | −0.2434 | −0.0170 | −0.0628 | −0.3744 |
| 6 | 3 | −3 | −0.0218 | −0.0281 | −0.0321 | 0.0603 | −0.0063 | −0.0103 | 0.0821 |
| 7 | 3 | −1 | −0.2407 | −0.2361 | −0.2204 | −0.0843 | 0.0046 | 0.0203 | 0.1564 |
| 8 | 3 | 1 | 0.1607 | 0.1564 | 0.1512 | 0.2353 | −0.0043 | −0.0095 | 0.0746 |
| 9 | 3 | 3 | −0.0221 | −0.0056 | 0.0313 | 0.2518 | 0.0165 | 0.0534 | 0.2739 |
| 10 | 4 | −4 | 0.0462 | 0.0358 | 0.0149 | −0.0592 | −0.0104 | −0.0313 | −0.1054 |
| 11 | 4 | −2 | 0.1168 | 0.0899 | 0.0305 | −0.2366 | −0.0269 | −0.0863 | −0.3534 |
| 12 | 4 | 0 | 0.1687 | 0.1710 | 0.1658 | 0.0464 | 0.0023 | −0.0029 | −0.1223 |
| 13 | 4 | 2 | 0.0953 | 0.0841 | 0.0497 | −0.1953 | −0.0112 | −0.0456 | −0.2906 |
| 14 | 4 | 4 | −0.1079 | −0.1095 | −0.1195 | −0.2264 | −0.0016 | −0.0116 | −0.1185 |
| 15 | 5 | −5 | −0.0314 | −0.0365 | −0.0468 | −0.0827 | −0.0051 | −0.0154 | −0.0513 |
| 16 | 5 | −3 | 0.1452 | 0.1507 | 0.1616 | 0.1997 | 0.0055 | 0.0164 | 0.0545 |
| 17 | 5 | −1 | 0.1390 | 0.1541 | 0.1844 | 0.2902 | 0.0151 | 0.0454 | 0.1512 |
| 18 | 5 | 1 | −0.0299 | −0.0050 | 0.0449 | 0.2194 | 0.0249 | 0.0748 | 0.2493 |
| 19 | 5 | 3 | 0.1312 | 0.1497 | 0.1866 | 0.3159 | 0.0185 | 0.0554 | 0.1847 |
| 20 | 5 | 5 | −0.1263 | −0.1198 | −0.1068 | −0.0613 | 0.0065 | 0.0195 | 0.0650 |
| 21 | 6 | −6 | −0.0420 | −0.0420 | −0.0420 | −0.0420 | 0.0000 | 0.0000 | 0.0000 |
| 22 | 6 | −4 | 0.0895 | 0.0895 | 0.0895 | 0.0895 | 0.0000 | 0.0000 | 0.0000 |
| 23 | 6 | −2 | −0.1400 | −0.1400 | −0.1400 | −0.1400 | 0.0000 | 0.0000 | 0.0000 |
| 24 | 6 | 0 | −0.1032 | −0.1032 | −0.1032 | −0.1032 | 0.0000 | 0.0000 | 0.0000 |
| 25 | 6 | 2 | −0.0849 | −0.0849 | −0.0849 | −0.0849 | 0.0000 | 0.0000 | 0.0000 |
| 26 | 6 | 4 | −0.0861 | −0.0861 | −0.0861 | −0.0861 | 0.0000 | 0.0000 | 0.0000 |
| 27 | 6 | 6 | 0.0259 | 0.0259 | 0.0259 | 0.0259 | 0.0000 | 0.0000 | 0.0000 |
| Residual RMS wavefront error | | | | | | | 0.0605 | 0.1911 | 0.8661 |
| Residual high order RMS wavefront error | | | | | | | 0.0510 | 0.1604 | 0.7001 |

The elements of the matrix $C^{z4z}$ and the individual formulas from Eq. (34) can be complicated. A Matlab code is given in Appendix E that accounts for the conversion of Zernike coefficients for the pupil size change and the wavefront rotation and decentration. For a few special terms, namely the sphere and cylinder, coma and trefoil, and spherical aberration, they are discussed in detail.

The sphere and cylinder will be discussed separately in the next subsection. In the following, certain high order aberration are discussed, namely the spherical aberration. Using Eq. (34), it can be shown that $$b_{12} = a_{12} - 2\sqrt{15}(a_{17}\Delta v + a_{18}\Delta u) + 3\sqrt{35}(2a_{24} + \sqrt{2}a_{25})(\Delta u)^2 + 6\sqrt{70}a_{23}\Delta u\Delta v + 3\sqrt{35}(2a_{24} - \sqrt{2}a_{25})(\Delta v)^2. \quad (37)$$

Equation (37) indicates that the secondary coma ($Z_{17}$ and $Z_{18}$), the tertiary astigmatism ($Z_{23}$ and $Z_{25}$), and the secondary spherical aberration ($Z_{24}$) induce the primary spherical aberration ($Z_{12}$) when an ocular wavefront is decentered.

Another high order aberration is the coma. From Eq. (34), it can be shown that $$b_7 = a_7 - 2(\sqrt{5}\,a_{11} + \sqrt{7}\,a_{23})\Delta u - \\ 2(\sqrt{10}\,a_{12} - \sqrt{5}\,a_{13} + \sqrt{14}\,a_{24} - \sqrt{7}\,a_{25})\Delta v + \\ 5\sqrt{6}\,(a_{16} + a_{17})(\Delta u)^2 + 10\sqrt{6}\,a_{18}\,-a_{19})\Delta u\Delta v - \\ 5\sqrt{6}\,(a_{16} - 3a_{17})(\Delta v)^2 - 10\sqrt{7}\,(a_{22} + 2a_{23})(\Delta u)^3 - \\ 30\sqrt{7}\,(\sqrt{2}\,a_{24} - a_{26})(\Delta u)^2\Delta v + \\ 30\sqrt{7}\,(a_{22} - 2a_{23})\Delta u(\Delta v)^2 - \\ 10\sqrt{7}\,(3\sqrt{2}\,a_{24} - 4a_{25} + a_{26}(\Delta v)^3 \quad (38a)$$

-continued $$b_8 = a_8 - 2(\sqrt{10}\,a_{12} + \sqrt{5}\,a_{13} + \sqrt{14}\,a_{24} + \sqrt{7}\,a_{25})\Delta u - \\ 2(\sqrt{5}\,a_{11} + \sqrt{7}\,a_{23})\Delta v + 5\sqrt{6}\,(3a_{18} + a_{19})(\Delta u)^2 + \\ 10\sqrt{6}\,(a_{16} + a_{17})\Delta u\Delta v + 5\sqrt{6}\,(a_{18} - a_{19})(\Delta v)^2 - \\ 10\sqrt{7}\,(3\sqrt{2}\,a_{24} + 4a_{25} + a_{26})(\Delta u)^3 - \\ 30\sqrt{7}\,(a_{22} + 2a_{23})(\Delta u)^2\Delta v - \\ 30\sqrt{7}\,(\sqrt{2}\,a_{24} - a_{26})\Delta u(\Delta v)^2 + 10\sqrt{7}\,(a_{22} - a_{23})(\Delta v)^3 \quad (38a)$$

Equation (38) indicates that the primary ($Z_{12}$) and secondary ($Z_{24}$) spherical aberrations, the secondary ($Z_{11}$ and $Z_{13}$) and tertiary ($Z_{23}$ and $Z_{25}$) astigmatism, the secondary coma ($Z_{17}$ and $Z_{18}$), as well as $Z_{16}$, $Z_{19}$, $Z_{22}$, and $Z_{26}$ induce the coma when an ocular wavefront is decentered.

A primary spherical aberration ($Z_{12}$) Zernike polynomial typically does not induce trefoil. Other polynomials, such as those from $Z_{10}$ to $Z_{27}$, can contribute to the induction of trefoil, when an ocular wavefront is decentered.

4.4 Wavefront Refraction of Decentered Aberrations

Because Zernike coefficients can change when the wavefront is decentered, one thing to be noted is the change of the wavefront refraction. Indeed, there may be some discrepancy between the wavefront refraction and the manifest refraction, especially when the high order aberrations are relatively significant. Because the ocular wavefront is measured in scotopic lighting condition and the manifest refraction is measured in mesopic to photopic lighting condition, not only may the pupil size change, but the pupil center may also shift.

With the use of Eq. (34), the second order Zernike coefficients can be calculated. Table 15 lists the second order Zernike coefficients as contributed from the high order aberrations up to the sixth order. As can be seen each Zernike high order coefficient contributes to the second order Zernike coefficients when a decentration in both x- and y-direction occurs. In general, higher order coefficients have less significant effect to the second order coefficients as they correspond to higher power of the decentration. Once the second order coefficients are known, the wavefront refraction can be calculated by $$S = -\frac{4\sqrt{3}\,b_2^0}{R^2} - \frac{2\sqrt{6}\,\sqrt{(b_2^{-2})^2 + (b_2^2)^2}}{R^2}, \quad (39a)$$

$$C = \frac{4\sqrt{6}\,\sqrt{(b_2^{-2})^2 + (b_2^2)^2}}{R^2}, \quad (39b)$$

$$\theta = \frac{1}{2}\tan^{-1}\left(\frac{b_2^{-2}}{b_2^2}\right). \quad (39c)$$

Equations (39a), (39b), and (39c) can be used as a basis for determining a refraction when decentration occurs. b values, such as $b_{20}$, can be substituted from Table 15. To obtain an effect from decentration, the formulas from Table 15 can be used, which may depend on the original Zernike coefficient. The refraction could be influenced by almost all terms. Optionally, if a matrix formula such as Eq. (34) is used, b values can be obtained. For each case, such as a pupil constriction, a rotation, a decentration, or any combination thereof, it is possible to determine a general formula for the calculation of the new Zernike coefficients. From the low order Zernike coefficients, i.e., c3, c4, and c5, the new wavefront refraction can be determined. Another set can be used to determine refractions, which are useful when dealing with aberrations.

According to some embodiments of the present invention, for example, it is possible to calculate the wavefront refraction for a 0.5 μm of horizontal coma ($Z_8$) and 0.5 μm of spherical aberration ($Z_{12}$) over a 6 mm pupil when the pupil moves in the x-direction by 0.1 mm and 0.5 mm, respectively. From Table 15, we have $b_3=0$, $b_4=-2\sqrt{6}a_8\Delta u$, and $b_5=-2\sqrt{3}a_8\Delta u$ for the case of coma. Substituting $\Delta u=0.1/3=0.033$ and $\Delta u=0.5/3=0.165$, respectively, into these formulas, we have $b_3=0$, $b_4=-2\sqrt{6}\times0.5\times0.033=-0.081$ μm, and $b_5=-2\sqrt{3}\times0.5\times0.033=-0.057$ μm. Using Eq. (39), we find the refraction as 0.031 DS/0.062 DC×0°. For a 0.5 mm decentration, we obtain $b_3=0$, $b_4=-0.404$ μm, and $b_5=-0.286$ μm, corresponding to a refraction of 0.155 DS/0.311 DC×0°, which is exactly 5 times the previous refraction when the decentration is 0.1 mm.

For the spherical aberration, we have $b_3=0$, $b_4=4\sqrt{15}a_{12}(\Delta u)^2$, and $b_5=2\sqrt{30}a_{12}(\Delta u)^2$. Substituting $\Delta u=0.033$ into these formulas, we get $b_3=0$, $b_4=0.008$ μm, $b_5=0.006$ μm. Using Eq. (39), we obtain the refraction as −0.009 DS/0.006 DC×0°. For $\Delta u=0.165$, we have $b_3=0$, $b_4=0.211$ μm, and $b_5=0.149$ μm, corresponding to a refraction of −0.244DS/0.162 DC×0°. Note that in the case of the spherical aberration, the refraction is no longer 5 times the previous refraction when the decentration is 0.1 mm.

Table 15 lists Zernike coefficients of the defocus and astigmatism as contributed from higher order Zernike coefficients when a wavefront decentration occurs. Note that the sphere and cylinder may not change when a decentration occurs when no high order aberrations exist. For higher order coefficients, the contribution can be a function of the decentration in higher power: the powers of the decentration for the 3rd, 4th, 5th, and 6th order coefficients are 1, 2, 3 and 4, respectively.

TABLE 15

$b_3 = a_3$
$b_4 = a_4$
$b_5 = a_5$
$b_3 = -2\sqrt{3}(a_6 + a_7)\Delta u - 2\sqrt{3}(a_8 - a_9)\Delta v$
$b_4 = -2\sqrt{6}(a_8\Delta u + a_7\Delta v)$
$b_5 = -2\sqrt{3}(a_8 + a_9)\Delta u - 2\sqrt{3}(a_6 - a_7)\Delta v$
$b_3 = 2\sqrt{15}(a_{10} + 2a_{11})(\Delta u)^2 + 4\sqrt{15}(\sqrt{2}a_{12} - a_{14})\Delta u\Delta v - 2\sqrt{15}(a_{10} - 2a_{11})(\Delta v)^2$
$b_4 = 2\sqrt{15}(2a_{12} + \sqrt{2}a_{13})(\Delta u)^2 + 4\sqrt{30}a_{11}\Delta u\Delta v + 2\sqrt{15}(2a_{12} - \sqrt{2}a_{13})(\Delta v)^2$
$b_5 = 2\sqrt{15}(a_{14} + \sqrt{2}a_{12} + 2a_{13})(\Delta u)^2 + 4\sqrt{15}a_{10}\Delta u\Delta v - 2\sqrt{15}(a_{14} + \sqrt{2}a_{12} - 2a_{13})(\Delta v)^2$
$b_3 = 3\sqrt{2}(a_{16} + a_{17})\Delta u - 3\sqrt{2}(a_{18} - a_{19})\Delta v - 10\sqrt{2}(a_{15} + 3a_{16} + 2a_{17})(\Delta u)^3 - 30\sqrt{2}(2a_{18} - a_{19} - a_{20})(\Delta u)^2\Delta v + 30\sqrt{2}(a_{15} - a_{16} + 2a_{17})\Delta u(\Delta v)^2 - 10\sqrt{2}(2a_{18} - 3a_{19} + a_{20})(\Delta v)^3$
$b_4 = -6a_{18}\Delta u - 6a_{17}\Delta v - 20(3a_{18} + a_{19})(\Delta u)^3 - 60(a_{16} + a_{17})(\Delta u)^2\Delta v - 60(a_{18} - a_{19})\Delta u(\Delta v)^2 + 20(a_{16} - 3a_{17})(\Delta v)^3$
$b_5 = -3\sqrt{2}(a_{18} + a_{19})\Delta u - 3\sqrt{2}(a_{16} - a_{17})\Delta v - 10\sqrt{2}(4a_{18} - 3a_{19} + a_{20})(\Delta u)^3 - 30\sqrt{2}(a_{15} + a_{16})(\Delta u)^2\Delta v - 30\sqrt{2}(a_{19} - a_{20})\Delta u(\Delta v)^2 + 10\sqrt{2}(a_{15} - 3a_{16} + 4a_{17})(\Delta v)^3$
$b_4 = 5\sqrt{21}(2a_{24} + \sqrt{2}a_{25})(\Delta u)^2 + 10\sqrt{42}a_{23}\Delta u\Delta v + 5\sqrt{21}(2a_{24} - \sqrt{2}a_{25})(\Delta v)^2 + 5\sqrt{21}(6a_{24} + 4\sqrt{2}a_{25} + \sqrt{2}a_{26})(\Delta u)^4 + 20\sqrt{42}(a_{22} + 2a_{23})(\Delta u)^3\Delta v + 30\sqrt{21}(2a_{24} - \sqrt{2}a_{26})(\Delta u)^2(\Delta v)^2 - 20\sqrt{42}(a_{22} - 2a_{23})\Delta u(\Delta v)^3 + 5\sqrt{21}(6a_{24} - 4\sqrt{2}a_{25} + \sqrt{2}a_{26})(\Delta v)^4$
$b_5 = 5\sqrt{21}(\sqrt{2}a_{24} + 2a_{25} + a_{26})(\Delta u)^2 + 10\sqrt{21}a_{22}\Delta u\Delta v - 5\sqrt{21}(\sqrt{2}a_{24} - 2a_{25} + a_{26})(\Delta v)^2 + 5\sqrt{21}(4\sqrt{2}a_{25} + 7a_{25} + 4a_{26} + a_{27})(\Delta u)^4 + 20\sqrt{21}(a_{21} + 2a_{22} + a_{23})(\Delta u)^3\Delta v + 30\sqrt{21}(a_{25} - a_{27})(\Delta u)^2(\Delta v)^2 - 20\sqrt{21}(a_{21} - 2a_{22} + a_{23})\Delta u(\Delta v)^3 - 5\sqrt{21}(4\sqrt{2}a_{24} - 7a_{25} + 4a_{26} - a_{27})(\Delta v)^4$ Wavefront RMS error and refractions can also be considered. If a refraction is close to zero, then there is a good opportunity for achieving a favorable result. A generic formula can indicate what the wavefront RMS error will be after correction. According to some embodiments, Eq. (39) provides such a generic formula. If there is decentration that is not corrected for, then there is a greater chance of having wavefront RMS error.

5. Wavefront Representation for Resizing, Rotation, and Decentration

Wavefront representation with Zernike polynomials has been discussed in, for example, Bará, S. et al., *Appl. Opt.*, 39:3413-3420 (2000), Guirao, A. et al., *J. Opt. Soc. Am. A*, 18:1003-1015 (2001), Bará, S. et al., *J. Opt. Soc. Am. A*, 23:2061-2066 (2006), and Lundström L. et al., *J. Opt. Soc. Am. A*, 24:569-577 (2007). Lundström L. et al., *J. Opt. Soc. Am. A*, 24:569-577 (2007) proposed the use of matrix transformations that include pupil resizing, rotation, and decentration. However, this approach does not provide an analytical framework. Embodiments of the present invention, such as those exemplified in Tables 2, 10, 12, and 15, provide an analytical framework that reveals physical insights on how Zernike aberrations interact with each other when a geometrical transformation takes place.

5.1 Wavefront Transformation with Zernike Polynomials

As discussed elsewhere herein, the conversion of Zernike coefficients can be determined when a wavefront map goes through a geometrical transformation, such as decentration, rotation, or pupil resizing. When a combination of any of these happens, new Zernike coefficients can be obtained from the original set by the Zernike geometrical transformation matrix as $$b = C^{zgt} a, \quad (40)$$

where the Zernike geometrical transformations matrix $C^{zgt}$ can be written as the multiplication of a series of conversion matrices as $$C^{zgt} = C_3 C_2 C_1. \quad (41)$$

In Eq. (41), the matrices $C_1$, $C_2$, and $C_3$ represent the first, second, and the third geometrical transformations, respectively. They can be any of the decentration matrix $C^{z4z}$, the rotation matrix $C^{z3z}$, or the pupil resizing matrix $C^{z2z}$. The pupil resizing matrix $C^{z2z}$ is related to Zernike resizing polynomials $G_n^i(\epsilon)$.

As an example of wavefront decentration, rotation, and pupil constriction, FIG. 21A shows an original wavefront $2100a$ of 6 mm pupil and FIG. 21B shows the wavefront $2100b$ when it undergoes a decentration of −0.45 mm in the x- and 0.36 mm in the y-direction, respectively, a rotation of 25° counter clockwise, and a pupil constriction to 4.8 mm. Put differently, FIG. 21B shows the wavefront after a decentration of $\Delta u = -0.15$, $\Delta v = -0.15$, a rotation of 25° counter clockwise, and a pupil constriction ratio of $\epsilon = 0.8$. The corresponding Zernike coefficients after each transformation are shown in Table 16.

Appendix E shows a Matlab code that implements Eq. (40) for any series of geometrical transformations. For the previous example, we have $\Delta u = -0.45/3 = -0.15$, $\Delta v = 0.36/3 = 0.12$, $\phi = 25\pi/180$, and $\epsilon = 4.8/6 = 0.8$. Substituting these parameters into the function WavefrontTransform, the final Zernike coefficients can be obtained. The Zernike coefficients after each transformation can also be recorded, as shown in Table 16. Also shown in Table 16 are the total RMS wavefront error and high order RMS wavefront error. It is interesting to note that after a rotation, both the total RMS error and the high order RMS error do not change. In addition, the spherical equivalent (S+C/2) also does not change.

5.2 Wavefront Refraction after Transformation

As shown in Table 16, any of the geometrical transformations may change the low order Zernike coefficients, for example, $b_3$, $b_4$, and $b_5$ when high order aberrations exist. Therefore, the wavefront refraction also changes. As discussed in the previous subsection, a new set of Zernike coefficients can be calculated and Eq. (39) can be used to calculate the new wavefront refraction.

For the same example as in the previous subsection, Table 16 shows the wavefront refraction in minus cylinder notation for the original wavefront and after each of the geometrical transformations. In each of the geometrical transformations, the wavefront refraction changes.

Table 16 lists Zernike coefficients for the original wavefront, and those after it decenters −0.45 mm in the x- and 0.36 mm in the y-directions, respectively, and rotates by 25°, and finally its pupil constricts to 4.8 mm, as shown in FIGS. 21A and 21B. The total RMS, high order RMS, and the refractions in terms of sphere, cylinder, and cylinder axis are also shown. Minus cylinder notation is used.

TABLE 16

| i | n | m | Original | Decentered | Rotated | Constricted |
|---|---|---|---|---|---|---|
| 0 | 0 | 0 | 0.4501 | 1.2923 | 1.2923 | 1.0648 |
| 1 | 1 | −1 | −0.2689 | −0.6344 | 0.4544 | 0.4739 |
| 2 | 1 | 1 | 2.0712 | 2.4358 | 2.4757 | 1.8950 |
| 3 | 2 | −2 | −0.8093 | −0.8785 | −0.6004 | −0.5645 |
| 4 | 2 | 0 | 0.2609 | 0.3486 | 0.3486 | 0.2333 |
| 5 | 2 | 2 | 0.1310 | −0.0466 | 0.6430 | 0.6530 |
| 6 | 3 | −3 | −0.0218 | 0.0469 | −0.2146 | 0.0541 |
| 7 | 3 | −1 | −0.2407 | −0.1734 | −0.1336 | −0.0541 |
| 8 | 3 | 1 | 0.1607 | 0.0557 | 0.1238 | 0.2016 |
| 9 | 3 | 3 | −0.0221 | −0.2347 | −0.1060 | 0.0786 |
| 10 | 4 | −4 | 0.0462 | 0.1323 | −0.1920 | 0.0089 |
| 11 | 4 | −2 | 0.1168 | 0.3239 | 0.1873 | 0.2120 |
| 12 | 4 | 0 | 0.1687 | −0.0212 | −0.0212 | 0.0814 |
| 13 | 4 | 2 | 0.0953 | −0.0273 | −0.2657 | −0.1548 |
| 14 | 4 | 4 | −0.1079 | −0.1717 | −0.1005 | 0.0227 |
| 15 | 5 | −5 | −0.0314 | 0.1019 | −0.1261 | −0.0413 |
| 16 | 5 | −3 | 0.1452 | 0.0952 | −0.1816 | −0.0595 |
| 17 | 5 | −1 | 0.1390 | 0.0504 | −0.0158 | −0.0052 |
| 18 | 5 | 1 | −0.0299 | −0.1454 | −0.1531 | −0.0502 |
| 19 | 5 | 3 | 0.1312 | −0.2135 | −0.1472 | −0.0482 |
| 20 | 5 | 5 | −0.1263 | −0.0826 | −0.0361 | −0.0118 |
| 21 | 6 | −6 | −0.0420 | −0.0420 | 0.0493 | 0.0129 |
| 22 | 6 | −4 | 0.0895 | 0.0895 | −0.1003 | −0.0263 |
| 23 | 6 | −2 | −0.1400 | −0.1400 | −0.1550 | −0.0406 |
| 24 | 6 | 0 | −0.1032 | −0.1032 | −0.1032 | −0.0271 |
| 25 | 6 | 2 | −0.0849 | −0.0849 | 0.0527 | 0.0138 |
| 26 | 6 | 4 | −0.0861 | −0.0861 | −0.0732 | −0.0192 |
| 27 | 6 | 6 | 0.0259 | 0.0259 | −0.0014 | −0.0004 |
| RMS | | | 2.3633 | 3.0488 | 3.0488 | 2.4273 |
| HORMS | | | 0.5296 | 0.6280 | 0.6280 | 0.3780 |
| Sphere | | | 0.30 | 0.33 | 0.21 | 0.25 |
| Cylinder | | | −0.71 | −0.84 | −0.60 | −0.58 |
| Axis | | | 134° | 135° | 111° | 108° |

6. Example 1

One example, according to embodiments of the present invention, involves an eye that has −2.5 DS/+1.5 DC×81° and 0.35 microns of horizontal coma, −0.2 microns of vertical coma, and −0.28 microns of spherical aberration, on a 6 mm pupil. It possible to determine how the refraction changes when the wavefront decenters 0.2 mm in the x direction and 0.1 mm in the y direction, when it is rotated by 30 degree counter clockwise, and when it is constricted to 5 mm pupil. The wavefront maps $2200a$, $2200b$, $2200c$, and $2200d$ are shown in FIGS. 22A to 22D, respectively and the refractions are shown afterwards. The wavefront map of the original map is shown in FIG. 22A, and experiences a decentration of 0.2 mm in the x and 0.1 mm in the y direction as shown in FIG. 22B, a cyclorotation of 30 degree as shown in FIG. 22C, and a pupil constriction from 6 mm to 5 mm as shown in FIG. 22D.

The following are the refractions:

| | |
|---|---|
| Current | −2.50 DS/+1.50 DC × 81° |
| Decentered | −2.48 DS/+1.62 DC × 81.8° |
| Rotated | −2.48 DS/+1.62 DC × 111.8° |
| Constricted | −2.74 DS/+1.62 DC × 111.8° |

Without being bound by any particular theory, it is thought that a possible reason that the cylinder does not change is because there are only high order terms that affects the sphere. If the secondary astigmatism were present, for example, the cylinder would have changed.

7. Example 2

In another example, according to embodiments of the present invention, it can be shown that in these geometrical transformations, which terms contributed the most to the sphere power and which terms to the cylinder power.

7.1 Decentration

The influence of higher order aberrations on the refraction due to wavefront decentration may in some embodiments be a bit uncertain or complicated. However, in general, because the decentration is often much smaller than the pupil radius, the influence is dominated by terms that have the lowest powers of the decentration. For example, for defocus, the influence comes from the coma, primary spherical aberration, and secondary astigmatism, among other high order aberrations. Coma has the most impact on the refraction because it is linearly related to the decentration. But for spherical aberration and secondary astigmatism, the relation to the decentration is quadratic, although the coefficient for spherical aberration is about two times larger.

7.2 Rotation

When a wavefront map rotates, the sphere and cylinder typically do not change. Generally, only the cylinder axis changes by an additional angle of the rotation.

7.3 Pupil Constriction

Figure 23:
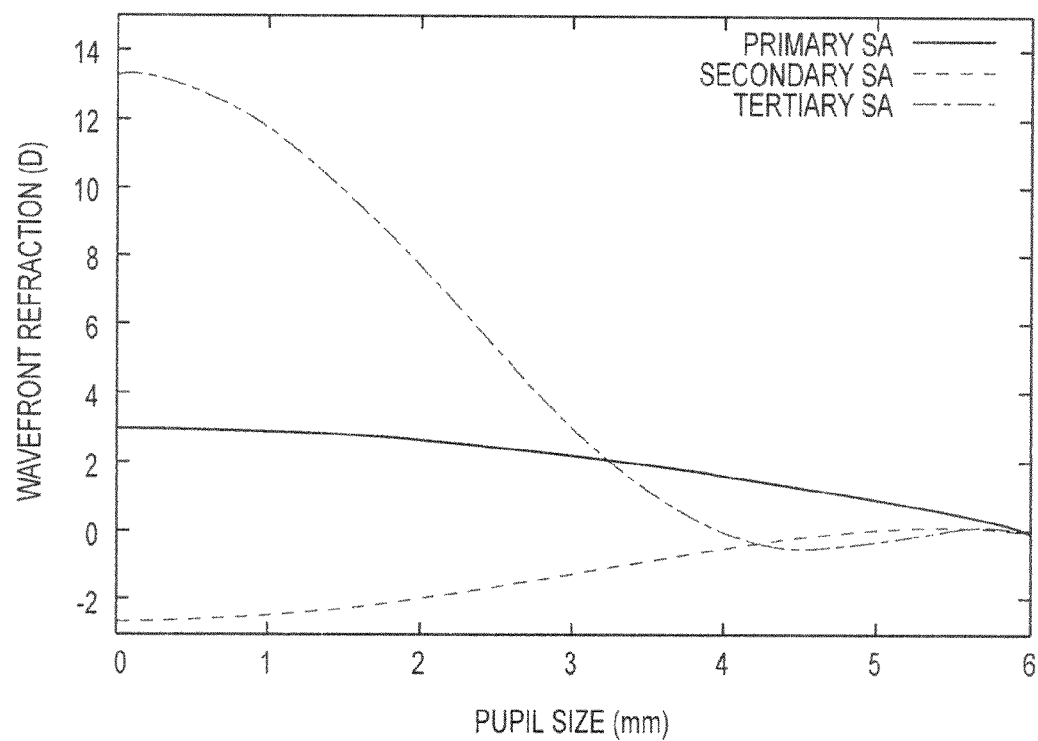
FIG. 23 shows a graph of curves for primary, secondary, and tertiary spherical aberration (SA) as a function of pupil size, according to embodiments of the present invention.

The defocus, or the spherical equivalent, can be affected by the primary, secondary, tertiary, and higher order spherical aberrations. The cylinder can be affected by the primary, secondary, tertiary, and higher order astigmatisms. For example, influence of the primary, secondary, and tertiary spherical aberration (SA) on spherical equivalent, or defocus, is shown in FIG. 23. Apparently, when the pupil constricts over half (pupil<3 mm), the influence from the primary, secondary, and tertiary SA becomes larger when it goes to higher orders. FIG. 23 shows that when pupil constricts, a positive spherical aberration will make the refraction more and more hyperopic monotonically. On the other hand, a negative spherical aberration may make it more myopic as the pupil constricts. For the secondary SA, however, for a positive spherical aberration, the refraction can become slightly more hyperopic initially as the pupil constricts, but can quickly become more myopic as the constriction continues. For a negative secondary SA, the situation can exactly reverse. For a positive tertiary SA, the refraction initially can become more myopic, then more hyperopic before it can become more hyperopic again finally. Again, for the negative tertiary SA, the situation can be reversed. This is why for presbyopic correction, in some embodiments it may be desirable to introduce negative primary SA, positive secondary SA, and negative tertiary SA so when the pupil constricts, it becomes more myopic.

In a situation when the wavefront maps changes due to decentration, pupil constriction, or rotation, during the surgery, it is possible to recalculate a new map and deliver the ablation based on that new map.

Induced High Order Aberrations Corresponding to Geometrical Transformations, and Techniques for Determining, Reporting, and Using in Treatment Embodiments of the present invention encompass systems, methods, and computer program products for evaluating induced high order aberrations corresponding to geometrical transformations such as cyclorotation, pupil center shift, pupil constriction, and pupil dilation.

Embodiments also encompass techniques for treating and reporting ocular aberrations over scaled or decentered pupils, or other geometrical transformations associated with pupils. In some instances, the techniques can be implemented in connection with software residing in or associated with systems such as WaveScan®, iDesign™, or CustomVue® devices.

Figure 24:
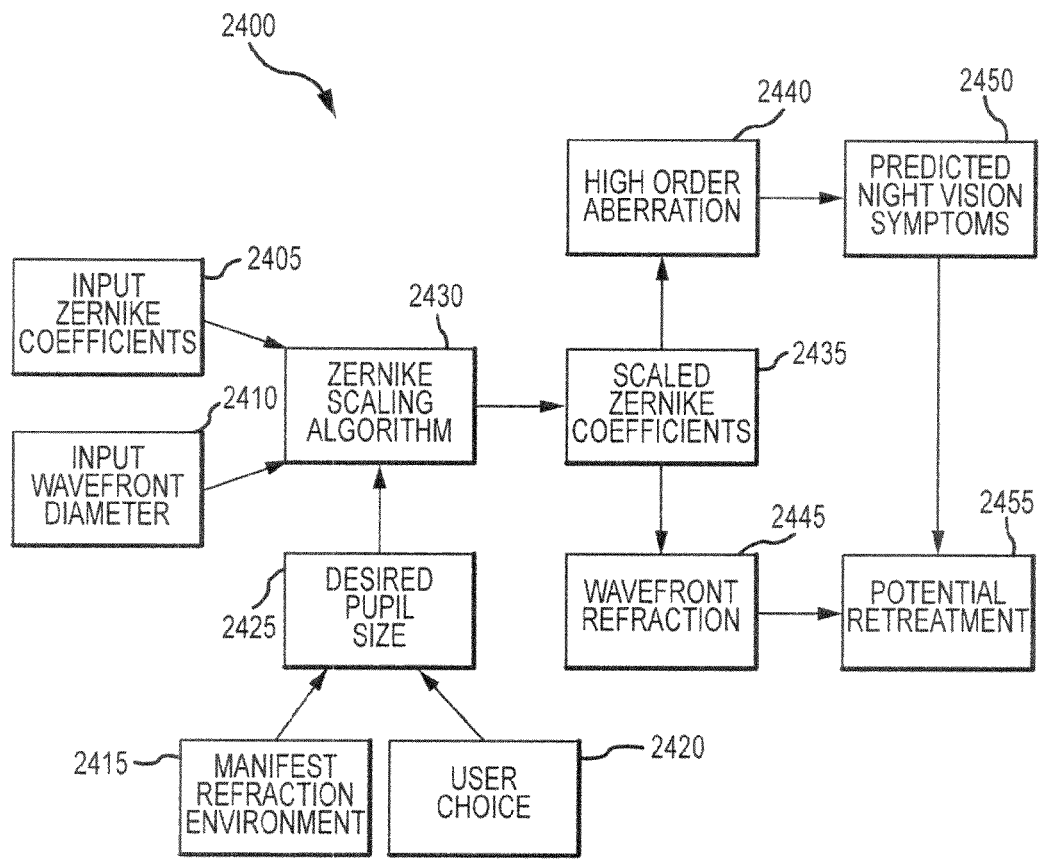
FIG. 24 illustrates aspects of the use of diagnostic display and the use of retreatment and enhancement treatment by pupil rescaling techniques according to embodiments of the present invention.

FIG. 24 provides a flow chart illustrating aspects of the use of diagnostic display and the use of retreatment and enhancement treatment by means of a pupil rescaling algorithm. As shown here, system 2400 can include an input module 2405 that receives Zernike coefficient information, an input module 2410 that receives wavefront diameter information, a manifest refraction environment module 2415 that receives manifest refraction environment information, and a user choice module 2420 that receives user choice information. Zernike coefficient information can include information from a wavefront examination, and encompass low order and high order aberrations. Manifest refraction environment information can encompass data related to lighting conditions. User choice information can encompass data related to physicians or operators, for example according to their needs or preferences.

A desired pupil size module 2425 can determine a desired pupil size based on manifest refraction environment information and user choice information received from manifest refraction environment module 2415 and user choice module 2420, respectively. A Zernike scaling algorithm module 2430 can operate to determine scaled Zernike coefficients based on Zernike coefficient information received from input module 2405, wavefront diameter information received from input module 2410, and desired pupil size information received from desired pupil size module 2425. In some cases, the desired pupil size can be 4 mm, 5 mm, 6 mm, or 7 mm. In some cases, the desired pupil size can be a scotopic pupil size, a mesopic pupil size, or a photopic pupil size. Optionally, a pupil size can be equivalent to the pupil size when the manifest refraction is taken.

As shown here, Zernike scaling algorithm module 2430 can output a set of scaled Zernike coefficients 2435. High order aberration module 2440 can operate to determine high order aberrations based on the scaled Zernike coefficient information 2435. Similarly, wavefront refraction module 2445 can operate to determine a wavefront refraction based on the scaled Zernike coefficient information 2435. A predicted night vision symptom module 2450 can determine predicted night vision symptoms based on high order aberration information received from high order aberration module 2440. A potential treatment or retreatment module 2455 can determine a potential treatment or retreatment based on wavefront refraction information received from wavefront refraction module 2445 and predicted night vision symptom information received from predicted night vision symptom module 2450. In some cases, a predicted night vision symptom can include a spherical aberration. Treatment module 2455 can be configured to reduce low order aberrations (e.g. as determined from a wavefront refraction), and to reduce night vision symptoms.

Figure 25:
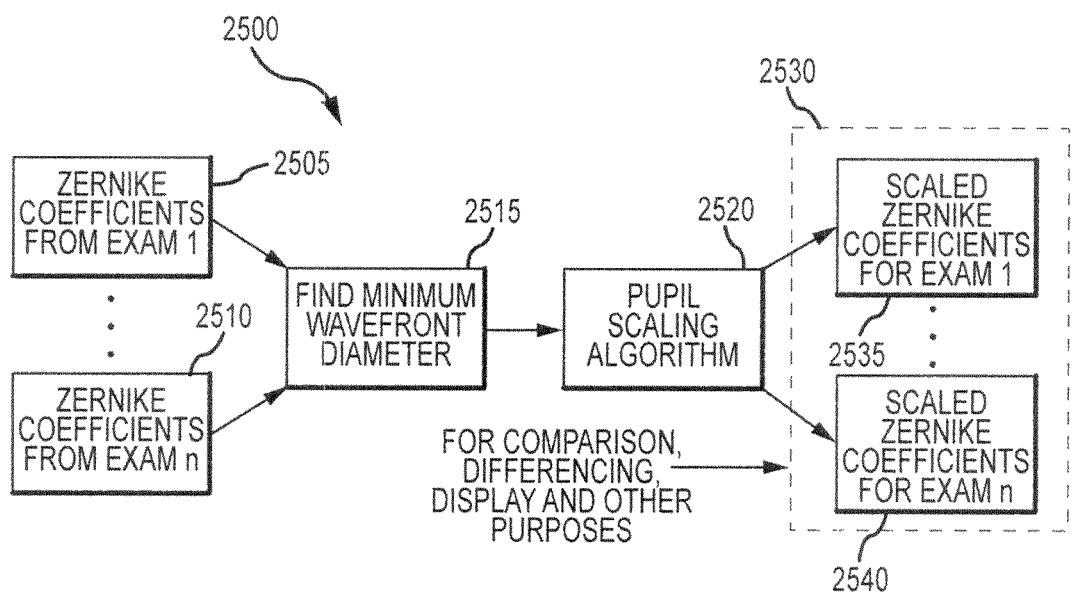
FIG. 25 illustrates aspects of diagnostic display techniques for comparing or differencing among different exams from the same eye at different timestamps or for different eyes according to embodiments of the present invention.

FIG. 25 provides a flow chart showing aspects of diagnostic display techniques for comparing or differencing among different exams from the same eye at different timestamps (which may be on the same day, or on different days) or for different eyes. As shown here, system 2500 can include a first module 2505 that receives Zernike coefficient information related to a first examination, and a second or $n^{th}$ module 2510 that receives Zernike coefficient information related to a second or $n^{th}$ examination. System 2500 also includes a minimum wavefront diameter module 2515 that operates to determine a minimum wavefront diameter based on or corresponding to information received from the first module 2505, the second module 2510, or both. System 2500 further includes a pupil scaling algorithm module 2520 that can generate scaled information based on the minimum wavefront diameter information received from minimum wavefront diameter module 2515. FIG. 25 also illustrates an analysis module 2530, which can operate to compare, difference, or display aspects of the various examinations, optionally based scaled information received from pupil scaling algorithm module 2520. As shown here, analysis module 2530 includes a first scaled Zernike coefficient module 2535 that generates or processes scaled Zernike coefficient information related to the first examination, and a second or $n^{th}$ scaled Zernike coefficient module 2540 that generates or processes scaled Zernike coefficient information related to the second or $n^{th}$ examination.

The systems and procedures described in FIGS. 24 and 25 can incorporate scaling or other features described in previously incorporated U.S. patent application Ser. No. 12/722,881, filed Mar. 12, 2010.

Figure 26:
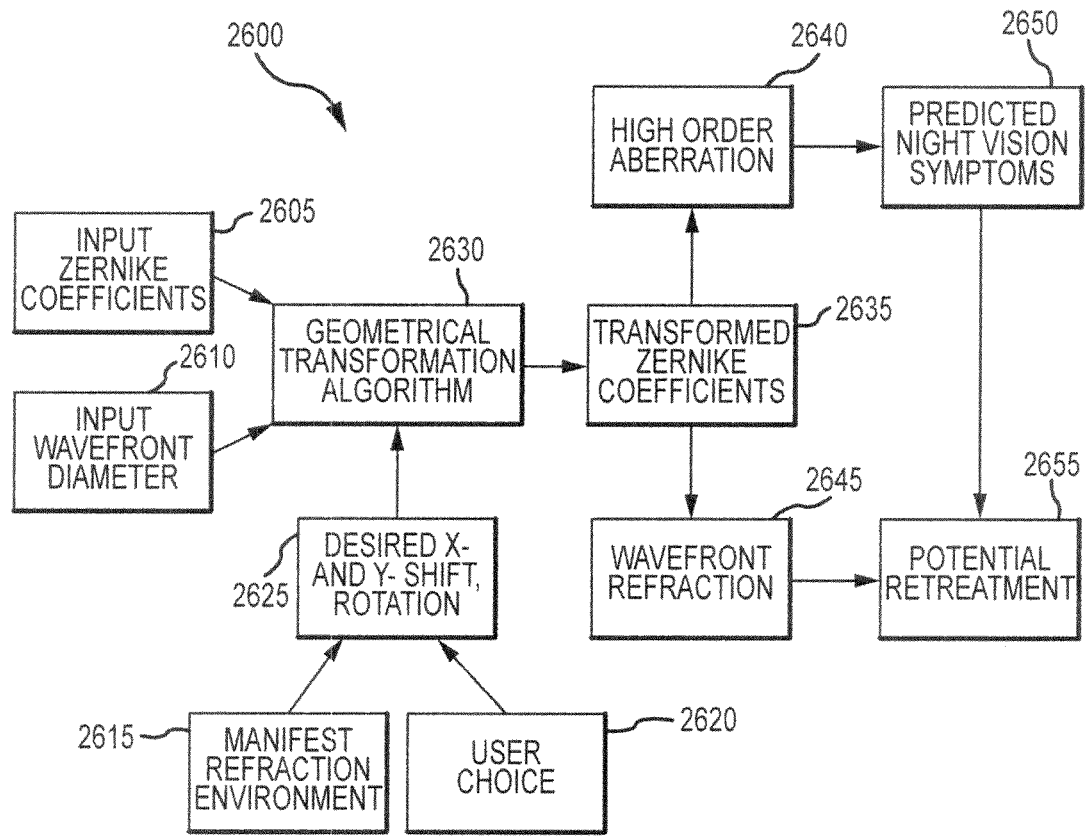
FIG. 26 illustrates aspects of the use of diagnostic display and the use of retreatment and enhancement treatment by geometrical transformation techniques according to embodiments of the present invention.

FIG. 26 provides a flow chart illustrating aspects of the use of diagnostic display and the use of retreatment and enhancement treatment by means of a geometrical transformation algorithm. For example, a difference between a first geometrical configuration and a second geometrical configuration can include a cyclorotation, a pupil center shift or decentration (e.g. x- and y-shifts), a pupil constriction, a pupil dilation, or any combination thereof. As shown here, system 2600 can include an input module 2605 that receives Zernike coefficient information, an input module 2610 that receives wavefront diameter information, a manifest refraction environment module 2615 that receives manifest refraction environment information, and a user choice module 2620 that receives user choice information. Zernike coefficient information can include information from a wavefront examination, and encompass low order and high order aberrations. Manifest refraction environment information can encompass data related to lighting conditions. User choice information can encompass data related to physicians or operators, for example according to their needs or preferences.

A desired x- and y-shift, rotation, or pupil size module 2625 can determine a desired x- and y-shift, rotation, or pupil size change based on manifest refraction environment information and user choice information received from manifest refraction environment module 2615 and user choice module 2620, respectively. A geometrical transformation algorithm module 2630 can operate to determine transformed Zernike coefficients based on Zernike coefficient information received from input module 2605, wavefront diameter information received from input module 2610, and desired x- and y-shift, rotation, or pupil size change information received from desired x- and y-shift, rotation, or pupil size change module 2625.

As shown here, geometrical transformation algorithm module 2630 can output a set of transformed Zernike coefficients 2635. High order aberration module 2640 can operate to determine high order aberrations based on the transformed Zernike coefficient information 2635. Similarly, wavefront refraction module 2645 can operate to determine a wavefront refraction based on the transformed Zernike coefficient information 2635. According to some embodiments, a high order aberration can be induced by various geometrical transformations, including cyclorotation, pupil center shift or decentration, pupil constriction, or pupil dilation. A predicted night vision symptom module 2650 can determine predicted night vision symptoms based on high order aberration information received from high order aberration module 2640. A potential treatment or retreatment module 2655 can determine a potential treatment or retreatment based on wavefront refraction information received from wavefront refraction module 2645 and predicted night vision symptom information received from predicted night vision symptom module 2650. In some cases, a predicted night vision symptom can include a spherical aberration. Treatment module 2655 can be configured to reduce low order aberrations (e.g. as determined from a wavefront refraction), and to reduce night vision symptoms.

Figure 27:
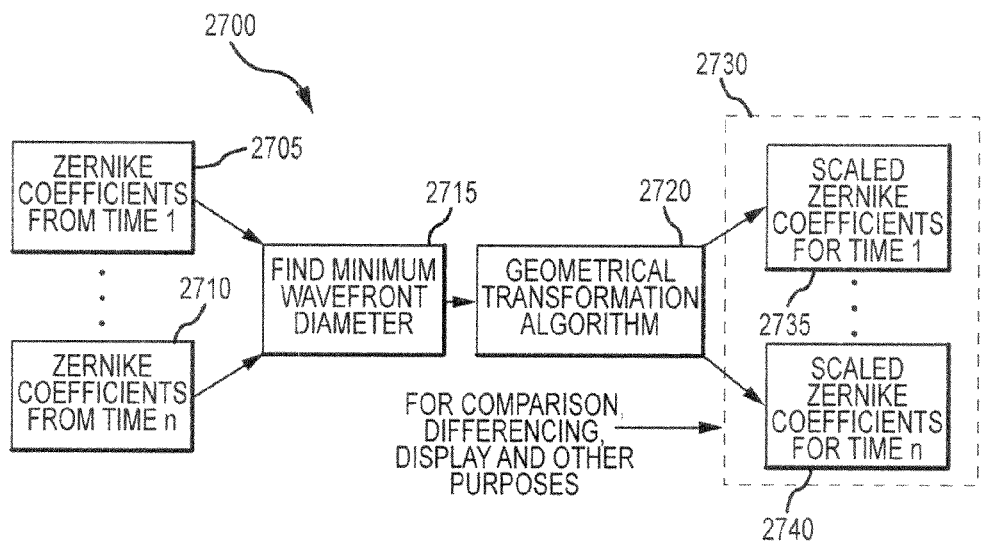
FIG. 27 shows aspects of diagnostic display techniques for comparing or differencing among different exams from the same eye at different timestamps or for different eyes according to embodiments of the present invention.

FIG. 27 provides a flow chart showing aspects of diagnostic display techniques for comparing or differencing among different exams from the same eye at different timestamps (which may be on the same day, or on different days) or for different eyes. As shown here, system 2700 can include a first module 2705 that receives Zernike coefficient information related to a first examination (e.g. at Time 1), and a second or $n^{th}$ module 2710 that receives Zernike coefficient information related to a second or $n^{th}$ examination (e.g. Time 2 or n). System 2700 also includes a minimum wavefront diameter module 2715 that operates to determine a minimum wavefront diameter based on or corresponding to information received from the first module 2705, the second module 2710, or both. System 2700 further includes a geometrical transformation algorithm module 2720 that can generate scaled information based on the minimum wavefront diameter information received from minimum wavefront diameter module 2715. FIG. 27 also illustrates an analysis module 2730, which can operate to compare, difference, or display aspects of the various examinations, optionally based scaled information received from geometrical transformation algorithm module 2720. As shown here, analysis module 2730 includes a first scaled Zernike coefficient module 2735 that generates or processes scaled Zernike coefficient information related to the first examination, and a second or $n^{th}$ scaled Zernike coefficient module 2740 that generates or processes scaled Zernike coefficient information related to the second or $n^{th}$ examination.

The systems and procedures described in FIGS. 26 and 27 can incorporate geometrical transformation or other features described in previously incorporated U.S. patent application Ser. No. 12/725,575, filed Mar. 17, 2010.

Figure 28:
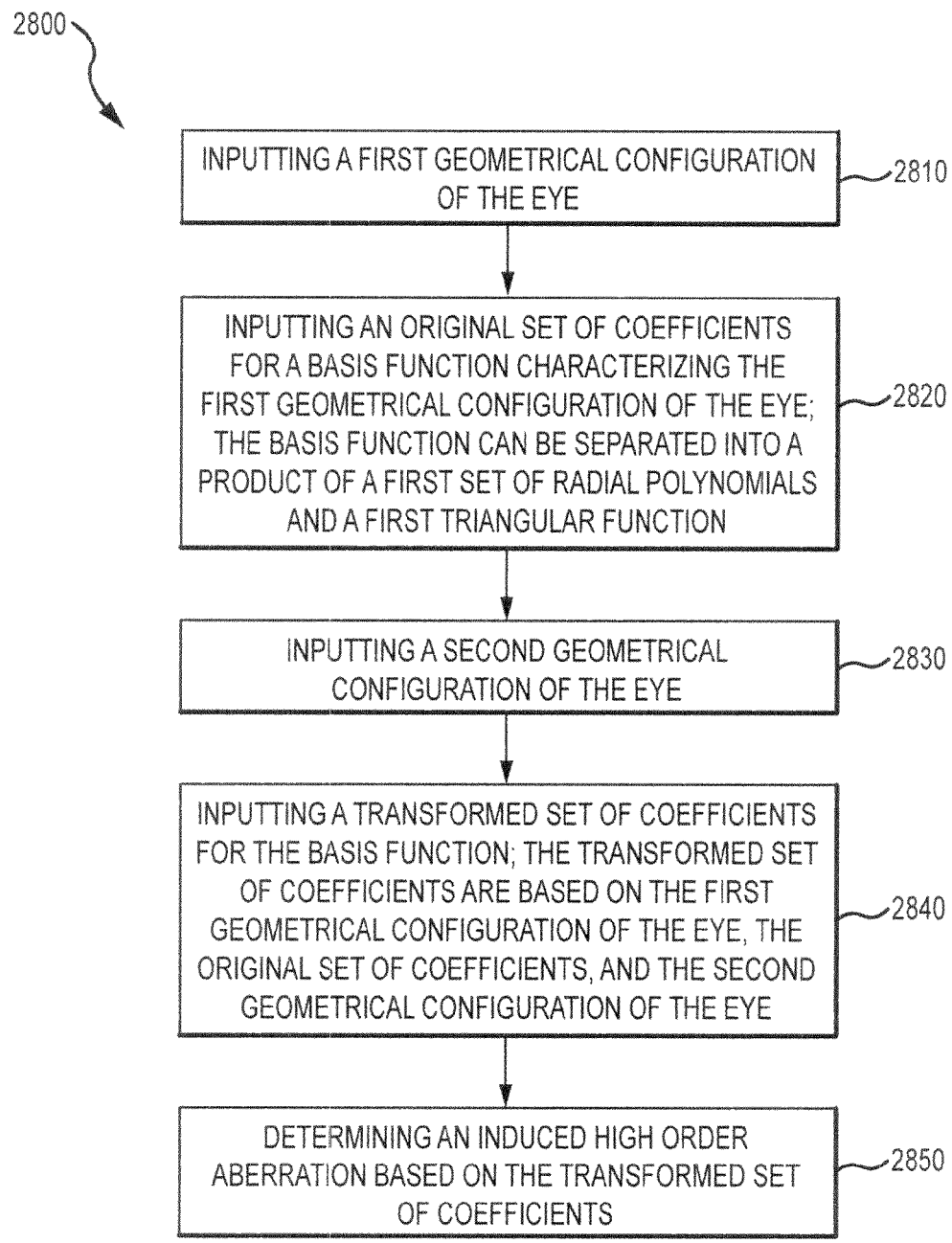
FIG. 28 illustrates aspects of techniques for determining a high order aberration induced by a change in geometrical configuration in an eye of a patient according to embodiments of the present invention.
Figure 29A:
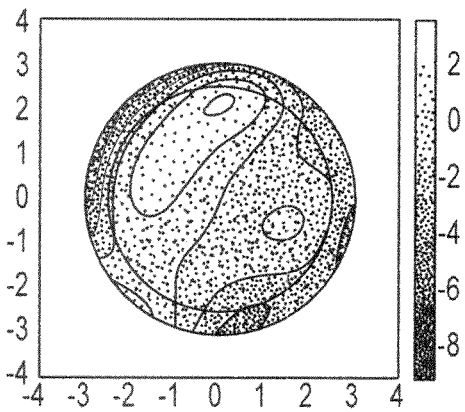
FIGS. 29A to 29D show aspects of zone extensions according to embodiments of the present invention.
Figure 29B:
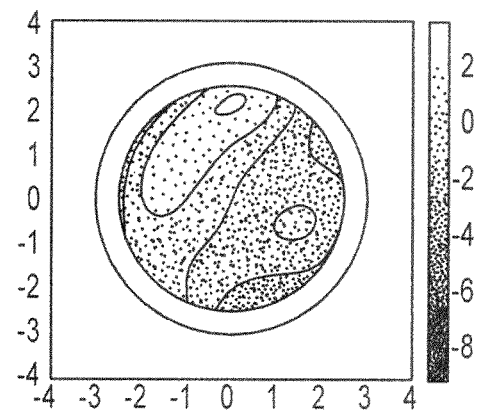
Figure 29C:
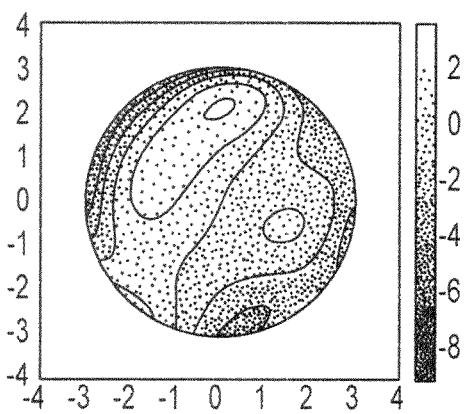
Figure 29D:
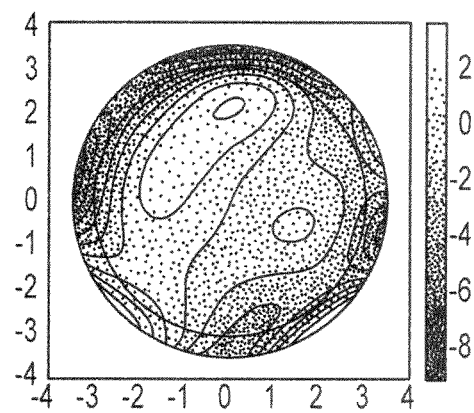

FIG. 28 illustrates aspects of a method 2800 of determining a high order aberration induced by a change in geometrical configuration in an eye of a patient. As shown here, the method includes the steps of inputting a first geometrical configuration of the eye 2810, and inputting an original set of coefficients for a basis function characterizing the first geometrical configuration of the eye 2820. The basis function can be separated into a product of a first set of radial polynomials and a first triangular function. Method 2800 may also include the steps of inputting a second geometrical configuration of the eye 2830, and inputting a transformed set of coefficients for the basis function 2840. The transformed set of coefficients can be based on the first geometrical configuration of the eye, the original set of coefficients, and the second geometrical configuration of the eye. Method 2800 can also include the step of determining an induced high order aberration based on the transformed set of coefficients 2850.

Related Aspects of Zone Extension Systems and Methods

Systems and methods for determining expansion coefficients for dilated pupils or pupils having larger dimensions are described herein. For example, techniques may involve capturing a wavefront map when the pupil size is 5 mm pupil size, and designing a treatment for an optical zone of 6 mm. In some cases exemplary embodiments may involve approaches such as those describe in US 2010/0198567 and US 2010/0253909. Both of these publications are incorporated herein by reference for all purposes.

Part A

Embodiments of the present invention involve scaling Zernike and other coefficients to a larger wavefront diameter for refractive surgery. From an information theory point of view, according to some embodiments scaling Zernike or other coefficients to a smaller or larger diameter can be accomplished when the original set of coefficients contains high spatial frequency information of the optical system. In practice, the amount of information may be related to the wavefront diameter because the number of lenslets in an aberrometer is directly proportional to the wavefront diameter. To investigate the potential error of arbitrarily scaling Zernike coefficients to a larger diameter, a large set of 4256 pre-operative wavefront exams were used. The variability of inter-exam wavefront RMS is compared to the error induced due to scaling Zernike coefficients to a larger diameter. The validity of scaling Zernike coefficients is set when the error due to the scaling is the same as the variability of the inter-exam wavefronts. The inter-exam variability is calculated from eyes having at least 3 same-day pre-operative exams over the same or larger diameters. Scaling Zernike coefficients to a smaller diameter is extensively used because no information loss occurs in this case. Error from scaling Zernike coefficients is calculated by comparing the wavefront for a (scaled-up) set of Zernike coefficients to the wavefront of the average of sets of Zernike coefficients at a larger diameter for the same eye. Wavefront diameters of 5, 5.5, 6, 6.5, and 7 mm were considered.

According to some embodiments, the inter-exam variability of individual Zernike coefficients shows a sinusoidal pattern from the third to the sixth order. The inter-exam variability may be defined as the standard deviation among exams. In some instances, no significant difference may be found for the variability for different pupil sizes. The error due to scaling Zernike coefficients to a larger pupil size is generally smaller than the inter-exam variability when the new diameter is 0.5 mm larger than the original diameter. The error may be comparable to the inter-exam variability when the new diameter is 1 mm larger. The error may be significantly larger when the new diameter is more than 1.5 mm larger than the original diameter. Rescaling Zernike coefficients from a smaller pupil size to a larger one can have practical applications in optical zone extension for wavefront-guided refractive surgery.

Part B

Embodiments of the present invention involve optical zone extension approaches for wavefront-guided refractive surgery. Typically, low order ocular aberrations are independent of pupil size. Therefore, low order aberrations can be used to extend the optical zone to a larger diameter to alleviate night vision problems when ocular wavefront aberrations are captured at a smaller diameter. However, leaving the high order aberrations uncorrected for the extended annular zone may cause problems because high order aberrations may naturally extend beyond the wavefront diameter. Zernike and other rescaling algorithms may be used to obtain the aberrations beyond the originally captured diameter.

According to some embodiments, from an information theory point of view, there may be no restriction for scaling Zernike and other coefficients whether to a smaller or larger diameter, as long as the original set of coefficients contains all the high spatial frequency information of the optical system. It has been shown that the inter-exam ocular wavefront variability can exceed the error induced due to the rescaling of Zernike coefficients to a larger diameter in practical applications, especially when the change in pupil diameter is relatively small. For optical zone extension, use of only the low order aberrations may produce larger error than using the rescaling of Zernike coefficients. In some cases, for optical extension from 6 mm to 6.5 mm, optical zone extension with low order aberrations is found to induce larger error than rescaling Zernike coefficients. In some cases, for optical zone extension from 6 mm to 7 mm, optical zone extension with low order aberrations is found to induce similar error as rescaling Zernike coefficients. Rescaling Zernike coefficients from a smaller pupil size to a larger one can have practical applications in optical zone extension for wavefront-guided refractive surgery.

Part C

Embodiments of the present invention encompass systems and methods for determining ablation designs for optical zone extensions. When the ocular wavefront is captured at a relatively larger pupil, the set of Zernike coefficients over the relatively larger pupil can be scaled to a smaller pupil using an analytical formula, such as that described in U.S. Pat. No. 7,717,562, which is incorporated herein by reference. When the wavefront is captured at a relatively smaller pupil, traditionally there have been obstacles to scaling the set of Zernike coefficients over the relatively smaller pupil to a relatively larger pupil, particularly when the optics of the part between the two sets of pupils is not known.

Techniques described herein provide treatment algorithm that are able to create a reasonable treatment target given a relatively small pupil at wavefront capture. In some cases, the unknown part between the smaller wavefront diameter (e.g. 5 mm) to the larger optical zone (e.g. 6 mm) is blended with the low order aberrations. Advantageously, embodiments of the present invention allow the high order aberrations to be extended to a larger optical zone.

Optical Zone Extension Example

An original wavefront over 6 mm is shown in FIG. 29 (A). When it is scaled down to 5 mm, the scaled wavefront is identical to the inner 5 mm on the original wavefront as shown in FIG. 29 (B). When this scaled wavefront is scaled up to 6 mm as shown in FIG. 29 (C), it is identical to the original wavefront. When this wavefront is scaled up to 7 mm as shown in FIG. 29 (D), there is a significant amount of high order aberration coming in to the area between 6 mm and 7 mm. However, over the inner 6 mm area, it is still identical to the original wavefront.

FIGS. 29A to 29D provide a wavefront extension example illustrating (A) the original wavefront over a 6 mm pupil with a circle mark over 5 mm, (B) the original wavefront scaled down to 5 mm, (C) the wavefront in (B) scaled up to 6 mm, and (D) the wavefront in (C) scaled up to 7 mm.

FIGS. 29A to 29D indicate that the Zernike coefficient scaling is correct whether it is used to scale up or down, particularly where there is no higher spatial frequency information other than that defined in the original wavefront. As an example, assuming the entire optics of a particular eye can be described by spatial frequency up to 60 cpd, and assuming the wavefront over 6 mm is captured with an aberrometer for spatial frequency information up to 60 cpd that is expressed in up to $8^{th}$ order Zernike polynomials, the set of Zernike coefficients can be safely scaled to any smaller pupil sizes or any reasonable larger pupil sizes.

Figure 30A:
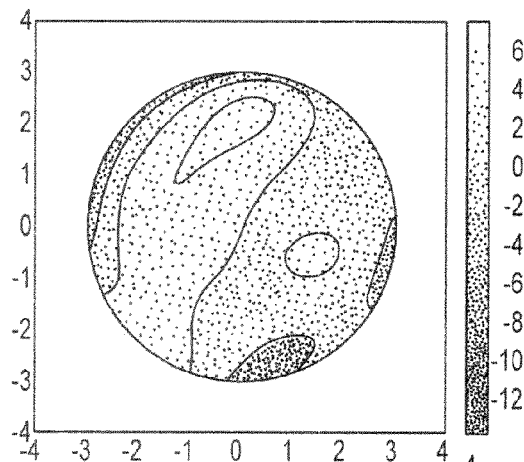
FIGS. 30A to 30C show aspects of zone extensions according to embodiments of the present invention.
Figure 30B:
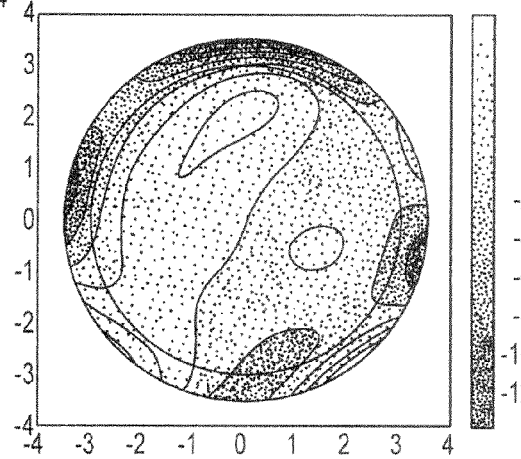
Figure 30C:
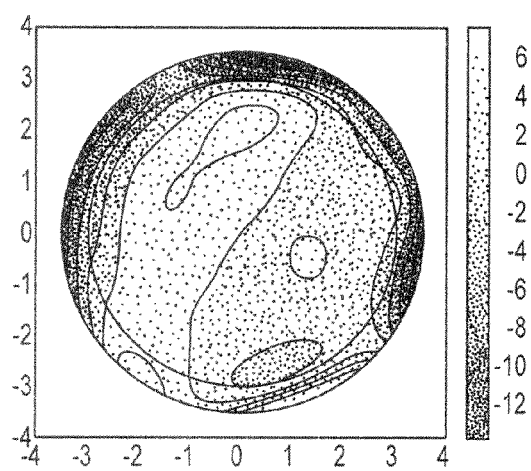
Figure 31A:
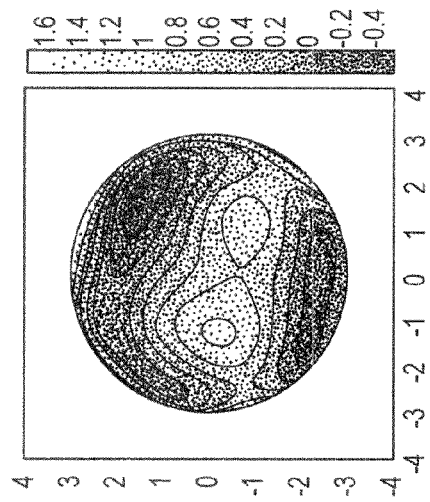
FIGS. 31A to 31D show aspects of zone extensions according to embodiments of the present invention.
Figure 31B:
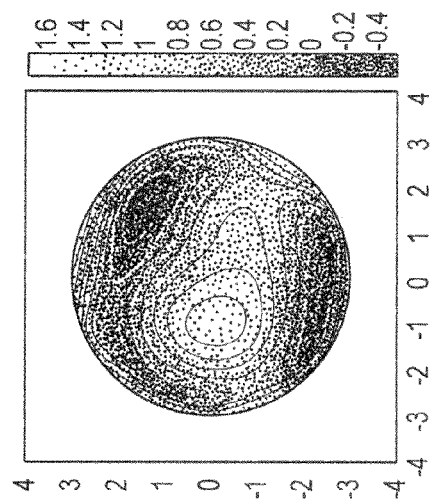
Figure 31C:
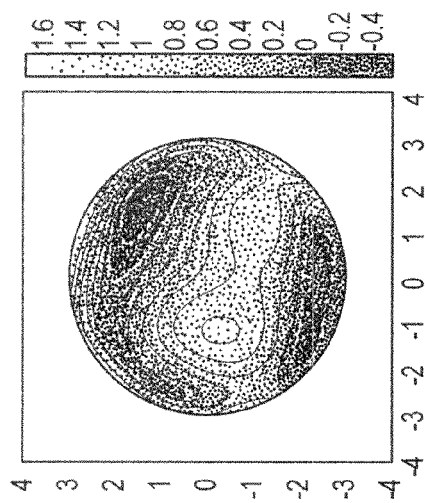
Figure 31D:
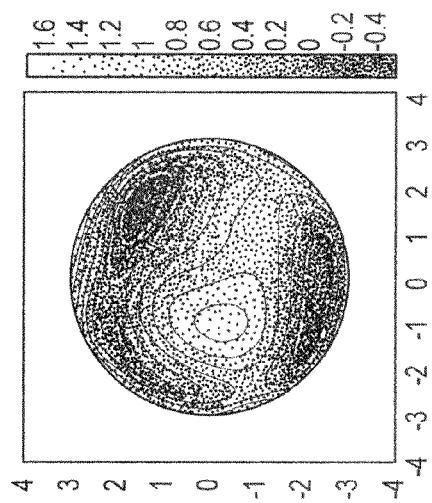
Figure 32A:
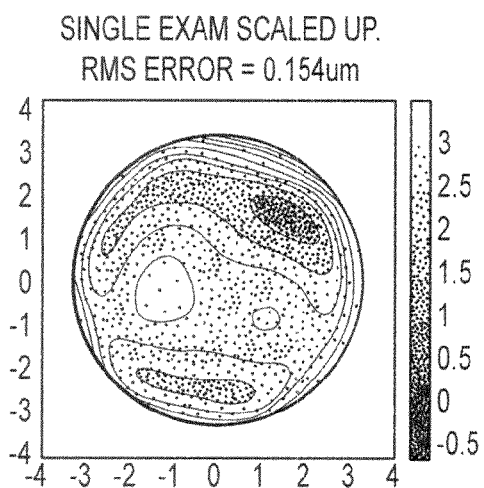
FIGS. 32A to 32D show aspects of zone extensions according to embodiments of the present invention.
Figure 32B:
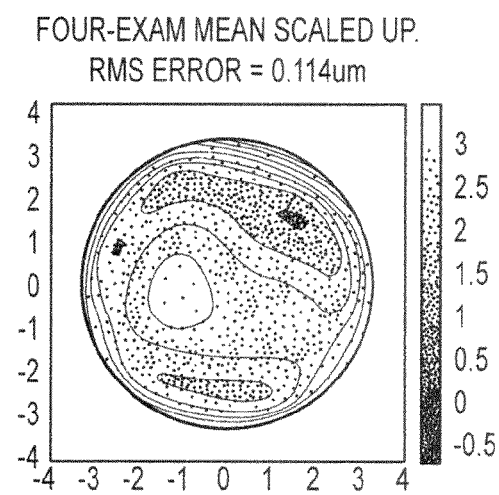
Figure 32C:
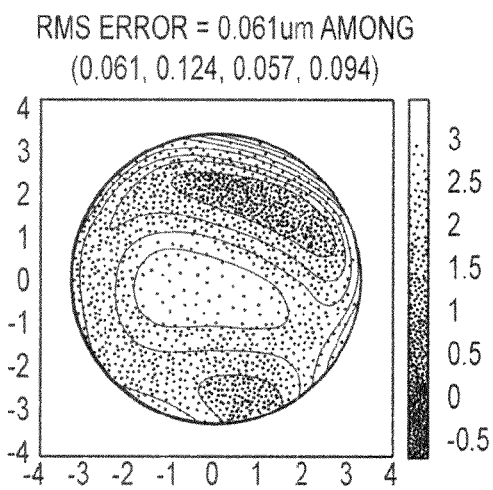
Figure 32D:
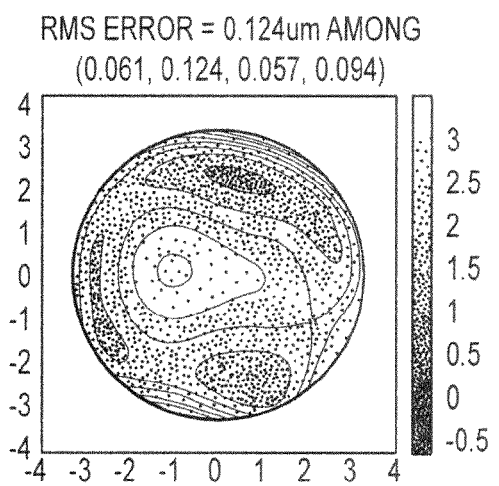
Figure 33A:
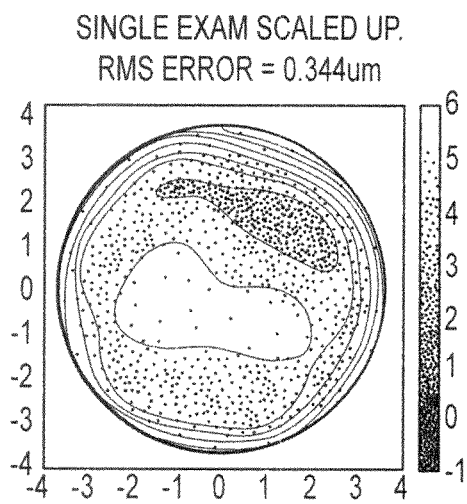
FIGS. 33A to 33D show aspects of zone extensions according to embodiments of the present invention.
Figure 33B:
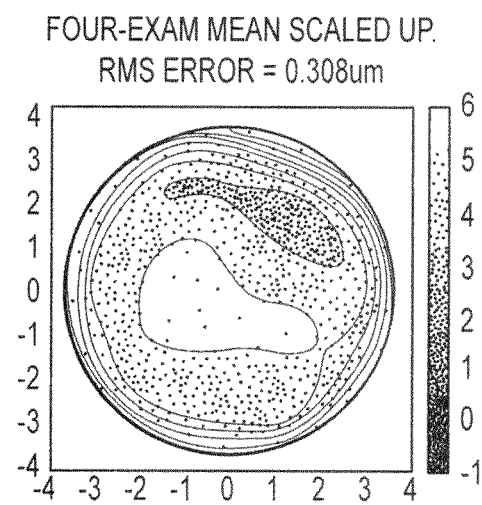
Figure 33C:
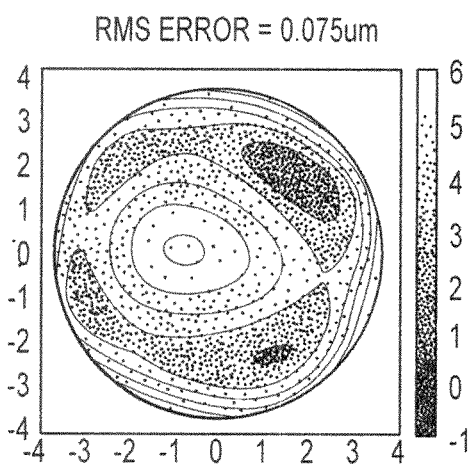
Figure 33D:
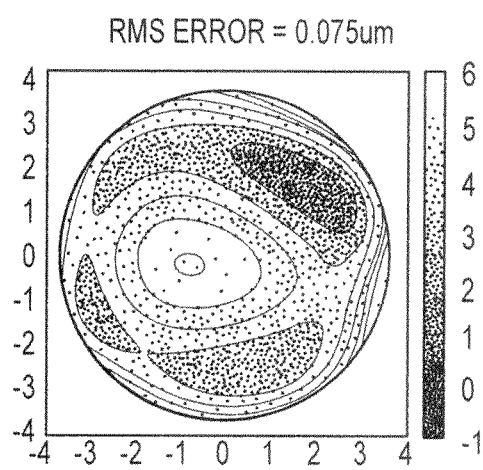

In some instances, if the optics of the eye contain higher frequency information compared to what is contained in the original wavefront over 6 mm, then scaling Zernike coefficients over a larger pupil may lose some high order information. FIGS. 30A to 30C show such an example. The scaled up wavefront over 7 mm is different from the actual wavefront over 7 mm because the middle panel in FIG. 30 only contains spatial frequency information up to the $6^{th}$ order Zernike polynomials while the right panel contains up to the $8^{th}$ order. This explains why the inner 6 mm area in the right panel is not identical to the original wavefront in the left panel.

FIGS. 30A to 30C illustrate aspects of the optics of the eye containing high spatial frequency information that can be described by 8$^{th}$ order Zernike polynomials. FIG. 30A shows the original wavefront captured with 6$^{th}$ order Zernike polynomials. FIG. 30BA shows the wavefront when it is scaled up to 7 mm, which is different from the actual wavefront over 7 mm shown in FIG. 30C.

Wavefront Variation Example

When considering the scaled and the actual wavefronts over 7 mm in FIGS. 30A to 30C, it can be observed that the two maps are not far from the same. In reality, when an eye is captured multiple times, its wavefront maps vary. FIGS. 31A to 31D show an example. FIGS. 31A to 31D provide examples of wavefront variation at different captures over the same pupil diameter on the same eye and displayed on the same scale.

Wavefront Scale-Up Example

For an example eye that has many repeated exams over several different pupil sizes, FIGS. 32A to 32D show the result of two different scale-up approaches. This eye has four repeated exams on the same day over a 6 mm pupil, four repeated exams on the same day over a 6.5 mm pupil, and two repeated exams over a 7 mm pupil. To scale up, it is possible to use any one of the four exams over 6 mm; or it is possible to use the mean of the four exams. FIGS. 32A to 32D show the result of these two approaches. To obtain a more realistic wavefront over 6.5 mm, it is possible to take the average of the four exams over 6.5 mm. Further, it is possible to calculate the RMS error for the difference of the two scaled exams against this average.

FIGS. 32A to 32D provide an example of wavefront scale-up from 6 mm to 6.5 mm, showing (A) a scale-up using a single exam, (B) a scale-up using mean of four exams, (C) an exam captured with 6.5 mm pupil, and (D) another exam captured with 6.5 mm pupil.

For the first case with a random pick, the RMS is as large as 0.154 microns. With the average of four exams, the RMS is only 0.114. On the other hand, the inter-exam variability also shows relatively large RMS (0.061 microns for C and 0.124 for D). Therefore, use of the mean can have an RMS that is smaller than the inter-exam variability, indicating use of the scale-up approach to be practically useful. However, when the scale-up is from 6 mm to 7 mm, the situation becomes different, as shown in FIGS. 33A to 33D. The RMS for the single-exam scale-up is 0.344 microns. With the mean, the RMS for scale-up is 0.308 microns. These values are much larger than the inter-exam variability of 0.075 microns.

FIGS. 33A to 33D provide an example of wavefront scale-up from 6 mm to 7 mm, showing (A) a scale-up using a single exam, (B) a scale-up using mean of four exams, (C) and exam captured with 7 mm pupil, and (D) another exam captured with 7 mm pupil.

Scale-Up versus LOA Extension

Figure 34A:
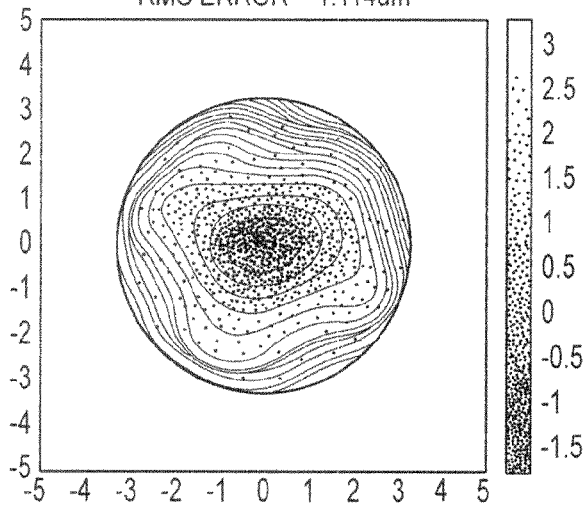
FIGS. 34A to 34C show aspects of zone extensions according to embodiments of the present invention.
Figure 34B:
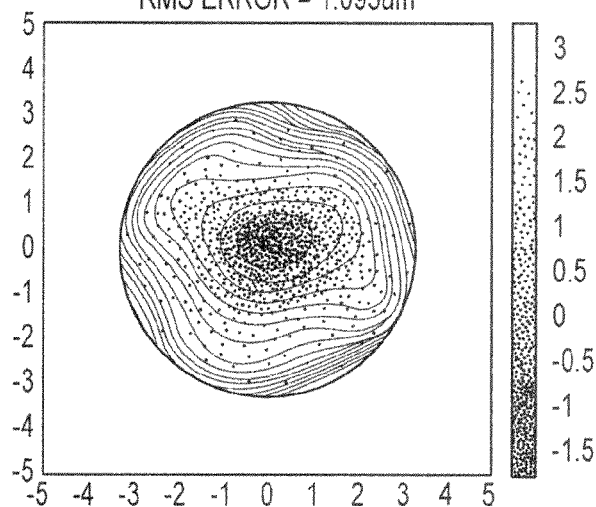
Figure 34C:
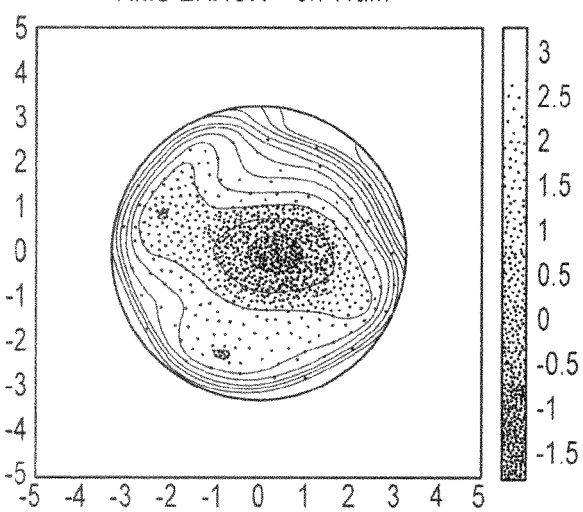

When there is a wavefront exam over a relatively small pupil, for example 5 mm, it is possible to do a zone extension when the optical zone is selected to be 6 mm. Low order aberrations can be used to extend the zone between (in this case) 5 mm and 6 mm. However with such an approach the high order aberrations may be left out in this annular zone. FIGS. 34A to 34C shows the effect of such a zone extension. For the example used in the previous section, the benchmark is a treatment target for the mean of the four exams over the 6.5 mm. There are then three different approaches: (1) an optical zone extension for a single exam with 6 mm wavefront diameter but 6.5 mm OZ; (2) a single exam with 6 mm wavefront diameter but scaled up to 6.5 mm diameter with 6.5 mm OZ; (3) the mean of four exams with 6 mm wavefront diameter but scaled up to 6.5 mm diameter with 6.5 mm OZ. The RMS values for these three treatment targets within the OZ are 1.1142, 1.0927, and 0.7108 microns, respectively.

Figure 35A:
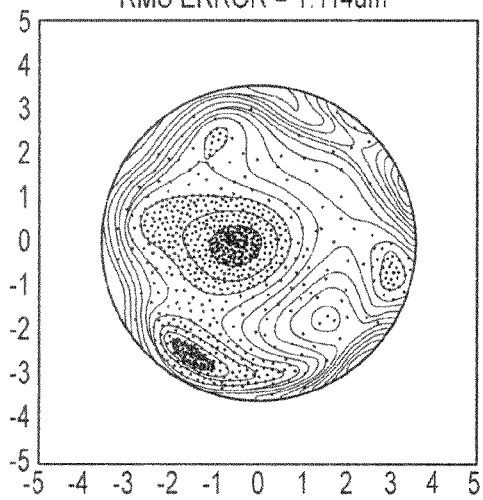
FIGS. 35A to 35C show aspects of zone extensions according to embodiments of the present invention.
Figure 35B:
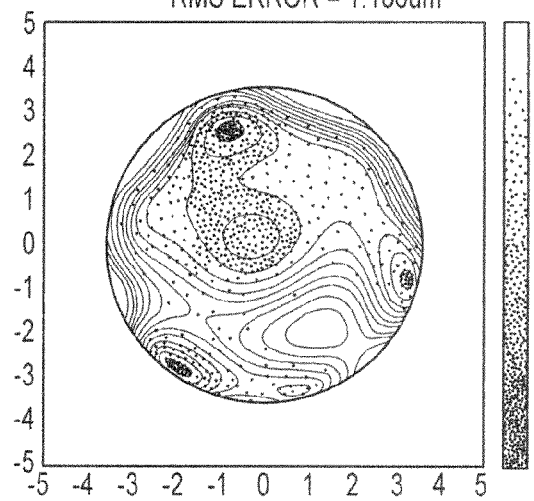
Figure 35C:
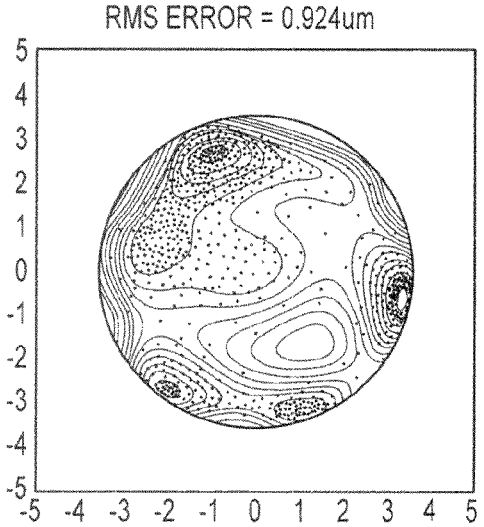

The optical zone extension using the LOA appears to leave the highest RMS error. Similarly, when the OZ is extended to 7 mm, the residual error maps are shown in FIGS. 35A to 35C. The RMS values are now 1.1138, 1.1860, and 0.9239 microns, respectively. This time, the three values are closer to each other. However, there may still be little or no advantage for using zone extension approach.

FIGS. 34A to 34C show optical zone extension with low order aberrations (FIG. 34A), single-exam scale up from 6 mm Zernikes to 6.5 mm Zernikes (FIG. 34B), and four-exam scale up from 6 mm Zernikes to 6.5 mm Zernikes (FIG. 34C).

FIGS. 35A to 35C show optical zone extension with low order aberrations (FIG. 35A), single-exam scale up from 6 mm Zernikes to 7 mm Zernikes (FIG. 35B), and four-exam scale up from 6 mm Zernikes to 7 mm Zernikes (FIG. 35C).

Conclusions

Scaling Zernike coefficients from a smaller pupil size to a larger pupil size may find some practical applications in refractive surgery, especially when the difference in the pupil size is relatively small. With half a millimeter scale-up, the potential error may be smaller than the inter-exam variability. This scale-up may be used effectively for optical extension application, producing better outcomes than implementations that uses the low order aberrations only.

Part D

When obtaining wavefront data from a patient as part of a wavefront examination procedure, in many cases it is not possible to dilate the patient's pupil to an optimal or desired size, such as a 6 mm diameter pupil. For example, it may only be possible to obtain wavefront examination information from the pupil when it is at only 4 mm or 5 mm. Some current techniques may be used to extend low order aberration information from the smaller pupil dimension to the larger pupil dimension. There are challenges for extending high order aberration information from smaller to larger pupil dimensions, however. For example, where wavefront information is captured for a 5 mm pupil dimension, and it is desirable to use a 6 mm optical zone, there may be difficulties when there is little or no available wavefront information corresponding to the area between 5 mm and 6 mm. Extending low order aberrations from 5 mm to 6 mm may be straightforward as the low order aberrations are not pupil size dependent and hence the powers remain the same. If, however, the eye has significant high order aberrations between 5 mm and 6 mm, there may be disruptions or changes in curvature between these two zones that present challenges for treatment development.

Scaling factors as described herein can be used to determine a modified normalized Zernike expansion coefficient for an optical system, where an original normalized Zernike expansion coefficient for the optical system is associated with a first aperture dimension, and a modified normalized Zernike expansion coefficient for the optical system is associated with a second aperture dimension larger than the first aperture dimension.

Such approaches can be evaluated by considering available clinical data. In some instances, multiple wavefront exams have been performed on certain patient eyes at various pupil dimensions, for example at 4 mm, 5 mm, 6 mm, 7 mm, and the like, for the same eye.

Embodiments of the present invention also encompass techniques for determining thresholds or to what extent information can be extended to larger pupil dimensions associated with optical zone extensions or pupil dilations. For a particular patient eye, when taking multiple measurements or exams, there may be variability between exams, which can be referred to as this inter-exam variability. Such variability may occur with exams performed for the same eye at the same pupil sizes.

When scaling wavefront information from a smaller pupil size to a larger pupil size, it is possible to compare the scaled larger pupil size wavefront information to a wavefront examination or a set of wavefront examinations that have been captured for the same eye, to determine whether there is variability or whether the scaled information is accurate.

For example, consider four exams captured at a 6 mm pupil dimension, and taking the average of those wavefront examinations. Now, scaling a 5 mm pupil dimension wavefront examination with various scaling algorithms, it is possible to achieve various scaled 6 mm wavefront representations. The scaled 6 mm pupil dimension wavefronts can be compared with the average of the four wavefront exams taken at 6 mm, and a root mean squares (RMS) error can be calculated.

As another example, it is possible to obtain four wavefront examinations at a 5 mm pupil dimension, take the average of those results, scale the averaged result up to a 6 mm pupil dimension, and then calculate the error.

According to some embodiments, when determining the average of multiple exams, and using the average to scale up to a larger pupil dimension, the error which is introduced may be smaller than the inter-exam variability. In such cases, the fidelity of the scaling up procedure may be considered to be good. In some cases, when scaling up by 1 mm, the error introduced may exceed the error between exams, or the inter-exam variability. When comparing this technique to approaches that involve extending low order aberrations only, however, the extension of 1 mm may provide a better outcome. Hence, from a software implementation perspective, it may still be safe or desirable to extend 1 mm, as compared with techniques that extend only low order aberrations.

Embodiments of the present invention also encompass threshold based on amounts or percentages by which zones may be extended. Such thresholds may be used by physicians to determine whether or to what extent it is desirable or possible to extend information to larger pupil dimensions. In some cases, thresholds may be used as limitations or guides for physicians using or operating treatment devices.

In some cases, it may be assumed that the optical properties of the eye do not change when the pupil dilates. In some cases, it may be assumed that the pupil dilates concentrically. Optionally, it may be assumed that the pupil dilates nonconcentrically. Relatedly, embodiments of the present invention may encompass rescaling techniques that involve pupil center shift, such as those described in previously incorporated US 2010/0253909.

Where the zone extension area contains no higher spatial frequency information, extension may be relatively straightforward. However, where there are significant high order aberrations or additional higher spatial frequency information outside of the examined dimension, there may be difficulties to be addressed when extending the zone. In some cases, there may be a cut-off spatial frequency above which it may be difficult to recover information. The cut-off spatial frequency may be proportional to the pupil dimension or size. For example, increased cut-off spatial frequencies may be associated with larger pupil sizes. In some respects, high order aberrations are similar to high spatial frequency information. High order aberrations, which may be represented by basis data such as Zernike polynomials. High spatial frequency information can e represented by sinusoidal basis functions that involve sine or cosine.

As an example, it is possible to assume that a human eye may be described by 6th order Zernike polynomials. Some techniques may involve capturing aberrations with a smaller pupil (e.g. 4 mm dimension), and extending that information to a larger pupil dimension (e.g. 6 mm). Where there is nothing contained in the eye that is above $6^{th}$ order Zernike polynomials, the extension may be relatively straightforward. The result can be predictable as there is no new spatial frequency information. That is, there is no higher spatial frequency information, e.g. nothing higher than what is originally obtained.

In some cases, however, when going from a smaller to larger pupil dimension there is new higher spatial frequency information compared to what is in the original map. For example, the eye may contain higher spatial frequency information (e.g. $8^{th}$ order) that goes beyond the original capture (e.g. $6^{th}$ order).

It is recognized that when multiple wavefront captures are performed on the same eye, at the same pupil size, on the same date, there may be differences in the results due to various biological factors or other sources of variability. For example, such factors may include microaccommodation, tear film, rotation, shifting, and the like. Typically, multiple repeated evaluations will present some degree or level of fluctuation in the results.

In some cases, it is possible to determine an error due to dilation, and if that error is the same as or smaller than inter-exam variability, then it may be considered acceptable. In some cases, it is possible to perform multiple examinations on a patient, determine an inter-exam variability, and perform a scaling extension if the variability is below a certain threshold.

Part E

LASIK surgery may induce high order aberrations such as spherical aberration. The causes may be multi-factorial, for example, due to biomechanical and healing effects. Optical zone extension may be also be a factor. It has been discovered that for wavefront-guided LASIK and other vision treatment techniques, when the wavefront diameter is smaller than the optical zone, low order aberrations, high order aberrations, or both can be extended to the gap between the wavefront diameter and the optical zone.

One study involves 703 eyes having 6 mm pre-operative wavefront exams. To estimate the error due to the use of low-order optical zone extension, each exam was masked to a smaller diameter, simulating smaller pupil diameter captures. The wavefront exams for the different diameters were then used by the target controller to create treatment targets for the same eye with identical optical zone of 6 mm. The difference of the two targets within the optical zone may define induction of high order aberrations, from a target viewpoint.

Figure 36A:
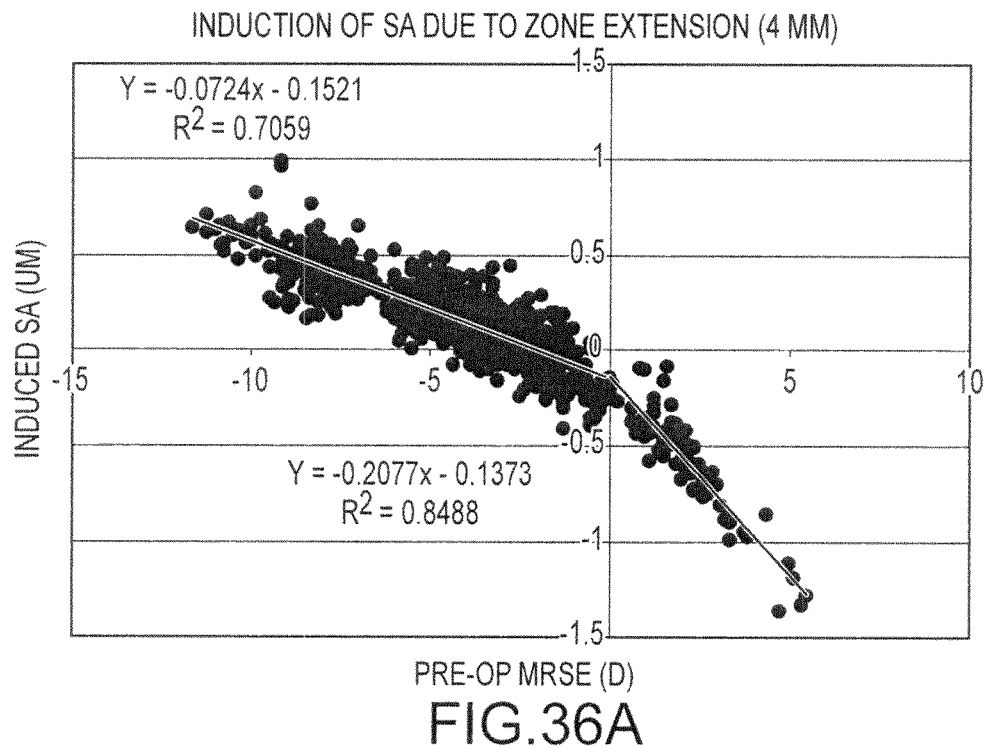
FIGS. 36A and 36B show aspects of zone extensions according to embodiments of the present invention.
Figure 36B:
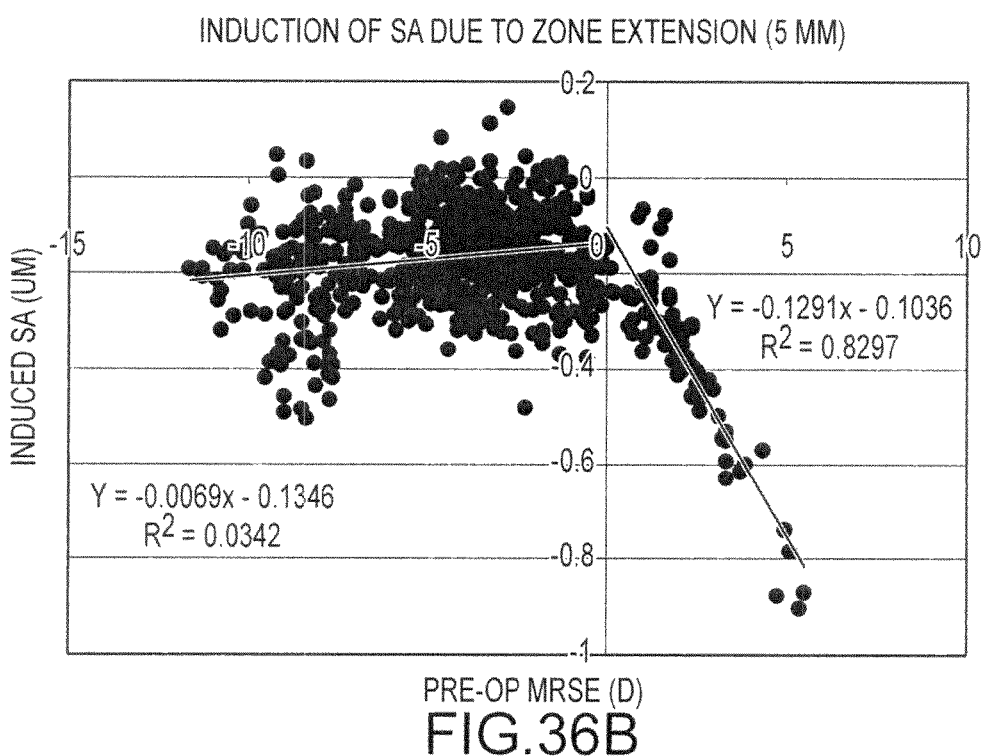

FIGS. 36A and 36B show the induction of spherical aberration (SA) due to optical zone extension. For myopia, zone extension from 5 mm induces very little SA but significant SA when the extension is from 4 mm. For hyperopia, negative SA is induced. Induction of spherical aberration due to optical zone extension from 4 mm (FIG. 36A) and 5 mm (FIG. 36B) to 6 mm, is shown, respectively.

Figure 37A:
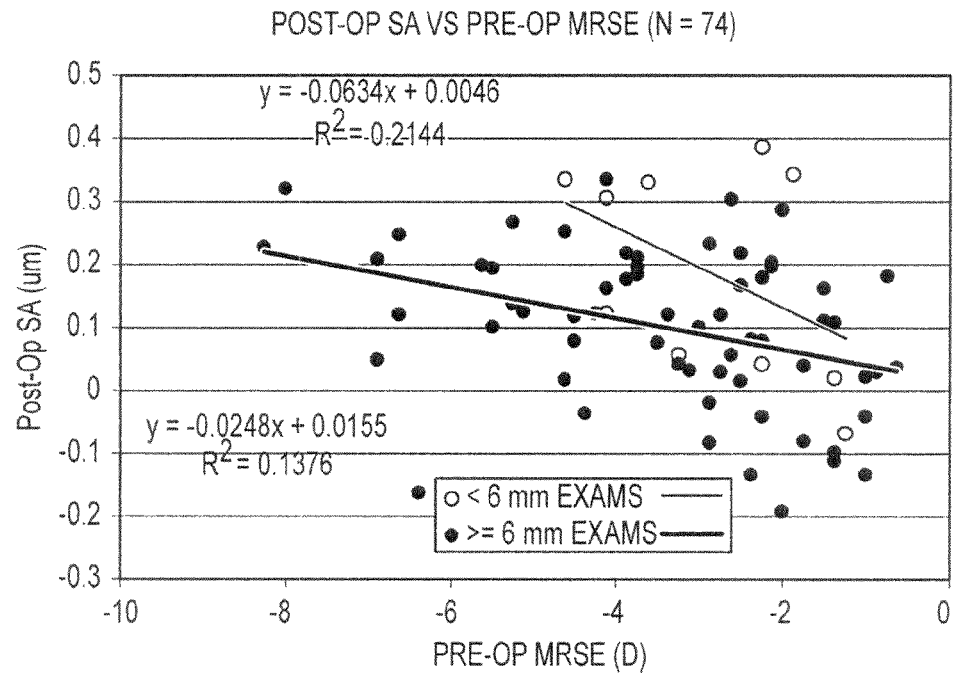
FIGS. 37A and 37B show aspects of zone extensions according to embodiments of the present invention.
Figure 37B:
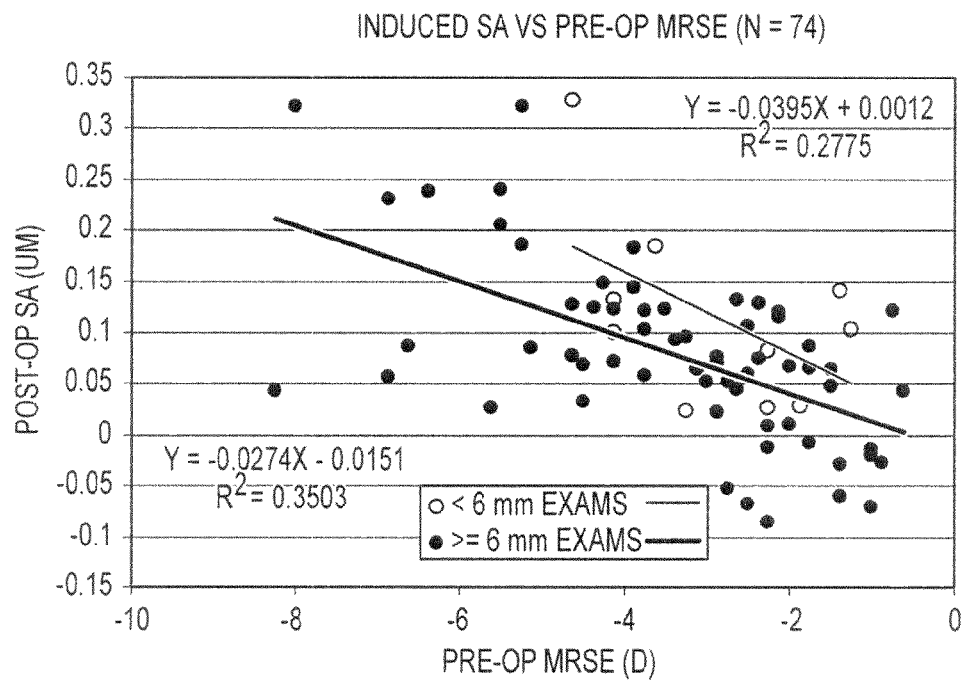

In another study, 74 eyes were put into two groups: a first group of 10 eyes having wavefront diameters smaller than 6 mm and a second group of 64 eyes having wavefront diameters of at least 6 mm. The post-operative and induced spherical aberrations are plotted in FIGS. 37A and 37B as a function of the pre-operative MRSE. In both cases, eyes treated with zone extension show a higher slope than those without zone extension, indicating a more severe induction of spherical aberration that may be directly related to the target shape. The actual post-operative (FIG. 37A) and induction (FIG. 37B) of spherical aberration as a function of pre-operative MRSE for eyes treated with zone extension (10 eyes) and without zone extension (64 eyes).

For the post-op case, the SA is 0.187±0.162 um for eyes with zone extension and is 0.099±0.124 um for eyes without zone extension. The difference is statistically significant (p=0.026). For the induction, the SA is 0.115±0.092 um for eyes with zone extension and is 0.078±0.086 um. However, the difference is not statistically significant (p=0.106).

Based on the clinical data discussed above, it has been shown that optical zone extension may contribute to the overall induction of spherical aberration. For vision treatment techniques, when the wavefront diameter is smaller than the optical zone, it can be useful to include low order aberrations, high order aberrations, or both, when extending across the gap between the wavefront diameter and the optical zone. In some cases, inclusion of high order aberrations when extending across the gap can lead to improved results.

Part F

Embodiments of the present invention encompass various optical-zone extension approaches, such as the two extension approaches discussed below. Low order ocular aberrations may be considered to be independent of pupil size. Therefore, low order aberrations can be used to extend the optical zone to a larger diameter to alleviate night vision problems when ocular wavefront aberrations are captured at a smaller diameter. Because high order aberrations may extend beyond the wavefront diameter, it may be useful to correct for high order aberrations for the extended annular zone. It has been discovered that certain rescaling techniques, such as the Zernike rescaling algorithm described by Dai in JOSAA, Vol 26: 539-543 (2006), incorporated herein by reference, can be used to obtain the aberrations beyond the originally captured diameter. Statistical analysis of two clinical studies (703 eyes and 130 eyes, respectively) is used to evaluate the error induced due to optical zone extension.

Figure 38A:
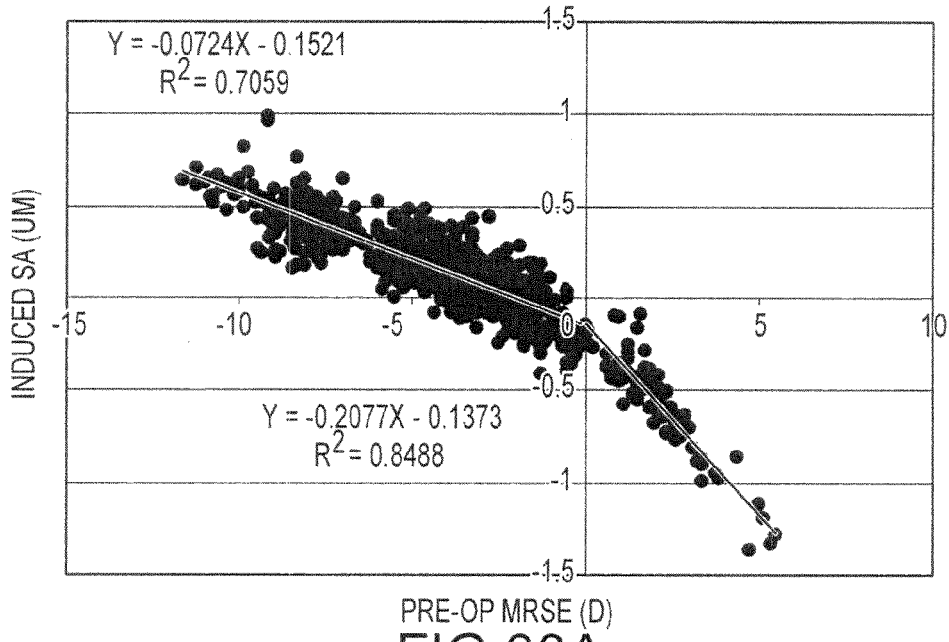
FIGS. 38A and 38B show aspects of zone extensions according to embodiments of the present invention.
Figure 38B:
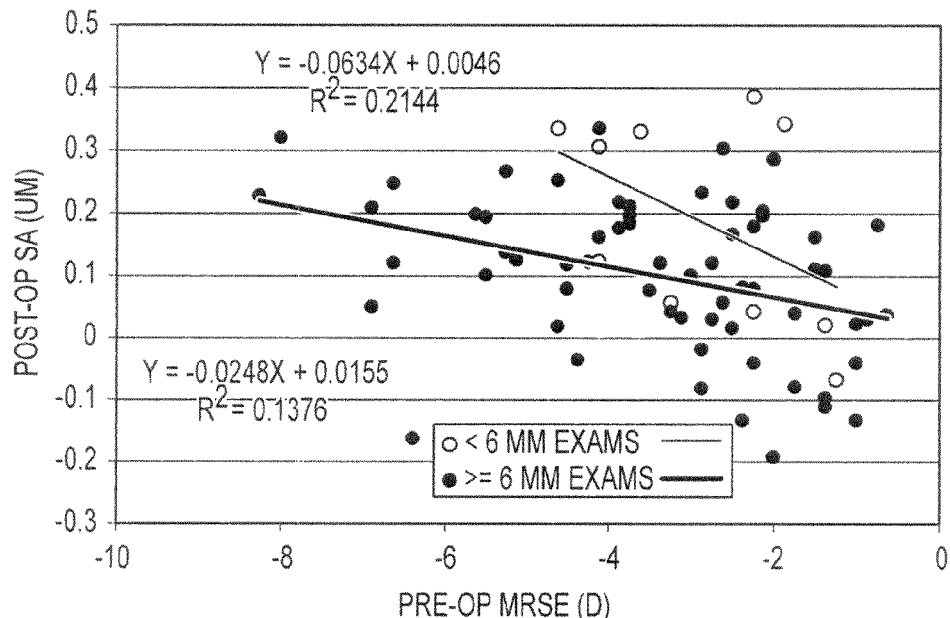

According to some embodiments, when the original set of Zernike coefficients contains all the high spatial frequency information of the optical system, there may be no restriction for scaling Zernike coefficients whether to a smaller or larger diameter, from an information theory point of view. It has been shown from a multi-center clinical study (703 eyes) that the inter-exam ocular wavefront variability can exceed the error induced due to the rescaling of Zernike coefficients to a larger diameter in practical applications, especially when the change in pupil diameter is relatively small. For optical zone extension, two studies were conducted. In one study, for 703 eyes having 6 mm wavefront captures, the wavefront maps were masked to 4 mm. Treatment targets for each eye with and without zone extension were calculated. The induction of the spherical aberration (SA) due to the zone extension is significant as shown in FIG. 38A. In another study involving 74 eyes, 10 eyes were treated using zone extension (wavefront diameter from 5 mm to 5.75 mm) and the other 64 eyes were treated without zone extension (6 mm OZ was used for all eyes). The post-operative (3M-6M) SA is shown as two cohorts in FIG. 38B. For the cohort (10 eyes) having wavefront diameter smaller than 6 mm, it induces statistically significantly (p=0.026) greater spherical aberration (0.187±0.168 μm) than the cohort (64 eyes) having at least 6 mm wavefront diameter (0.099±0.124 μm). FIG. 38A shows results from the 703 eye study, and FIG. 38B shows results from the 74 eye study.

Based on the above, it has been shown that rescaling Zernike coefficients from a smaller pupil size to a larger one can have practical applications in optical zone extension for wavefront-guided refractive surgery.

Each of the above calculations or operations may be performed using a computer or other processor having hardware, software, and/or firmware. The various method steps may be performed by modules, and the modules may comprise any of a wide variety of digital and/or analog data processing hardware and/or software arranged to perform the method steps described herein. The modules optionally comprising data processing hardware adapted to perform one or more of these steps by having appropriate machine programming code associated therewith, the modules for two or more steps (or portions of two or more steps) being integrated into a single processor board or separated into different processor boards in any of a wide variety of integrated and/or distributed processing architectures. These methods and systems will often employ a tangible media embodying machine-readable code with instructions for performing the method steps described above. Suitable tangible media may comprise a memory (including a volatile memory and/or a non-volatile memory), a storage media (such as a magnetic recording on a floppy disk, a hard disk, a tape, or the like; on an optical memory such as a CD, a CD-R/W, a CD-ROM, a DVD, or the like; or any other digital or analog storage media), or the like.

As noted above, a variety of output data can be generated by the systems and methods of the present invention. Such outputs may be used for a variety of research, comparison, prediction, diagnostic, and verification operations. The outputs may be evaluated directly, or they may be used as input into the system for further analysis. In some embodiments, the outputs will be used to model the effect of an ocular treatment prior to application. In other embodiments, the outputs will be used to evaluate the effect of an ocular treatment after application. The outputs may also be used to design ocular treatments. Relatedly, it is possible to create treatment tables based on outputs of embodiments of the instant invention.

All patents, patent publications, patent applications, journal articles, books, technical references, and the like discussed in the instant disclosure are incorporated herein by reference in their entirety for all purposes.

While the exemplary embodiments have been described in some detail, by way of example and for clarity of understanding, those of skill in the art will recognize that a variety of modification, adaptations, and changes may be employed. Hence, the scope of the present invention should be limited solely by the claims.

APPENDIX A

Zernike Resizing Polynomials

Zernike resizing polynomials are the basis for calculating the resized Zernike coefficients from an original set of Zernike coefficients when the pupil size is changed. Following are some properties of this set of polynomials.

Property 1.

$$G_n^i(\varepsilon) = \frac{1}{\sqrt{(n+1)}}[\mathcal{R}_{n+2i}^n(\varepsilon) - \mathcal{R}_{n+2i}^{n+2}(\varepsilon)].$$

Proof: This relationship can be proved by dividing $\sqrt{n+1}$ on both sides of Eq. (A1) and comparing the result to Zernike resizing polynomials Eq. (A2).

$$\mathcal{R}^n_{n+2i}(\varepsilon) - \mathcal{R}^{n+2}_{n+2i}(\varepsilon) = \tag{A1}$$

$$\varepsilon^n(n+1)\sqrt{n+2i+1}\sum_{j=0}^{i}\frac{(-1)^{i+j}(n+i+j)!}{j!(i-j)!(n+j+1)!}\varepsilon^{2j}.$$

$$G_n^i(\varepsilon) = \varepsilon^n\sqrt{(n+2i+1)(n+1)}\sum_{j=0}^{i}\frac{(-1)^{i+j}(n+i+j)!}{(n+j+1)!(i-j)!j!}\varepsilon^{2j}. \tag{A2}$$

Property 2.

$G_n^i(1) = 0$ for $i \neq 0$.

Proof: From Property 1, we have $$G_n^i(1) = \frac{1}{\sqrt{(n+1)}}[\mathcal{R}^n_{n+2i}(1) - \mathcal{R}^{n+2}_{n+2i}(1)] \tag{A3}$$

$$= \frac{1}{\sqrt{n+1}}(\sqrt{n+1} - \sqrt{n+1}) = 0,$$

because for any n and i except i=0 it can be shown [Born, M. and Wolf, E., *Principles of Optics,* 5th ed. (Cambridge University Press, 1999), Chap 9]

$$\mathcal{R}^{|m|}_n(1) = \sqrt{n+1}. \tag{A4}$$

Property 3.

$G_n^0(\varepsilon) = 1$.

Proof: Because for i=0, $\mathcal{R}^{n+2}_n(\varepsilon) = 0$, from Property 1 we have $$G_n^0(\varepsilon) = \frac{1}{\sqrt{n+1}}\mathcal{R}^n_n(\varepsilon) = \frac{\varepsilon^n\sqrt{n+1}}{\sqrt{n+1}} = \varepsilon^n. \tag{A5}$$

APPENDIX B

Derivation of Eq. (27)

The wavefront after cyclorotation of angle $\phi$, as shown in FIG. 10, represented by Taylor monomials in Cartesian coordinates, can be given as $$W(\rho,\theta;\phi) = \sum_{p,q} a_p^q \rho^p \cos^q(\theta-\phi)\sin^{p-q}(\theta-\phi). \tag{B1}$$

The Taylor monomials in the original coordinates can be written as $$T_p^q(\rho,\theta;\phi) = T_p^q(\rho,\theta-\phi) \tag{B2}$$

$$= \rho^p[\cos(\theta-\phi)]^q[\sin(\theta-\phi)]^{p-q}$$

$$= \rho^p[\cos\theta\cos\phi + \sin\theta\sin\phi]^q$$

$$[\sin\theta\cos\phi - \cos\theta\sin\phi]^{p-q}$$

-continued $$= \sum_{k=0}^{q}\sum_{l=0}^{p-q}\frac{(-1)^l q!(p-q)!}{k!l!(q-k)!(p-q-l)!}$$

$$(\cos\theta)^{q-k+l}(\sin\theta)^{p-q+k-l} \times$$

$$(\sin\phi)^{k+l}(\cos\phi)^{p-k-l}$$

$$= \sum_{k=0}^{q}\sum_{l=0}^{p-q}\frac{(-1)^l q!(p-q)!}{k!l!(q-k)!(p-q-l)!} \times$$

$$(\sin\phi)^{k+l}(\cos\phi)^{p-k-l}T_p^{q-k+l}(\rho,\theta).$$

Therefore, the rotated Taylor coefficients $b_p^q$ is related to the original Taylor coefficients $a_p^q$ by changing $\phi$ to $-\phi$ in Eq. (B2) as $$b_p^q = \sum_{k=0}^{q}\sum_{l=0}^{p-q}\frac{(-1)^k q!(p-q)!}{k!l!(q-k)!(p-q-l)!}(\sin\phi)^{k+l}(\cos\phi)^{p-k-l}a_p^{q-k+l}. \tag{B3}$$

APPENDIX C

Derivation of Eq. (28)

To derive Eq. (28), it is helpful to start with the definition of Zernike polynomials $$Z_n^m(\rho,\theta) = \mathcal{R}_n^{|m|}(\rho)\Theta^m(\theta), \tag{C1}$$

where the triangular function $$\Theta^m(\theta) = \begin{cases} \sin|m|\theta & (m<0) \\ 1 & (m=0) \\ \cos|m|\theta & (m>0). \end{cases} \tag{C2}$$

Consider a pair of terms, i.e., with the same radial order n but opposite sign of azimuthal frequency m. The Zernike terms of the rotated wavefront can be written as $$\mathcal{R}_n^{|m|}[a_n^{-|m|}\sin|m|(\theta-\phi) + a_n^{|m|}\cos|m|(\theta-\phi)] = \tag{C3}$$

$$\mathcal{R}_n^{|m|}[a_n^{-|m|}(\sin|m|\theta\cos|m|\phi - \cos|m|\theta\sin|m|\phi) +$$

$$a_n^{|m|}(\cos|m|\theta\cos|m|\phi + \sin|m|\theta\sin|m|\phi)] =$$

$$\mathcal{R}_n^{|m|}[(a_n^{-|m|}\sin|m|\phi + a_n^{|m|}\cos|m|\phi)\sin|m|\theta +$$

$$(a_n^{|m|}\cos|m|\phi - a_n^{-|m|}\sin|m|\phi)\cos|m|\theta] =$$

$$\mathcal{R}_n^{|m|}(b_n^{-|m|}\sin|m|\theta + b_n^{|m|}\cos|m|\theta).$$

From these last two lines of Eq. (C3), we have $$b_n^{-|m|} = a_n^{-|m|}\sin|m|\phi + a_n^{|m|}\cos|m|\phi, \tag{C4a}$$

$$b_n^{|m|} = a_n^{|m|}\cos|m|\phi - a_n^{-|m|}\sin|m|\phi, \tag{C4b}$$

APPENDIX D

Derivation of Eq. (32)

Suppose an ocular wavefront is represented by a set of Taylor coefficients $\{a_p^q\}$. When it is decentered by $\Delta u$ and $\Delta v$, we have $$W = \sum_{i=0}^{J} a_i T_i(u - \Delta u, v - \Delta v) \quad \text{(D1)}$$

$$= \sum_{i=0}^{J} a_i (u - \Delta u)^q (v - \Delta v)^{p-q}$$

$$= \sum_{i=0}^{J} a_i \sum_{k=0}^{q} \sum_{l=0}^{p-q} \frac{(-1)^{k+l} q!(p-q)!}{k! l! (q-k)!(p-q-l)!}$$

$$(\Delta u)^k (\Delta v)^l T_{p-k-l}^{q-k}(u, v).$$

In order to obtain the new coefficients $b_p^{q'}$, it is helpful to make the following conversion $$p' = p - k - l, \quad \text{(D2a)}$$

$$q' = q - k. \quad \text{(D2b)}$$

Solving Eq. (D2a, D2b) for k and l, we get $$k = q - q', \quad \text{(D3a)}$$

$$l = p - p' - (q - q'). \quad \text{(D3b)}$$

Substituting k and l back to Eq. (D1), we obtain $$b_p^q \sum_{p', q'} \frac{(-1)^{p-p'} q!(p-q)!}{(q-q')!(p-p'-q+q')!(q')!(p'-q')!} \quad \text{(D4)}$$

$$(\Delta u)^{q-q'} (\Delta v)^{p-p'-q+q'} a_{p'}^{q'}.$$

APPENDIX E

Matlab Code for Geometrical Transformations

```
% This function calculate a new set of Zernike coefficients from an original set when a
% decentration of (du, dv), a rotation of phi counter clockwise, and a pupil resizing of
% e occur.
%
function B = WavefrontTransform(A, du, dv, phi, e);
    B = Z4Z(A, du, dv);
    B = Z3Z(B, phi);
    B = Z2Z(B, e);
% This function converts an original set of Zernike coefficients to a new set when the pupil
% size changes
function B = Z2Z(A, e);
    for i = 0:length(A)-1
        [n, m] = single2doubleZ(i);
        B(i+1) = getB(A, n, m, e);
    end
% This function calculates Zernike coefficients as the pupil resizes
%
function b = getB(A, n, m, e);
    [N, M] = single2doubleZ(length(A)-1); x = 0;
    for i = 1:(N-n)/2
        y = 0;
        for j = 0:i
            z = 1;
            for k = 0:i-2
                z = z * (n+j+k+2);
            end
            y = y + (-1)^(i+j)/factorial(i-j)/factorial(j)*z*e^(2*j);
        end
        jj = double2singleZ(n+2*i, m);
        x = x + sqrt((n+2*i+1)*(n+1))*y*A*(jj+1);
    end
    jj = double2singleZ(n, m);
    b = (A(jj+1) + x)*e^n;
% This function converts Taylor coefficients as map shifts by du, dv
%
function B = T4T(A, du, dv);
    for i = 0:length(A)-1
        B(i+1) = 0;
        [p, q] = single2doubleT(i);
        for j = 0:length(A)-1
            [p2, q2] = single2doubleT(j);
            if(p2 >= p && q2 >= q && p2-p-q2+q >= 0)
                cc = (-1)^(p2-p)*factorial(q2)*factorial(p2-q2)/(...
                    factorial(q2-q)*factorial(p2-p-q2+q)*factorial(q) ...
                    *factorial(p-q));
                B(i+1) = B(i+1) + cc*(du)^(q2-q)*(dv)^(p2-p-q2+q) ...
                    *A(j+1);
            end
        end
    end
% This function converts Zernike coefficients when map shifts du, dv
```

APPENDIX E-continued

Matlab Code for Geometrical Transformations

```
%
function B = Z4Z(A, du, dv);
    A = Z2T(A);
    B = T4T(A, du, dv);
    B = T2Z(B);
% This function calculates Zernike coefficients when map rotates phi
%
function B = Z3Z(A, phi);
    for i= 1:length(A)-1
        [n, m] = single2doubleZ(i);
        jj1 = double2singleZ(n, -abs(m));
        jj2 = double2singleZ(n, abs(m));
        if (m < 0)
            B(i+1) = A(jj1+1)*cos(m*phi)+A(jj2+1)*sin(-m*phi);
        else
            B(i+1) = A(jj1+1)*sin(m*phi)+A(jj2+1)*cos(m*phi);
        end
    end
    B(1) = A(1);
% This function converts Taylor coefficients to Zernike coefficients
%
function A = T2Z(B);
    for i = 0:length(B)-1
        [n, m] = single2doubleZ(i);
        A(i+1) = 0;
        for j = 0:length(B)-1
            [p, q] = single2doubleT(j);
            %% Now calculating the first summation
            s1 = 0;
            for ss = 0:(n-abs(m))/2
                s1 = s1 + (-1)^ss*factorial(n-ss)/factorial(ss)/ ...
                    (n+p-2*ss+2)/factorial((n+m)/2-ss)/factorial( ...
                    (n-m)/2-ss);
            end
            s1 = s1*sqrt(n+1);
            %% Now calculating the second summation
            s2 = 0;
                            for t = 0:q
                                a = factorial(t);
                                b = factorial(q-t);
                                for t2 = 0:p-q
                                    c = factorial(t2);
                                    d = factorial(p-q-t2);
                                    if (m >= 0 && mod(p-q, 2) == 0)
                                        s2 = s2 + 2*(-1)^((p-q)/2+t2)/(a*b*c*d);
                                    elseif (p-2*t-2*t2 == m| |p-2*q-2*t2+2*t == m)
                                            s2 = s2 + (-1)^((p-q)/2=t2)/(a*b*c*d);
                                    end
                                    elseif (m < 0 && mod(p-q, 2) == 1)
                                        if (p-2*q+2*t-2*t2= =-m && 2*q-p+2*t2-2*t = -m)
                                            s2 = s2 + (-1)^((p-q-1)/2+t2)/(a*b*c*d);
                                        elseif (2*q-p-2*t+2*t2-m&&p-2*q-2*t2+2*t= =m)
                                            s2 = s2 - (-1)^((p-q-1)/2+t2)/(a*b*c*d);
                                        end
                                    end
                                end
                            end
            if (m = = 0)
                s2 = s2*factorial(q)*factorial(p-q)/2^p;
            else
                s2 = sqrt(2)*s2*factorial(q)*factorial(p-q)/2^p;
            end
            A(i+1) = A(i+1) + B(j+1)*s1*s2;
        end
    end
% This function converts Zernike coefficients to Taylor coefficients
%
function B = Z2T(A);
    B = zeros(1, length(A));
    for i = 0:length(A)-1
        [n, m] = single2doubleZ(i);
        for j = 0:length(A)-1
            [p, q] = single2doubleT(j);
            if (n < p || mod(n-p,2)= =1 || mod(p-abs(m),2) = =1)
                continue;
            end
            ss = 0;
            fac1 = (-1)^((n-p)/2)*sqrt(n+1)*factorial((n-p)/2) ...
```

APPENDIX E-continued

Matlab Code for Geometrical Transformations

```
                /factorial((p+abs(m))/2)*factorial((n+p)/2) ...
                factorial(abs(m));
            tt2 = (p-abs(m))/2;
            if (m > 0)
                tt = floor(abs(m)/2);
                norm = sqrt(2);
            elseif (m == 0)
                tt = 0;
                norm = 1;
            else
                tt = floor((abs(m)-1)/2);
                norm = sqrt(2);
            end
            sss = 0;
            for t = 0:tt
                for t2 = 0:tt2
                    if (t+t2 = = (p-q)/2 && m >= 0)
                        ss = (-1)^t*norm/factorial(t2)/factorial ...
                        (2*t)/factorial((p-abs(m))/2-t2) ...
                        /factorial(abs(m)-2*t);
                        sss = sss + ss;
                    elseif (t+t2 = = (p-q-1)/2 && m < 0)
                        ss = (-1)^t*norm/factorial(t2)/factorial ...
                        (2*t+1)/factorial((p-abs(m))/2-t2) ...
                        /factorial(abs(m)-2*t-1);
                        sss = sss + ss;
                    end
                end
            end
            ss = sss*fac1;
            j = double2singleT(p, q);
            if (j >= 0)
                B(j+1) = B(j+1) + ss*A(i+1);
            end
        end
    end
end
% This function converts single → double index in Zernike polynomials
%
function [n, m] = single2doubleZ(jj);
        n = floor(sqrt(2*jj+1)+0.5)-1;
        m = 2*jj-n*(n+2);
% This function converts double->single index in Zernike polynomials
%
function jj = double2singleZ(n, m);
        jj = (n^2+2*n+m)/2;
% This function converts single to double index in Taylor monomials
%
function [p, q] = single2doubleT(jj);
        p = floor((sqrt(1+8*jj)-1)/2);
        q = jj-p*(p+1)/2;
% This function converts double to single index in Taylor monomials
%
function jj = double2singleT(p, q);
                                jj=p*(p+1)/2+q;
```

What is claimed is:

1. A system for establishing a prescription that mitigates or treats a vision condition of an eye in a particular patient, the system comprising:

a first module comprising a tangible medium embodying machine-readable code that accepts a first geometrical configuration of the eye;

a second module comprising a tangible medium embodying machine-readable code that determines an original set of coefficients for a basis function characterizing the first geometrical configuration, wherein the basis function can be separated into a product of a first set of radial polynomials and a first triangular function;

a third module comprising a tangible medium embodying machine-readable code that accepts a second geometrical configuration of the eye, wherein a difference between the first geometrical configuration of the eye and the second geometrical configuration of the eye comprises a pupil dilation;

a fourth module comprising a tangible medium embodying machine-readable code that determines a transformed set of coefficients for the basis function, wherein the transformed set of coefficients are based on the first geometrical configuration of the eye, the original set of coefficients, and the second geometrical configuration of the eye, such that each coefficient of the transformed set of coefficients is based on a corresponding coefficient of the original set of coefficients and a corresponding polynomial; and a fifth module comprising a tangible medium embodying machine-readable code that derives the prescription for the particular patient based on the transformed set of coefficients, wherein the prescription mitigates or treats the vision condition of the eye.

2. The system of claim 1, wherein a difference between the first geometrical configuration of the eye and the second geometrical configuration of the eye further comprises a pupil center shift.

3. The system of claim 1, wherein a difference between the first geometrical configuration of the eye and the second geometrical configuration of the eye further comprises a cyclorotation.

4. The system of claim 1, wherein the basis function comprises a Zernike basis function.

5. The system of claim 1, wherein the basis function comprises a Taylor basis function.

6. The system of claim 1, wherein the basis function comprises a Seidel basis function.

7. A method for treating a particular patient with a prescription that mitigates or treats a vision condition of an eye of the patient, the method comprising, through the use of a computer processor:
   obtaining a first wavefront map of the eye that corresponds to a first geometrical configuration of the eye in an evaluation context, the first wavefront map characterized by an original set of coefficients for a basis function that can be separated into a product of a first set of radial polynomials and a first triangular function;
   determining a second wavefront map of the eye that corresponds to a second geometrical configuration of the eye in a treatment context, a difference between the first geometrical configuration of the eye and the second geometrical configuration of the eye comprising a pupil dilation, the second wavefront map characterized by a transformed set of coefficients for the basis function that is based on the first geometrical configuration of the eye, the original set of coefficients, and the second geometrical configuration of the eye, such that each coefficient of the transformed set of coefficients is based on a corresponding coefficient of the original set of coefficients and a corresponding polynomial;
   establishing the prescription for the particular patient based on the transformed set of coefficients; and
   treating the patient with the prescription to mitigate or treat the vision condition of the eye.

8. The method of claim 7, wherein a difference between the first geometrical configuration of the eye and the second geometrical configuration of the eye further comprises a pupil center shift.

9. The method of claim 7, wherein a difference between the first geometrical configuration of the eye and the second geometrical configuration of the eye further comprises a cyclorotation.

10. The method of claim 7, wherein the basis function comprises a Zernike basis function.

11. The method of claim 7, wherein the basis function comprises a Taylor basis function.

12. The method of claim 7, wherein the basis function comprises a Seidel basis function.

13. A computer program product for establishing a prescription that mitigates or treats a vision condition of an eye in a particular patient, the computer program product comprising:
   code for accepting a first geometrical configuration of the eye;
   code for determining an original set of coefficients for a basis function characterizing the first geometrical configuration, wherein the basis function can be separated into a product of a first set of radial polynomials and a first triangular function;
   code for accepting a second geometrical configuration of the eye, a difference between the first geometrical configuration of the eye and the second geometrical configuration of the eye comprises a pupil dilation;
   code for determining a transformed set of coefficients for the basis function, wherein the transformed set of coefficients are based on the first geometrical configuration of the eye, the original set of coefficients, and the second geometrical configuration of the eye, such that each coefficient of the transformed set of coefficients is based on a corresponding coefficient of the original set of coefficients and a corresponding polynomial; and
   code for establishing the prescription for the particular patient based on the transformed set of coefficients, wherein the prescription mitigates or treats the vision condition of the eye.

14. The computer program product of claim 13, wherein a difference between the first geometrical configuration of the eye and the second geometrical configuration of the eye further comprises a pupil center shift.

15. The computer program product of claim 13, wherein a difference between the first geometrical configuration of the eye and the second geometrical configuration of the eye further comprises a cyclorotation.

16. The computer program product of claim 13, wherein the basis function comprises a Zernike basis function.

17. The computer program product of claim 13, wherein the basis function comprises a Taylor basis function.

18. The computer program product of claim 13, wherein the basis function comprises a Seidel basis function.

* * * * *